United States Patent
Reddy et al.

(10) Patent No.: US 11,731,966 B2
(45) Date of Patent: Aug. 22, 2023

(54) COMPOUNDS AND THEIR METHODS OF USE

(71) Applicant: Praxis Precision Medicines, Inc., Cambridge, MA (US)

(72) Inventors: Kiran Reddy, Boston, MA (US); Andrew Mark Griffin, L'lle Bizard (CA); Brian Edward Marron, Durham, NC (US); Gabriel Martinez Botella, Wayland, MA (US)

(73) Assignee: PRAXIS PRECISION MEDICINES, INC., Boston, MA (US)

( * ) Notice: Subject to any disclaimer, the term of this patent is extended or adjusted under 35 U.S.C. 154(b) by 644 days.

(21) Appl. No.: 16/500,795

(22) PCT Filed: Apr. 4, 2018

(86) PCT No.: PCT/US2018/026099
§ 371 (c)(1),
(2) Date: Oct. 3, 2019

(87) PCT Pub. No.: WO2018/187480
PCT Pub. Date: Oct. 11, 2018

(65) Prior Publication Data
US 2021/0355118 A1 Nov. 18, 2021

Related U.S. Application Data

(60) Provisional application No. 62/481,463, filed on Apr. 4, 2017.

(51) Int. Cl.
| | |
|---|---|
| *C07D 471/04* | (2006.01) |
| *C07D 249/18* | (2006.01) |
| *C07D 487/04* | (2006.01) |
| *C07D 401/04* | (2006.01) |
| *C07D 413/06* | (2006.01) |

(52) U.S. Cl.
CPC ......... *C07D 471/04* (2013.01); *C07D 249/18* (2013.01); *C07D 401/04* (2013.01); *C07D 413/06* (2013.01); *C07D 487/04* (2013.01)

(58) Field of Classification Search
None
See application file for complete search history.

(56) References Cited

U.S. PATENT DOCUMENTS

| | | |
|---|---|---|
| 3,845,770 A | 11/1974 | Theeuwes et al. |
| 4,112,095 A | 9/1978 | Allen, Jr. et al. |
| 4,230,705 A | 10/1980 | Allen, Jr. et al. |
| 4,242,515 A | 12/1980 | Trust et al. |
| 4,326,525 A | 4/1982 | Swanson et al. |
| 4,902,514 A | 2/1990 | Barclay et al. |
| 4,992,445 A | 2/1991 | Lawter et al. |
| 5,001,139 A | 3/1991 | Lawter et al. |
| 5,023,252 A | 6/1991 | Hsieh et al. |
| 5,616,345 A | 4/1997 | Geoghegan et al. |
| 5,905,079 A | 5/1999 | Sargent et al. |
| 6,589,952 B2 | 7/2003 | Bakthavatchalam et al. |
| 7,863,279 B2 | 1/2011 | Even et al. |
| 8,030,305 B2 | 10/2011 | Lu et al. |
| 8,173,654 B2 | 5/2012 | Lu et al. |
| 8,198,448 B2 | 6/2012 | Albrecht et al. |
| 8,212,041 B2 | 7/2012 | Albrecht et al. |
| 8,217,177 B2 | 7/2012 | Albrecht et al. |
| 8,524,900 B2 | 9/2013 | Albrecht et al. |
| 8,937,060 B2 | 1/2015 | Cid-Nunez et al. |
| 8,952,034 B2 | 2/2015 | Corkey et al. |
| 9,066,954 B2 | 6/2015 | Albrecht et al. |
| 9,371,329 B2 | 6/2016 | Corkey et al. |
| 10,280,184 B2 | 5/2019 | Friedman et al. |
| 2002/0049208 A1 | 4/2002 | Bakthavatchalam et al. |
| 2009/0124609 A1 | 5/2009 | Albrecht et al. |
| 2009/0203707 A1 | 8/2009 | Rajamani et al. |
| 2010/0088778 A1 | 4/2010 | Mulley et al. |
| 2011/0021521 A1 | 1/2011 | Corkey et al. |
| 2012/0010192 A1 | 1/2012 | Kobayashi et al. |
| 2012/0065191 A1 | 3/2012 | Kiss et al. |
| 2012/0245164 A1 | 9/2012 | Auger et al. |
| 2013/0315895 A1 | 11/2013 | Farrell et al. |
| 2014/0066443 A1 | 3/2014 | Beshore et al. |
| 2014/0303158 A1 | 10/2014 | Corkey et al. |
| 2015/0038503 A1 | 2/2015 | Bourotte et al. |

(Continued)

FOREIGN PATENT DOCUMENTS

| | | |
|---|---|---|
| JP | 2017001991 A | 1/2017 |
| WO | WO-2006061428 A2 | 6/2006 |

(Continued)

OTHER PUBLICATIONS

US 8,754,103 B2, 06/2014, Corkey et al. (withdrawn)
Pal et al., Voltage gated sodium channel inhibitors as anticonvulsant drugs: A systematic review on recent developments and structure activity relationship studies. Bioorganic Chemistry, 2021, 115, p. 1-32.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*

(Continued)

*Primary Examiner* — Po-Chih Chen
(74) *Attorney, Agent, or Firm* — McCarter & English, LLP; Jonathan M. Sparks

(57) ABSTRACT

The present invention is directed to, in part, fused heteroaryl compounds and compositions useful for preventing and/or treating a disease or condition relating to aberrant function of a voltage-gated, sodium ion channel, for example, abnormal late/persistent sodium current. Methods of treating a disease or condition relating to aberrant function of a sodium ion channel including Dravet syndrome or epilepsy are also provided herein.

14 Claims, No Drawings

(56) References Cited

U.S. PATENT DOCUMENTS

| | | | |
|---|---|---|---|
| 2015/0344457 A1* | 12/2015 | Duncan | A61P 43/00 |
| | | | 546/148 |
| 2016/0159801 A1 | 6/2016 | Quinn et al. | |
| 2016/0235718 A1 | 8/2016 | Baraban | |
| 2016/0297799 A1 | 10/2016 | Brookings et al. | |
| 2016/0317536 A1 | 11/2016 | Reich et al. | |
| 2019/0308938 A1* | 10/2019 | McCormack | A61K 31/713 |
| 2019/0389868 A1 | 12/2019 | Reddy et al. | |
| 2020/0179358 A1 | 6/2020 | Reddy et al. | |
| 2020/0247793 A1 | 8/2020 | Reddy et al. | |
| 2020/0377499 A1 | 12/2020 | Griffin et al. | |
| 2020/0377506 A1 | 12/2020 | Reddy et al. | |
| 2020/0377507 A1 | 12/2020 | Griffin et al. | |
| 2021/0171530 A1 | 6/2021 | Reddy et al. | |
| 2021/0188839 A1 | 6/2021 | Reddy et al. | |

FOREIGN PATENT DOCUMENTS

| | | |
|---|---|---|
| WO | WO-2007075567 A1 | 7/2007 |
| WO | WO-2008008539 A2 | 1/2008 |
| WO | WO-2010053757 A1 | 5/2010 |
| WO | WO-2010056865 A1 | 5/2010 |
| WO | WO-2010074807 A1 | 7/2010 |
| WO | WO-2011014462 A1 | 2/2011 |
| WO | WO-2011056985 A2 | 5/2011 |
| WO | WO-2012003392 A1 | 1/2012 |
| WO | WO-2012065546 A1 | 5/2012 |
| WO | WO-2012154760 A1 | 11/2012 |
| WO | WO-2013006463 A1 | 1/2013 |
| WO | WO-2013043925 A1 | 3/2013 |
| WO | WO-2014179492 A1 | 11/2014 |
| WO | WO-2015095370 A1 | 6/2015 |
| WO | WO-2015158283 A1 | 10/2015 |
| WO | WO-2015194670 A1 | 12/2015 |
| WO | WO-2015197567 A1 | 12/2015 |
| WO | WO-2018067786 A1 | 4/2018 |
| WO | WO-2018098491 A1 | 5/2018 |
| WO | WO-2018098499 A1 | 5/2018 |
| WO | WO-2018098500 A1 | 5/2018 |
| WO | WO-2018148745 A1 | 8/2018 |
| WO | WO-2018187480 A1 | 10/2018 |
| WO | WO-2019035951 A1 | 2/2019 |
| WO | WO-2019232209 A1 | 12/2019 |
| WO | WO-2020069322 A1 | 4/2020 |
| WO | WO-2021108513 A1 | 6/2021 |

OTHER PUBLICATIONS

Albright et al. "Synthesis and anxiolytic activity of 6-(substituted-phenyl)-1,2,4-triazolo[4,3-b]pyridazines," *J. Med. Chem.* (1981) vol. 24, pp. 592-600.
Anderson et al. "Unexpected efficacy of a novel sodium channel modulator in Dravet Syndrome," Scientific Reports. 2017.
Anderson et al., "Antiepileptic activity of preferential inhibitors of persistent sodium current," Epilepsia (2014), 55(8), 1274-1283.
Baker et al. "The novel sodium channel modulator GS-458967 (GS967) is an effective treatment in a mouse model of SCN8A encephalopathy," Epilepsia, 2018, 1166-1176.
Barbieri et al. "Late sodium current blocker GS967 inhibits persistent currents induced by familial hemiplegic migraine type 3 mutations of the SCN1A gene," *The Journal of Headache and Pain* (2019) vol. 20, No. 107, pp. 1-13.
Belardinelli et al. "A Novel, Potent, and Selective Inhibitor of Cardiac Late Sodium Current Suppresses Experimental Arrhythmias," *J. Pharmacol. Exp. Ther.* (2013) vol. 344, pp. 23-32.
Guan et al. "Synthesis and anticonvulsant activity of a new 6-alkoxy-[1,2,4]-triazolo[4,3-b]pyridazine," *Eur. J. Med. Chem.* (2010) vol. 45, pp. 1746-1752.
Koltun et al. "Discovery of triazolopyridinone GS-462808, a late sodium current inhibitor (Late INai) of the cardiac Nav1.5 channel with improved efficacy and potency relative to ranolazine," *Bioorg. Med. Chem. Lett.* (2016) vol. 26, pp. 3207-3211.

PUBCHEM-CID 58763997 Create Date: Aug. 19, 2012 (14 pages).
PUBCHEM-CID 597467 Create Date: Mar. 27, 2005 (15 pages).
PUBCHEM-CID 82381512 Create Date: Oct. 20, 2014 (10 pages).
PUBCHEM-CID 89077556 Create Date: Feb. 13, 2015 (11 pages).
STN Chemical Structure Search Results (dated Apr. 14, 2019). (36 pages).
STN Chemical Structure Search Results (dated Apr. 2018). (55 pages).
STN Chemical Structure Search Results (dated Apr. 23, 2019). (45 pages).
STN Chemical Structure Search Results (dated Feb. 2018). (29 pages).
STN Chemical Structure Search Results (dated Jan. 15, 2020). (22 pages).
STN Chemical Structure Search Results (dated Jan. 2018). (23 pages).
STN Chemical Structure Search Results (dated Mar. 20, 2018). (264 pages).
STN Chemical Structure Search Results (dated Mar. 20, 2018). (83 pages).
STN Chemical Structure Search Results (dated Mar. 6, 2017). (480 pages).
STN Chemical Structure Search Results (dated Mar. 6, 2017). (511 pages).
STN Chemical Structure Search Results (dated May 18, 2016). (102 pages).
STN Chemical Structure Search Results (dated Nov. 1, 2017). (107 pages).
STN Chemical Structure Search Results (dated Nov. 21, 2017). (85 pages).
STN Chemical Structure Search Results (dated Nov. 3, 2017). (57 pages).
STN Chemical Structure Search Results (dated Nov. 6, 2017). (123 pages).
STN Chemical Structure Search Results (dated Nov. 6, 2017). (7 pages).
Wengert et al. "Prax330 reduces persistent and resurgent sodium channel currents and neuronal hyperexcitability of subiculum neurons in a mouse model of SCN8A epileptic encephalopathy," *Neuropharmacology* (2019) vol. 158, No. 107699, pp. 1-11.
Written Opinion of the International Searching Authority and International Search Report for PCT/US2017/063507 dated Mar. 29, 2019 (9 pages).
Written Opinion of the International Searching Authority and International Search Report for PCT/US2017/063533 dated Mar. 29, 2019 (10 pages).
Written Opinion of the International Searching Authority and International Search Report for PCT/US2017/063534 dated Mar. 28, 2019 (11 pages).
Written Opinion of the International Searching Authority and International Search Report for PCT/US2018/00224 dated Nov. 5, 2018 (8 pages).
Written Opinion of the International Searching Authority and International Search Report for PCT/US2018/018044 dated May 24, 2018 (10 pages).
Written Opinion of the International Searching Authority and International Search Report for PCT/US2018/026099 dated Aug. 10, 2018 (9 pages).
Written Opinion of the International Searching Authority and International Search Report for PCT/US2019/034653 dated Aug. 9, 2019 (9 pages).
Written Opinion of the International Searching Authority and International Search Report for PCT/US2019/053467 dated Jan. 14, 2020 (9 pages).
Zablocki et al. "Discovery of Dihydrobenzoxazepinone (GS-6615) Late Sodium Current Inhibitor (Late $I_{Na}i$), a Phase II Agent with Demonstrated Preclinical Anti-Ischemic and Antiarrhythmic Properties," *Journal of Medicinal Chemistry* (2016) vol. 59, pp. 9005-9017.
Berge et al., (1977). "Pharmaceutical salts," J. Pharmaceutical Sciences, 66(1):1-19.

(56) References Cited

OTHER PUBLICATIONS

Cannon, J. G., (1995). "Chapter Nineteen: Analog Design," Burger's Medicinal Chemistry and Drug Discovery, Fifth Edition, vol. I: Principles and Practice, Wiley-Interscience, pp. 783-802.

Dorwald, F. Z., (2005). "Side Reactions in Organic Synthesis," Wiley: VCH, Weinheim p. IX of Preface p. 1-15.

Fukaya et al., (2013). "Identification of a Novel Benzoxazolone Derivative as a Selective, Orally Active 18 kDa Translocator Protein (TSPO) Ligand," J. of Med. Chem., 56(20):8191-8195.

Hackam et al., (2006). "Translation of research evidence from animals to humans," JAMA, 296(14):1731-1732.

International Preliminary Report on Patentability for International Patent Application No. PCT/US2018/018044 filed on Feb. 13, 2018, 7 pages.

International Preliminary Report on Patentability for International Patent Application No. PCT/US2018/026099 filed on Apr. 4, 2018, 6 pages.

International Preliminary Report on Patentability for International Patent Application No. PCT/US2017/063507 filed on Nov. 28, 2017, 6 pages.

International Preliminary Report on Patentability for International Patent Application No. PCT/US2017/063534 filed on Nov. 28, 2017, 8 pages.

International Preliminary Report on Patentability for International Patent Application No. PCT/US2018/000224 filed on Aug. 15, 2018, 6 pages.

International Search Report and Written Opinion dated Feb. 25, 2021, for PCT Application No. PCT/US2020/062179 filed on Nov. 25, 2020, 7 pages.

Jordan et al., (2003). "Tamoxifen: a most unlikely pioneering medicine," Nat Rev Drug Discov., 2(3):205-213.

Venkatesh et al., (2000). "Role of the development scientist in compound lead selection and optimization," J Pharm Sci., 89(2):145-54.

Wilen et al., (1977). "Strategies in optical resolutions," Tetrahedron, 33(21):2725-2736.

Woodland et al., (2015). "Discovery of Inhibitors of Trypanosoma brucei by Phenotypic Screening of a Focused Protein Kinase Library," ChemMedChem, 10(11): 1809-1820.

Zaza et al., (2008). "Pathophysiology and pharmacology of the cardiac 'late sodium current'," Pharmacology & Therapeutics, 119(3):326-339.

\* cited by examiner

COMPOUNDS AND THEIR METHODS OF USE

CROSS-REFERENCE TO RELATED APPLICATIONS

The present application is a U.S. National Phase Application under 35 U.S.C. § 371 of International Application PCT/US2018/026099, filed Apr. 4, 2018, which claims priority under 35 U.S.C. § 119(e) to U.S. provisional patent application U.S.S.N. 62/481,463, filed Apr. 4, 2017.

BACKGROUND

Sodium ion (Na+) channels primarily open in a transient manner and are quickly inactivated, thereby generating a fast Na+ current to initiate the action potential. The late or persistent sodium current (INaL) is a sustained component of the fastNa+ current of cardiac myocytes and neurons. Many common neurological and cardiac conditions are associated with abnormal INaL enhancement, which contributes to the pathogenesis of both electrical and contractile dysfunction in mammals (see, e.g., *Pharmacol Ther* (2008) 119:326-339). Accordingly, pharmaceutical compounds that selectively modulate sodium channel activity, e.g., abnormal INaL, are useful in treating such disease states.

SUMMARY OF THE INVENTION

Described herein are fused heteroaryl compounds and compositions useful for preventing and/or treating a disease, disorder, or condition, e.g., a disease, disorder, or condition relating to aberrant function of a sodium ion channel, e.g., abnormal late sodium current (INaL). In one aspect, the present disclosure features compounds of Formula (I):

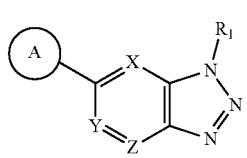
(I)

or a pharmaceutically acceptable salt thereof, wherein each of X, Y, and Z is independently N or $CR^2$; A is aryl or heteroaryl (e.g., a monocyclic 6-membered aryl or heteroaryl), wherein aryl and heteroaryl are optionally substituted with one or more (e.g., 1, 2, 3, or 4; e.g., 1, 2, or 3) $R^3$; $R^1$ is independently hydrogen, alkyl, alkenyl, alkynyl, carbocyclyl, heterocyclyl, aryl, or heteroaryl, wherein alkyl, alkenyl, alkynyl, carbocyclyl, heterocyclyl, aryl, and heteroaryl are optionally substituted with one or more (e.g., 1, 2, 3, or 4; e.g., 1, 2, or 3) $R^4$; $R^2$ is hydrogen, alkyl, or halogen; each $R^3$ is independently alkyl, halo, cyano, nitro, carbocyclyl, heterocyclyl, $—OR^c$, $—N(R^d)_2$, $—C(O)R^c$, $—C(O)OR^c$, or $—C(O)N(R^d)_2$, wherein alkyl, carbocyclyl, and heterocyclyl are optionally substituted with one or more (e.g., 1, 2, 3, or 4; e.g., 1, 2, or 3) $R^5$; each $R^4$ and $R^5$ is independently alkyl, halo, cyano, nitro, or $—OR^c$; each $R^c$ is independently hydrogen, alkyl, aryl, or heteroaryl, wherein alkyl, aryl, and heteroaryl is optionally substituted by one or more (e.g., 1, 2, 3, or 4; e.g., 1, 2, or 3) $R^6$; each $R^d$ is independently hydrogen or alkyl; and each $R^6$ is independently alkyl, carbocyclyl, heterocyclyl, halo, cyano, nitro, or —OH.

In one aspect, the present invention provides a compound of formula (II),

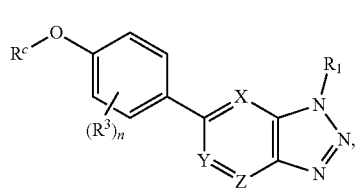
(II)

or a pharmaceutically acceptable salt thereof, wherein the variables are as defined herein.

In some embodiments, the present invention provides a compound of formula (II-a),

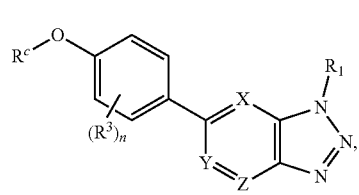
(II-a)

or a pharmaceutically acceptable salt thereof, wherein the variables are as defined herein.

In one aspect, the present invention provides a compound of formula (III),

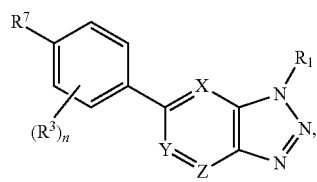
(III)

or a pharmaceutically acceptable salt thereof, wherein the variables are as defined herein.

In one aspect, the present invention provides a compound of formula (IV),

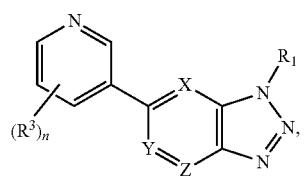
(IV)

or a pharmaceutically acceptable salt thereof, wherein the variables are as defined herein.

In some embodiments, the present invention provides a compound of formula (IV-a),

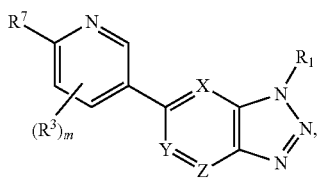

(IV-a)

or a pharmaceutically acceptable salt thereof, wherein the variables are as defined herein.

Other objects and advantages will become apparent to those skilled in the art from a consideration of the ensuing Detailed Description, Examples, and Claims.

DETAILED DESCRIPTION OF THE INVENTION

As generally described herein, the present invention provides compounds and compositions useful for preventing and/or treating a disease, disorder, or condition described herein, e.g., a disease, disorder, or condition relating to aberrant function of a sodium ion channel, such as abnormal late sodium current (INaL). Exemplary diseases, disorders, or conditions include a neurological disorder (e.g., epilepsy or an epilepsy syndrome, a neurodevelopmental disorder or a neuromuscular disorder), a psychiatric disorder, pain, or a gastrointestinal disorder.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compound described herein may also comprise one or more isotopic substitutions. For example, H may be in any isotopic form, including $^1$H, $^2$H (D or deuterium), and $^3$H (T or tritium); C may be in any isotopic form, including $^{12}$C, $^{13}$C, and $^{14}$C; O may be in any isotopic form, including $^{16}$O and $^{18}$O; and the like.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a radical of a straight-chain or branched saturated hydrocarbon group, e.g., having 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). Examples of $C_{1-6}$ alkyl groups include methyl, ethyl, propyl, isopropyl, butyl, isobutyl, pentyl, hexyl, and the like.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like.

As used herein, "alkylene," "alkenylene," and "alkynylene," refer to a divalent radical of an alkyl, alkenyl, and alkynyl group respectively. When a range or number of carbons is provided for a particular "alkylene," "alkenylene," or "alkynylene," group, it is understood that the range or number refers to the range or number of carbons in the linear carbon divalent chain. "Alkylene," "alkenylene," and "alkynylene," groups may be substituted or unsubstituted with one or more substituents as described herein.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl.

"Fused aryl" refers to an aryl having two of its ring carbon in common with a second aryl or heteroaryl ring or with a carbocyclyl or heterocyclyl ring.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

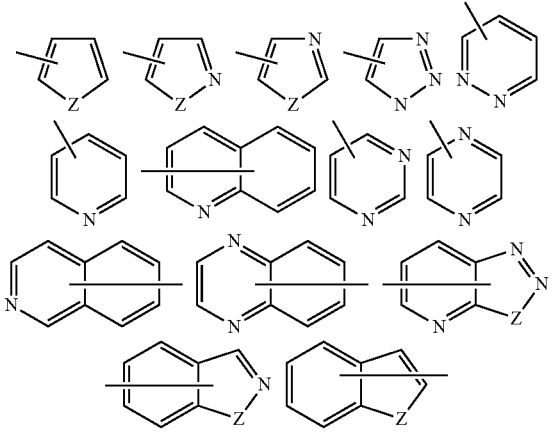

wherein each Z is selected from carbonyl, N, NR$^{65}$, O, and S; and R$^{65}$ is independently hydrogen, $C_1$-$C_8$ alkyl, $C_3$-$C_{10}$ carbocyclyl, 4-10 membered heterocyclyl, $C_6$-$C_{10}$ aryl, and 5-10 membered heteroaryl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, carbocyclyl, e.g., heterocyclyl, aryl, e.g. heteroaryl, cycloalkenyl, e.g. cycloheteroalkenyl, and the like having from 1 to 5, and particularly from 1 to 3 heteroatoms.

"Cyano" refers to the radical —CN.

"Halo" or "halogen" refers to fluoro (F), chloro (Cl), bromo (Br), and iodo (I). In certain embodiments, the halo group is either fluoro or chloro.

"Haloalkyl" refers to an alkyl group substituted with one or more halogen atoms.

"Nitro" refers to the radical —NO$_2$.

In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, SO$_4^{-2}$ sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quaternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

These and other exemplary substituents are described in more detail in the Detailed Description, Examples, and Claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+$ ($C_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

Compounds

In one aspect, the present invention features a compound of Formula (I):

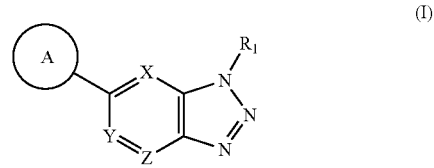

(I)

or a pharmaceutically acceptable salt thereof, wherein each of X, Y, and Z is independently N or $CR^2$; A is aryl or heteroaryl (e.g., a monocyclic 6-membered aryl or heteroaryl), wherein aryl and heteroaryl are optionally substituted with one or more (e.g., 1, 2, 3, or 4; e.g., 1, 2, or 3) $R^3$; $R^1$ is independently hydrogen, alkyl, alkenyl, alkynyl, carbocyclyl, heterocyclyl, aryl, or heteroaryl, wherein alkyl, alkenyl, alkynyl, carbocyclyl, heterocyclyl, aryl, and heteroaryl are optionally substituted with one or more $R^4$; $R^2$ is hydrogen, alkyl or halogen; each $R^3$ is independently alkyl, halo, cyano, nitro, carbocyclyl, heterocyclyl, —$OR^c$, —$N(R^d)_2$, —$C(O)R^c$, —$C(O)OR^c$, or —$C(O)N(R^d)_2$, wherein alkyl, carbocyclyl, and heterocyclyl are optionally substituted with one or more (e.g., 1, 2, 3, or 4; e.g., 1, 2, or 3) $R^5$; each $R^4$ and $R^5$ is independently alkyl, halo, cyano, nitro, or —$OR^c$; each $R^c$ is independently hydrogen, alkyl, aryl, or heteroaryl, wherein alkyl, aryl, and heteroaryl is optionally substituted by one or more (e.g., 1, 2, 3, or 4; e.g., 1, 2, or 3) $R^6$; each $R^d$ is independently hydrogen or alkyl; and each $R^6$ is independently alkyl, carbocyclyl, heterocyclyl, halo, cyano, nitro, or —OH.

In some embodiments, X is N. In some embodiments, X is CR². In some embodiments, R² is hydrogen. In some embodiments, X is CH.

In some embodiments, Y is CR². In some embodiments, R² is hydrogen. In some embodiments, Y is CH.

In some embodiments, Z is N. In some embodiments, Z is CR². In some embodiments, R² is hydrogen. In some embodiments, Z is CH.

In some embodiments, each of X, Y, and Z is independently CR² (e.g., CH). In some embodiments, X is N and each of Y and Z is independently CR² (e.g., CH). In some embodiments, Z is N and each of X and Y is independently CR² (e.g., CH).

In some embodiments, $R^1$ is alkyl. In some embodiments, $R^1$ is substituted alkyl (e.g., substituted $C_1$-$C_6$ alkyl). In some embodiments, $R^1$ is alkyl (e.g., $C_1$-$C_6$ alkyl, e.g., $C_2$ alkyl) substituted with one or more (e.g., 1, 2, 3, or 4; e.g., 1, 2, or 3) $R^4$. In some embodiments, $R^4$ is halo (e.g., fluoro). In some embodiments, $R^1$ is —CH₂CF₃.

In some embodiments, A is monocyclic aryl (e.g., phenyl). In some embodiments, A is a 6-membered aryl (e.g., phenyl). In some embodiments, A is phenyl.

In some embodiments, A is substituted by one or more (e.g., 1, 2, 3, or 4; e.g., 1, 2, or 3) $R^3$. In some embodiments, A is phenyl substituted by $R^3$ in the para position.

In some embodiments, each $R^3$ is independently alkyl, carbocyclyl, or —OR$^c$. In some embodiments, $R^3$ is alkyl (e.g., $C_1$-$C_6$ alkyl). In some embodiments, $R^3$ is unsubstituted alkyl (e.g., unsubstituted $C_1$-$C_6$ alkyl) or substituted alkyl (e.g., substituted $C_1$-$C_6$ alkyl). In some embodiments, $R^3$ is alkyl (e.g., $C_1$-$C_6$ alkyl, e.g., $C_2$ alkyl) substituted with one or more (e.g., 1, 2, 3, or 4; e.g., 1, 2, or 3) $R^5$ (e.g., —OR$^c$). In some embodiments, $R^3$ is —CH₂CH₂OCH₃.

In some embodiments, $R^3$ is —OR$^c$. In some embodiments, $R^3$ is —OR$^c$, wherein R$^c$ is alkyl ($C_1$-$C_6$ alkyl). In some embodiments, $R^3$ is unsubstituted alkyl (e.g., unsubstituted $C_1$-$C_6$ alkyl) or substituted alkyl (e.g., substituted $C_1$-$C_6$ alkyl). In some embodiments, R$^c$ is alkyl (e.g., $C_1$-$C_6$ alkyl, e.g., $C_1$ alkyl), substituted with one or more (e.g., 1, 2, 3, or 4; e.g., 1, 2, or 3) $R^6$. In some embodiments, $R^6$ is halo (e.g., fluoro). In some embodiments, $R^3$ is —OCF₃. In some embodiments, $R^3$ is —OCF₃ in the para position.

In some embodiments, $R^3$ is carbocyclyl. In some embodiments, $R^3$ is $C_3$-$C_6$ carbocyclyl (e.g., cycopropyl). In some embodiments, $R^3$ is cyclopropyl (e.g., unsubstituted cycopropyl or substituted cyclopropyl). In some embodiments, $R^3$ is cyclopropyl substituted with one or more (e.g., 1, 2, 3, or 4; e.g., 1, 2, or 3) $R^5$ (e.g., cyano).

In another aspect, provided is a compound of Formula (I-a):

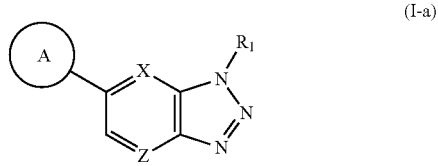

(I-a)

or a pharmaceutically acceptable salt thereof, wherein each of X and Z is independently N or CR²; A is aryl or heteroaryl (e.g., a monocyclic 6-membered aryl or heteroaryl), wherein aryl and heteroaryl are optionally substituted with one or more (e.g., 1, 2, 3, or 4; e.g., 1, 2, or 3) $R^3$; $R^1$ is independently hydrogen, alkyl, alkenyl, alkynyl, carbocyclyl, heterocyclyl, aryl, or heteroaryl, wherein alkyl, alkenyl, alkynyl, carbocyclyl, heterocyclyl, aryl, and heteroaryl are optionally substituted with one or more (e.g., 1, 2, 3, or 4; e.g., 1, 2, or 3) $R^4$; $R^2$ is hydrogen, alkyl or halogen; each $R^3$ is independently alkyl, halo, cyano, nitro, carbocyclyl, heterocyclyl, —OR$^c$, —N(R$^d$)₂, —C(O)R$^c$, —C(O)OR$^c$, or —C(O)N(R$^d$)₂, wherein alkyl, carbocyclyl, and heterocyclyl are optionally substituted with one or more (e.g., 1, 2, 3, or 4; e.g., 1, 2, or 3) $R^5$; each $R^4$ and $R^5$ is independently alkyl, halo, cyano, nitro, or —OR$^c$; each R$^c$ is independently hydrogen, alkyl, aryl, or heteroaryl, wherein alkyl, aryl, and heteroaryl is optionally substituted by one or more (e.g., 1, 2, 3, or 4; e.g., 1, 2, or 3) $R^6$; each R$^d$ is independently hydrogen or alkyl; and each $R^6$ is independently alkyl, carbocyclyl, heterocyclyl, halo, cyano, nitro, or —OH.

In some embodiments, X is N. In some embodiments, X is CR². In some embodiments, R² is hydrogen. In some embodiments, X is CH.

In some embodiments, Z is N. In some embodiments, Z is CR². In some embodiments, R² is hydrogen. In some embodiments, Z is CH.

In some embodiments, each of X and Z is independently CR² (e.g., CH). In some embodiments, X is N and Z is CR² (e.g., CH). In some embodiments, each of X and Z is independently N.

In some embodiments, $R^1$ is alkyl. In some embodiments, $R^1$ is substituted alkyl (e.g., substituted $C_1$-$C_6$ alkyl). In some embodiments, $R^1$ is alkyl (e.g., $C_1$-$C_6$ alkyl, e.g., $C_2$ alkyl) substituted with one or more (e.g., 1, 2, 3, or 4; e.g., 1, 2, or 3) $R^4$. In some embodiments, $R^4$ is halo (e.g., fluoro). In some embodiments, $R^1$ is —CH₂CF₃.

In some embodiments, A is monocyclic aryl (e.g., phenyl). In some embodiments, A is a 6-membered aryl (e.g., phenyl). In some embodiments, A is phenyl.

In some embodiments, A is substituted by one or more (e.g., 1, 2, 3, or 4; e.g., 1, 2, or 3) $R^3$. In some embodiments, A is phenyl substituted by $R^3$ in the para position.

In some embodiments, each $R^3$ is independently alkyl, carbocyclyl, or —OR$^c$. In some embodiments, $R^3$ is alkyl (e.g., $C_1$-$C_6$ alkyl). In some embodiments, $R^3$ is unsubstituted alkyl (e.g., unsubstituted $C_1$-$C_6$ alkyl) or substituted alkyl (e.g., substituted $C_1$-$C_6$ alkyl). In some embodiments, $R^3$ is alkyl (e.g., $C_1$-$C_6$ alkyl, e.g., $C_2$ alkyl) substituted with one or more (e.g., 1, 2, 3, or 4; e.g., 1, 2, or 3) $R^5$ (e.g., —OR$^c$). In some embodiments, $R^3$ is —CH₂CH₂OCH₃.

In some embodiments, $R^3$ is —OR$^c$. In some embodiments, $R^3$ is —OR$^c$, wherein R$^c$ is alkyl ($C_1$-$C_6$ alkyl). In some embodiments, $R^3$ is unsubstituted alkyl (e.g., unsubstituted $C_1$-$C_6$ alkyl) or substituted alkyl (e.g., substituted $C_1$-$C_6$ alkyl). In some embodiments, R$^c$ is alkyl (e.g., $C_1$-$C_1$, alkyl, e.g., $C_1$ alkyl), substituted with one or more (e.g., 1, 2, 3, or 4; e.g., 1, 2, or 3) $R^6$. In some embodiments, $R^6$ is halo (e.g., fluoro). In some embodiments, $R^3$ is —OCF₃. In some embodiments, $R^3$ is —OCF₃ in the para position.

In some embodiments, $R^3$ is carbocyclyl. In some embodiments, $R^3$ is $C_3$-$C_6$ carbocyclyl (e.g., cycopropyl). In some embodiments, $R^3$ is cyclopropyl (e.g., unsubstituted cycopropyl or substituted cyclopropyl). In some embodiments, $R^3$ is cyclopropyl substituted with one or more (e.g., 1, 2, 3, or 4; e.g., 1, 2, or 3) $R^5$ (e.g., cyano).

In another aspect, provided is a compound of Formula (I-b):

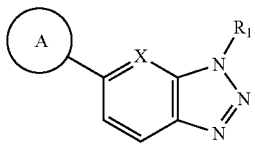

(I-b)

or a pharmaceutically acceptable salt thereof, wherein X is independently N or $CR^2$; A is aryl or heteroaryl (e.g., a monocyclic 6-membered aryl or heteroaryl), wherein aryl and heteroaryl are optionally substituted with one or more (e.g., 1, 2, 3, or 4; e.g., 1, 2, or 3) $R^3$; $R^1$ is independently hydrogen, alkyl, alkenyl, alkynyl, carbocyclyl, heterocyclyl, aryl, or heteroaryl, wherein alkyl, alkenyl, alkynyl, carbocyclyl, heterocyclyl, aryl, and heteroaryl are optionally substituted with one or more (e.g., 1, 2, 3, or 4; e.g., 1, 2, or 3) $R^4$; $R^2$ is hydrogen, alkyl or halogen; each $R^3$ is independently alkyl, halo, cyano, nitro, carbocyclyl, heterocyclyl, —$OR^c$, —$N(R^d)_2$, —$C(O)R^c$, —$C(O)OR^c$, or —$C(O)N(R^d)_2$, wherein alkyl, carbocyclyl, and heterocyclyl are optionally substituted with one or more (e.g., 1, 2, 3, or 4; e.g., 1, 2, or 3) $R^5$; each $R^4$ and $R^5$ is independently alkyl, halo, cyano, nitro, or —$OR^c$; each $R^c$ is independently hydrogen, alkyl, aryl, or heteroaryl, wherein alkyl, aryl, and heteroaryl is optionally substituted by one or more (e.g., 1, 2, 3, or 4; e.g., 1, 2, or 3) $R^6$; each $R^d$ is independently hydrogen or alkyl; and each $R^6$ is independently alkyl, carbocyclyl, heterocyclyl, halo, cyano, nitro, or —OH.

In some embodiments, X is N. In some embodiments, X is $CR^2$. In some embodiments, $R^2$ is hydrogen. In some embodiments, X is CH.

In some embodiments, $R^1$ is alkyl. In some embodiments, $R^1$ is substituted alkyl (e.g., substituted $C_1$-$C_6$ alkyl). In some embodiments, $R^1$ is alkyl (e.g., $C_1$-$C_6$ alkyl, e.g., $C_2$ alkyl) substituted with one or more (e.g., 1, 2, 3, or 4; e.g., 1, 2, or 3) $R^4$. In some embodiments, $R^4$ is halo (e.g., fluoro). In some embodiments, $R^1$ is —$CH_2CF_3$.

In some embodiments, A is monocyclic aryl (e.g., phenyl). In some embodiments, A is a 6-membered aryl (e.g., phenyl). In some embodiments, A is phenyl.

In some embodiments, A is substituted by one or more (e.g., 1, 2, 3, or 4; e.g., 1, 2, or 3) $R^3$. In some embodiments, A is phenyl substituted by $R^3$ in the para position.

In some embodiments, each $R^3$ is independently alkyl, carbocyclyl, or —$OR^c$. In some embodiments, $R^3$ is alkyl (e.g., $C_1$-$C_6$ alkyl). In some embodiments, $R^3$ is unsubstituted alkyl (e.g., unsubstituted $C_1$-$C_6$ alkyl) or substituted alkyl (e.g., substituted $C_1$-$C_6$ alkyl). In some embodiments, $R^3$ is alkyl (e.g., $C_1$-$C_6$ alkyl, e.g., $C_2$ alkyl) substituted with one or more (e.g., 1, 2, 3, or 4; e.g., 1, 2, or 3) $R^5$ (e.g., —$OR^c$). In some embodiments, $R^3$ is —$CH_2CH_2OCH_3$.

In some embodiments, $R^3$ is —$OR^c$. In some embodiments, $R^3$ is —$OR^c$, wherein $R^c$ is alkyl ($C_1$-$C_6$ alkyl). In some embodiments, $R^3$ is unsubstituted alkyl (e.g., unsubstituted $C_1$-$C_6$ alkyl) or substituted alkyl (e.g., substituted $C_1$-$C_6$ alkyl). In some embodiments, $R^c$ is alkyl (e.g., $C_1$-$C_6$ alkyl, e.g., $C_1$ alkyl), substituted with one or more (e.g., 1, 2, 3, or 4; e.g., 1, 2, or 3) $R^6$. In some embodiments, $R^6$ is halo (e.g., fluoro). In some embodiments, $R^3$ is —$OCF_3$. In some embodiments, $R^3$ is —$OCF_3$ in the para position.

In some embodiments, $R^3$ is carbocyclyl. In some embodiments, $R^3$ is $C_3$-$C_6$ carbocyclyl (e.g., cycopropyl). In some embodiments, $R^3$ is cyclopropyl (e.g., unsubstituted cycopropyl or substituted cyclopropyl). In some embodiments, $R^3$ is cyclopropyl substituted with one or more (e.g., 1, 2, 3, or 4; e.g., 1, 2, or 3) $R^5$ (e.g., cyano).

In another aspect, provided is a compound of Formula (I-c):

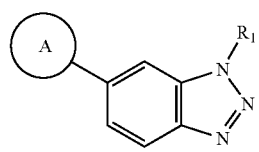

(I-c)

or a pharmaceutically acceptable salt thereof, wherein A is aryl or heteroaryl (e.g., a monocyclic 6-membered aryl or heteroaryl), wherein aryl and heteroaryl are optionally substituted with one or more (e.g., 1, 2, 3, or 4; e.g., 1, 2, or 3) $R^3$; $R^1$ is independently hydrogen, alkyl, alkenyl, alkynyl, carbocyclyl, heterocyclyl, aryl, or heteroaryl, wherein alkyl, alkenyl, alkynyl, carbocyclyl, heterocyclyl, aryl, and heteroaryl are optionally substituted with one or more (e.g., 1, 2, 3, or 4; e.g., 1, 2, or 3) $R^4$; $R^2$ is hydrogen, alkyl or halogen; each $R^3$ is independently alkyl, halo, cyano, nitro, carbocyclyl, heterocyclyl, —$OR^c$, —$N(R^d)_2$, —$C(O)R^c$, —$C(O)OR^c$, or —$C(O)N(R^d)_2$ wherein alkyl, carbocyclyl, and heterocyclyl are optionally substituted with one or more (e.g., 1, 2, 3, or 4; e.g., 1, 2, or 3) $R^5$; each $R^4$ and $R^5$ is independently alkyl, halo, cyano, nitro, or —$OR^c$; each $R^c$ is independently hydrogen, alkyl, aryl, or heteroaryl, wherein alkyl, aryl, and heteroaryl is optionally substituted by one or more (e.g., 1, 2, 3, or 4; e.g., 1, 2, or 3) $R^6$; each $R^d$ is independently hydrogen or alkyl; and each $R^6$ is independently alkyl, carbocyclyl, heterocyclyl, halo, cyano, nitro, or —OH.

In some embodiments, $R^1$ is alkyl. In some embodiments, $R^1$ is substituted alkyl (e.g., substituted $C_1$-$C_6$ alkyl). In some embodiments, $R^1$ is alkyl (e.g., $C_1$-$C_6$ alkyl, e.g., $C_2$ alkyl) substituted with one or more (e.g., 1, 2, 3, or 4; e.g., 1, 2, or 3) $R^4$. In some embodiments, $R^4$ is halo (e.g., fluoro). In some embodiments, $R^1$ is —$CH_2CF_3$.

In some embodiments, A is monocyclic aryl (e.g., phenyl). In some embodiments, A is a 6-membered aryl (e.g., phenyl). In some embodiments, A is phenyl.

In some embodiments, A is substituted by one or more (e.g., 1, 2, 3, or 4; e.g., 1, 2, or 3) $R^3$. In some embodiments, A is phenyl substituted by $R^3$ in the para position.

In some embodiments, each $R^3$ is independently alkyl, carbocyclyl, or —$OR^c$. In some embodiments, $R^3$ is alkyl (e.g., $C_1$-$C_6$ alkyl). In some embodiments, $R^3$ is unsubstituted alkyl (e.g., unsubstituted $C_1$-$C_6$ alkyl) or substituted alkyl (e.g., substituted $C_1$-$C_6$ alkyl). In some embodiments, $R^3$ is alkyl (e.g., $C_1$-$C_6$ alkyl, e.g., $C_2$ alkyl) substituted with one or more (e.g., 1, 2, 3, or 4; e.g., 1, 2, or 3) $R^5$ (e.g., —$OR^c$). In some embodiments, $R^3$ is —$CH_2CH_2OCH_3$.

In some embodiments, $R^3$ is —$OR^c$. In some embodiments, $R^3$ is —$OR^c$, wherein $R^c$ is alkyl ($C_1$-$C_6$ alkyl). In some embodiments, $R^3$ is unsubstituted alkyl (e.g., unsubstituted $C_1$-$C_6$ alkyl) or substituted alkyl (e.g., substituted $C_1$-$C_6$ alkyl). In some embodiments, $R^c$ is alkyl (e.g., $C_1$-$C_1$ alkyl, e.g., $C_1$ alkyl), substituted with one or more (e.g., 1, 2, 3, or 4; e.g., 1, 2, or 3) $R^6$. In some embodiments, $R^6$ is halo (e.g., fluoro). In some embodiments, $R^3$ is —$OCF_3$. In some embodiments, $R^3$ is —$OCF_3$ in the para position.

In some embodiments, $R^3$ is carbocyclyl. In some embodiments, $R^3$ is $C_3$-$C_6$ carbocyclyl (e.g., cycopropyl). In some embodiments, $R^3$ is cyclopropyl (e.g., unsubstituted cycopropyl or substituted cyclopropyl). In some embodiments, $R^3$ is cyclopropyl substituted with one or more (e.g., 1, 2, 3, or 4; e.g., 1, 2, or 3) $R^5$ (e.g., cyano).

In one aspect, the present invention provides a compound of Formula (II):

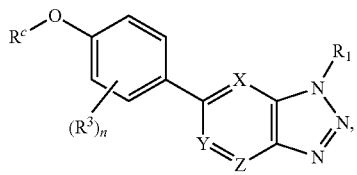
(II)

or a pharmaceutically acceptable salt thereof, wherein:
each of X, Y, and Z is independently N or $CR^2$;
$R^1$ is independently hydrogen, alkyl, alkenyl, alkynyl, carbocyclyl, heterocyclyl, aryl, or heteroaryl, wherein alkyl, alkenyl, alkynyl, carbocyclyl, heterocyclyl, aryl, and heteroaryl are optionally substituted with one or more (e.g., 1, 2, 3, or 4; e.g., 1, 2, or 3) $R^4$;
$R^2$ is hydrogen, alkyl or halogen;
each $R^3$ is independently alkyl, halo, cyano, nitro, carbocyclyl, heterocyclyl, —$OR^c$, —$N(R^d)_2$, —$C(O)R^c$, —$C(O)OR^c$, or —$C(O)N(R^d)_2$, wherein alkyl, carbocyclyl, and heterocyclyl are optionally substituted with one or more (e.g., 1, 2, 3, or 4; e.g., 1, 2, or 3) $R^5$;
each $R^4$ and $R^5$ is independently alkyl, halo, cyano, nitro, 5 or 6-membered heteroaryl, or —$OR^c$, wherein the 5 or 6 membered heteroaryl is optionally substituted with alkyl;
each $R^c$ is independently hydrogen, alkyl, aryl, carbocyclyl, or heteroaryl, wherein alkyl, aryl, carbocyclyl, and heteroaryl is optionally substituted by one or more (e.g., 1, 2, 3, or 4; e.g., 1, 2, or 3) $R^6$;
each $R^d$ is independently hydrogen or alkyl;
each $R^6$ is independently alkyl, carbocyclyl, heterocyclyl, halo, cyano, nitro, or —OH, and
n is 0, 1, 2, or 3;
wherein the compound is not a compound selected from the group consisting of:

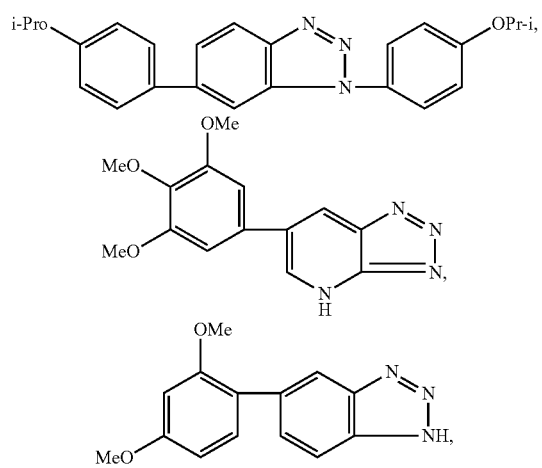

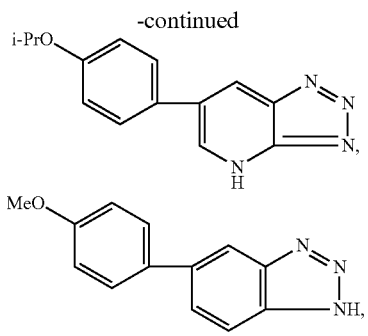

or a pharmaceutically acceptable salt thereof.

In some embodiments, the compound is a compound of Formula (II-a):

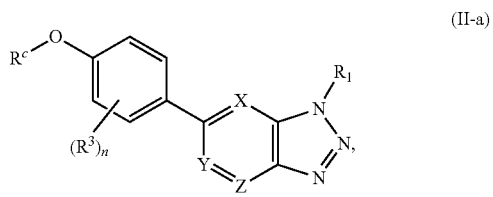
(II-a)

or a pharmaceutically acceptable salt thereof, wherein:
each of X, Y, and Z is independently N or $CR^2$;
$R^1$ is independently alkyl, alkenyl, alkynyl, carbocyclyl, heterocyclyl, or heteroaryl, wherein alkyl, alkenyl, alkynyl, carbocyclyl, heterocyclyl, aryl, and heteroaryl are optionally substituted with one or more (e.g., 1, 2, 3, or 4; e.g., 1, 2, or 3) $R^4$;
$R^2$ is hydrogen, alkyl or halogen;
each $R^3$ is independently alkyl, halo, cyano, nitro, carbocyclyl, heterocyclyl, —$OR^c$, —$N(R^d)_2$, —$C(O)R^c$, —$C(O)OR^c$, or —$C(O)N(R^d)_2$, wherein alkyl, carbocyclyl, and heterocyclyl are optionally substituted with one or more (e.g., 1, 2, 3, or 4; e.g., 1, 2, or 3) $R^5$;
each $R^4$ and $R^5$ is independently alkyl, halo, cyano, nitro, 5 or 6-membered heteroaryl, or —$OR^c$, wherein the 5 or 6 membered heteroaryl is optionally substituted with alkyl;
each $R^c$ is independently hydrogen, alkyl, aryl, carbocyclyl, or heteroaryl, wherein alkyl, aryl, carbocyclyl, and heteroaryl is optionally substituted by one or more (e.g., 1, 2, 3, or 4; e.g., 1, 2, or 3) $R^6$;
each $R^d$ is independently hydrogen or alkyl;
each $R^6$ is independently alkyl, carbocyclyl, heterocyclyl, halo, cyano, nitro, or —OH, and
n is 0, 1, 2, or 3.

In some embodiments, X is N, and Y and Z are $CR^2$.
In some embodiments, Y is N, and X and Z are $CR^2$.
In some embodiments, Z is N, and Y and X are $CR^2$.
In some embodiments, X and Z are N, and Y is $CR^2$.
In some embodiments, X and Y are N, and Z is $CR^2$.
In some embodiments, Z and Y are N, and X is $CR^2$.
In some embodiments, $R^2$ is hydrogen.
In some embodiments, $R^1$ is hydrogen or alkyl optionally substituted with 1, 2, or 3 of $R^4$.
In some embodiments, $R^1$ is alkyl optionally substituted with 1, 2, or 3 of $R^4$.
In some embodiments, $R^3$ is hydrogen.
In some embodiments, $R^3$ is alkyl or —$OR^c$, wherein alkyl is optionally substituted with $R^5$.

In some embodiments, R⁴ is halogen or 5 or 6-membered heteroaryl, wherein the 5 or 6 membered heteroaryl is optionally substituted with alkyl.

In some embodiments, R⁴ is halogen.

In some embodiments, R⁵ is cyano or —OR$^c$.

In some embodiments, R⁵ is —OR$^c$.

In some embodiments, R$^c$ is alkyl or carbocyclyl, wherein the alkyl or carbocyclyl is optionally substituted with 1, 2, or 3 of R⁶.

In some embodiments, R⁶ is halogen.

In some embodiments, n is 0 or 1.

In some embodiments, the compound is selected from the group consisting of:

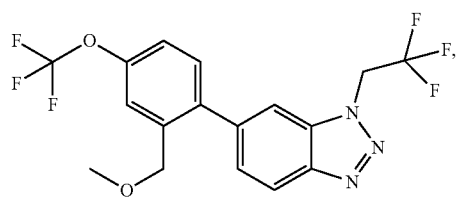
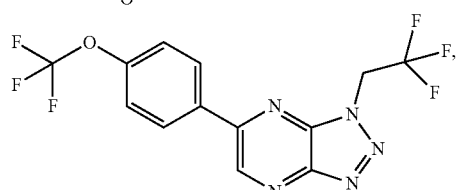
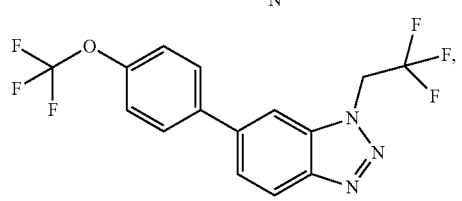
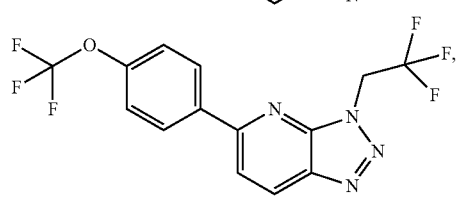
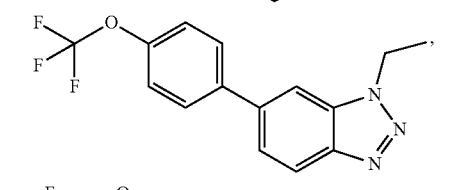
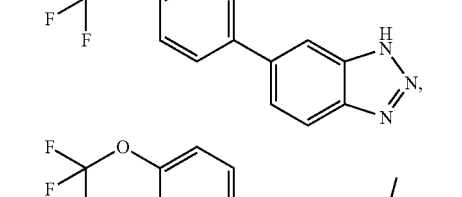
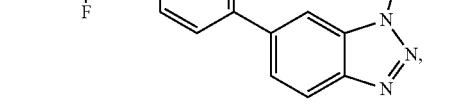

-continued

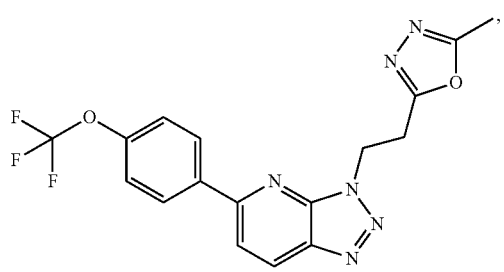
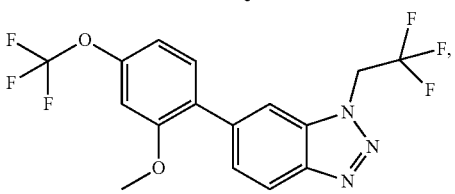
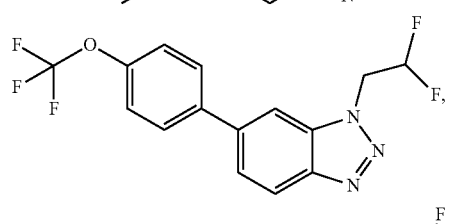
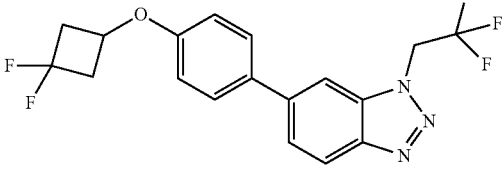
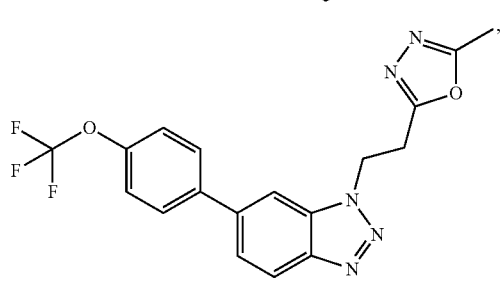
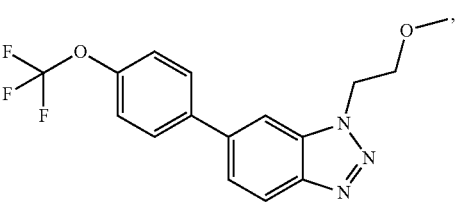
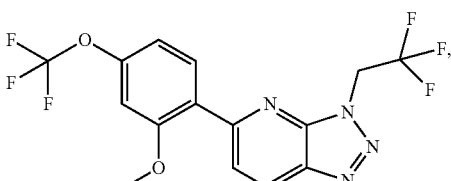
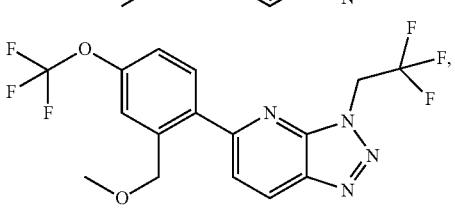

-continued

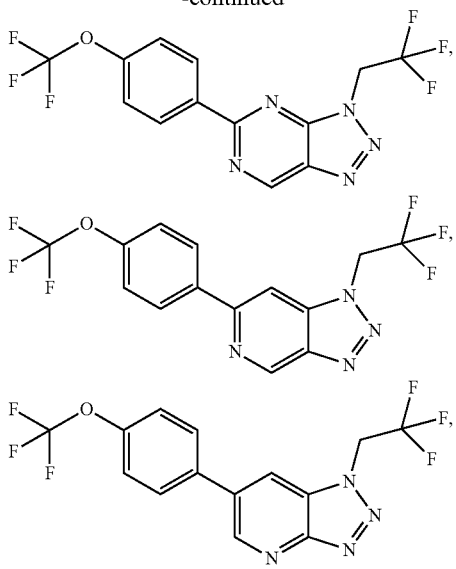

or a pharmaceutically acceptable salt thereof.

In one aspect, the present invention provides a compound of Formula (III):

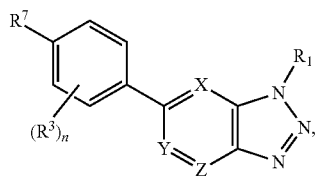

(III)

or a pharmaceutically acceptable salt thereof, wherein:
each of X, Y, and Z is independently N or $CR^2$;
$R^1$ is independently hydrogen, alkyl, alkenyl, alkynyl, carbocyclyl, heterocyclyl, aryl, or heteroaryl, wherein alkyl, alkenyl, alkynyl, carbocyclyl, heterocyclyl, aryl, and heteroaryl are optionally substituted with one or more (e.g., 1, 2, 3, or 4; e.g., 1, 2, or 3) $R^4$;
$R^2$ is hydrogen, alkyl or halogen;
$R^7$ is carbocyclyl optionally substituted with one or more (e.g., 1, 2, 3, or 4; e.g., 1, 2, or 3) $R^5$;
each $R^3$ is independently alkyl, halo, cyano, nitro, carbocyclyl, heterocyclyl, —$OR^c$, —$N(R^d)_2$, —$C(O)R^c$, —$C(O)OR^c$, or —$C(O)N(R^d)_2$, wherein alkyl, carbocyclyl, and heterocyclyl are optionally substituted with one or more (e.g., 1, 2, 3, or 4; e.g., 1, 2, or 3) $R^5$;
each $R^4$ and $R^5$ is independently alkyl, halo, cyano, nitro, 5 or 6-membered heteroaryl, or —$OR^c$, wherein the 5 or 6 membered heteroaryl is optionally substituted with alkyl;
each $R^c$ is independently hydrogen, alkyl, aryl, carbocyclyl, or heteroaryl, wherein alkyl, aryl, carbocyclyl, and heterocyclyl is optionally substituted by one or more (e.g., 1, 2, 3, or 4; e.g., 1, 2, or 3) $R^6$;
each $R^d$ is independently hydrogen or alkyl;
each $R^6$ is independently alkyl, carbocyclyl, heterocyclyl, halo, cyano, nitro, or —OH, and
n is 0, 1, 2, or 3.

In some embodiments, X is N, and Y and Z are $CR^2$.
In some embodiments, Y is N, and X and Z are $CR^2$.
In some embodiments, Z is N, and Y and X are $CR^2$.

In some embodiments, X and Z are N, and Y is $CR^2$.
In some embodiments, X and Y are N, and Z is $CR^2$.
In some embodiments, Z and Y are N, and X is $CR^2$.
In some embodiments, $R^2$ is hydrogen.
In some embodiments, $R^1$ is hydrogen or alkyl optionally substituted with 1, 2, or 3 of $R^4$.
In some embodiments, $R^1$ is alkyl optionally substituted with 1, 2, or 3 of $R^4$.
In some embodiments, $R^3$ is hydrogen.
In some embodiments, $R^3$ is alkyl or —$OR^c$, wherein alkyl is optionally substituted with $R^5$.
In some embodiments, $R^4$ is halogen or 5 or 6-membered heteroaryl, wherein the 5 or 6 membered heteroaryl is optionally substituted with alkyl.
In some embodiments, $R^4$ is halogen.
In some embodiments, $R^5$ is cyano or —$OR^c$.
In some embodiments, $R^5$ is cyano.
In some embodiments, $R^c$ is alkyl or carbocyclyl, wherein the alkyl or carbocyclyl is optionally substituted with 1, 2, or 3 of $R^6$.
In some embodiments, $R^6$ is halogen.
In some embodiments, n is 0 or 1.
In some embodiments, the compound is:

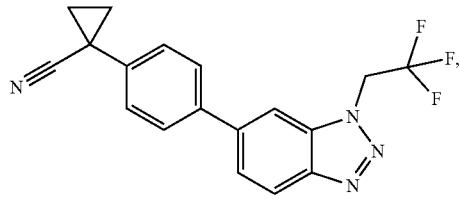 [SMILES: N#CC1(c2ccc(-c3ccc4nnn(CC(F)(F)F)c4c3)cc2)CC1]

or a pharmaceutically acceptable salt thereof.

In one aspect, the present invention provides a compound of Formula (IV):

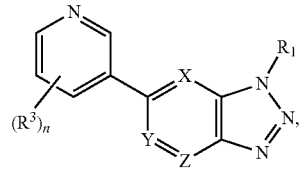

(IV)

or a pharmaceutically acceptable salt thereof, wherein:
each of X, Y, and Z is independently N or $CR^2$;
$R^1$ is independently hydrogen, alkyl, alkenyl, alkynyl, carbocyclyl, heterocyclyl, aryl, or heteroaryl, wherein alkyl, alkenyl, alkynyl, carbocyclyl, heterocyclyl, aryl, and heteroaryl are optionally substituted with one or more (e.g., 1, 2, 3, or 4; e.g., 1, 2, or 3) $R^4$;
$R^2$ is hydrogen, alkyl or halogen;
each $R^3$ is independently alkyl, halo, cyano, nitro, carbocyclyl, heterocyclyl, —$OR^c$, —$N(R^d)_2$, —$C(O)R^c$, —$C(O)OR^c$, or —$C(O)N(R^d)_2$, wherein alkyl, carbocyclyl, and heterocyclyl are optionally substituted with one or more (e.g., 1, 2, 3, or 4; e.g., 1, 2, or 3) $R^5$;
each $R^4$ and $R^5$ is independently alkyl, halo, cyano, nitro, 5 or 6-membered heteroaryl, or —$OR^c$, wherein the 5 or 6 membered heteroaryl is optionally substituted with alkyl;
each $R^c$ is independently hydrogen, alkyl, aryl, carbocyclyl, or heteroaryl, wherein alkyl, aryl, carbocyclyl, and heteroaryl is optionally substituted by one or more (e.g., 1, 2, 3, or 4; e.g., 1, 2, or 3) R⁶;
each R^d is independently hydrogen or alkyl;
each R⁶ is independently alkyl, carbocyclyl, heterocyclyl, halo, cyano, nitro, or —OH, and
n is 0, 1, 2, or 3;
wherein the compound is not a compound selected from the group consisting of:

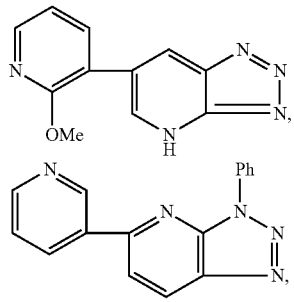

or a pharmaceutically acceptable salt thereof.

In some embodiments, the compound is a compound of Formula (IV-a):

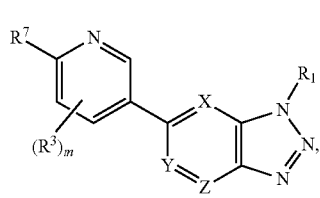

or a pharmaceutically acceptable salt thereof, wherein:
each of X, Y, and Z is independently N or CR²;
R¹ is independently alkyl, alkenyl, alkynyl, carbocyclyl, heterocyclyl, aryl, or heteroaryl, wherein alkyl, alkenyl, alkynyl, carbocyclyl, heterocyclyl, aryl, and heteroaryl are optionally substituted with one or more (e.g., 1, 2, 3, or 4; e.g., 1, 2, or 3) R⁴;
R² is hydrogen, alkyl or halogen;
R⁷ and each R³ are independently, for each occurrence, alkyl, halo, cyano, nitro, carbocyclyl, heterocyclyl, —OR^c, —N(R^d)₂, —C(O)R^c, —C(O)OR^c, or —C(O)N(R^d)₂, wherein alkyl, carbocyclyl, and heterocyclyl are optionally substituted with one or more (e.g., 1, 2, 3, or 4; e.g., 1, 2, or 3) R⁵;
each R⁴ and R⁵ is independently alkyl, halo, cyano, nitro, 5 or 6-membered heteroaryl, or —OR^c, wherein the 5 or 6 membered heteroaryl is optionally substituted with alkyl;
each R^c is independently hydrogen, alkyl, aryl, carbocyclyl, or heteroaryl, wherein alkyl, aryl, carbocyclyl, and heteroaryl is optionally substituted by one or more (e.g., 1, 2, 3, or 4; e.g., 1, 2, or 3) R⁶;
each R^d is independently hydrogen or alkyl;
each R⁶ is independently alkyl, carbocyclyl, heterocyclyl, halo, cyano, nitro, or —OH, and
m is 0, 1, or 2.

In some embodiments, X is N, and Y and Z are CR².
In some embodiments, Y is N, and X and Z are CR².
In some embodiments, Z is N, and Y and X are CR².
In some embodiments, X and Z are N, and Y is CR².
In some embodiments, X and Y are N, and Z is CR².
In some embodiments, Z and Y are N, and X is CR².
In some embodiments, R² is hydrogen.
In some embodiments, R¹ is hydrogen or alkyl optionally substituted with 1, 2, or 3 of R⁴.
In some embodiments, R¹ is alkyl optionally substituted with 1, 2, or 3 of R⁴.
In some embodiments, R³ is hydrogen.
In some embodiments, R³ is alkyl or —OR^c, wherein alkyl is optionally substituted with R⁵.
In some embodiments, R⁴ is halogen or 5 or 6-membered heteroaryl, wherein the 5 or 6 membered heteroaryl is optionally substituted with alkyl.
In some embodiments, R⁴ is halogen.
In some embodiments, R⁵ is cyano or —OR^c.
In some embodiments, R⁵ is —OR^c.
In some embodiments, R^c is alkyl or carbocyclyl, wherein the alkyl or carbocyclyl is optionally substituted with 1, 2, or 3 of R⁶.
In some embodiments, R⁶ is halogen.
In some embodiments, n is 0 or 1.
In some embodiments, the compound is selected from the group consisting of:

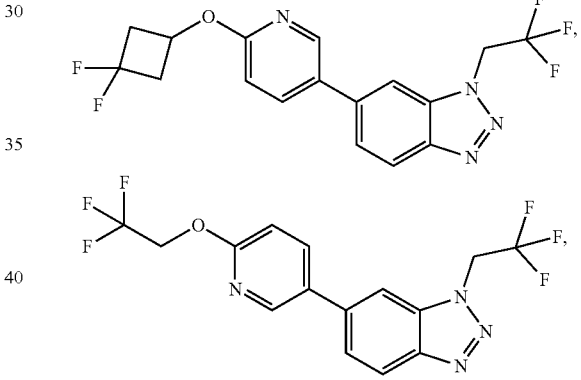

or a pharmaceutically acceptable salt thereof.

In any and all aspects, in some embodiments, the compound of Formulae (I), (I-a), (I-b), (I-c), (II), (II-a), (III), (IV), and (IV-a) is a compound selected from:

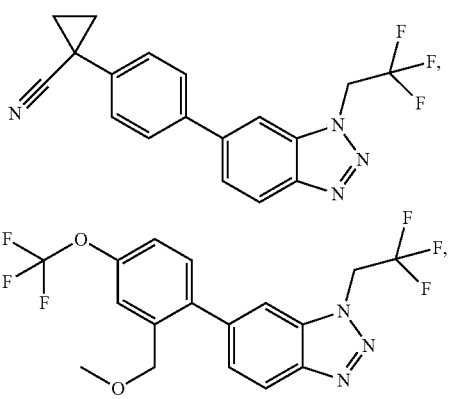

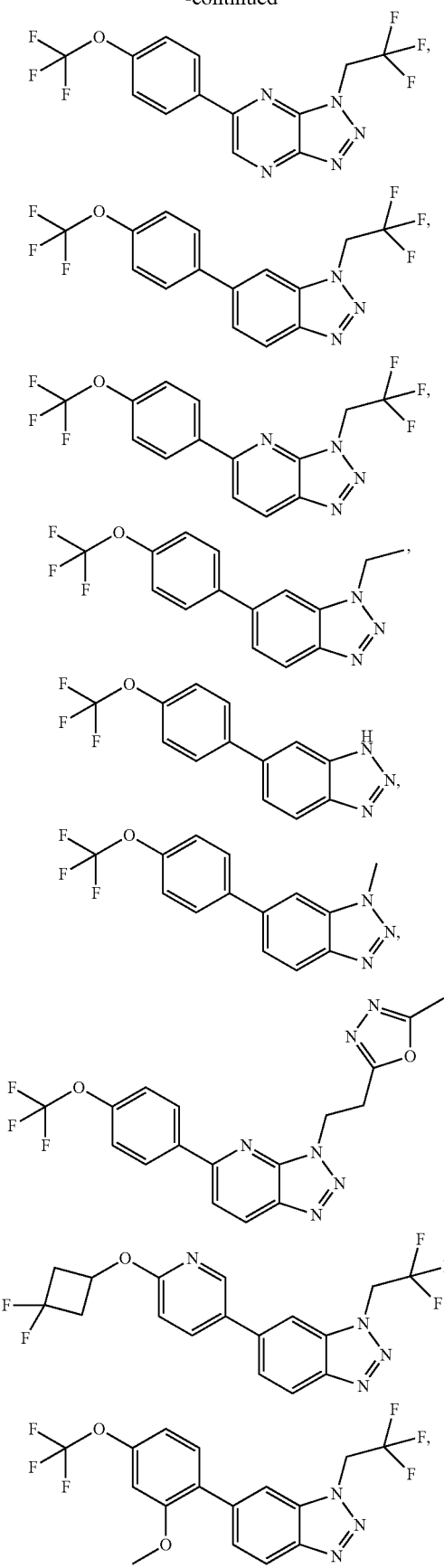
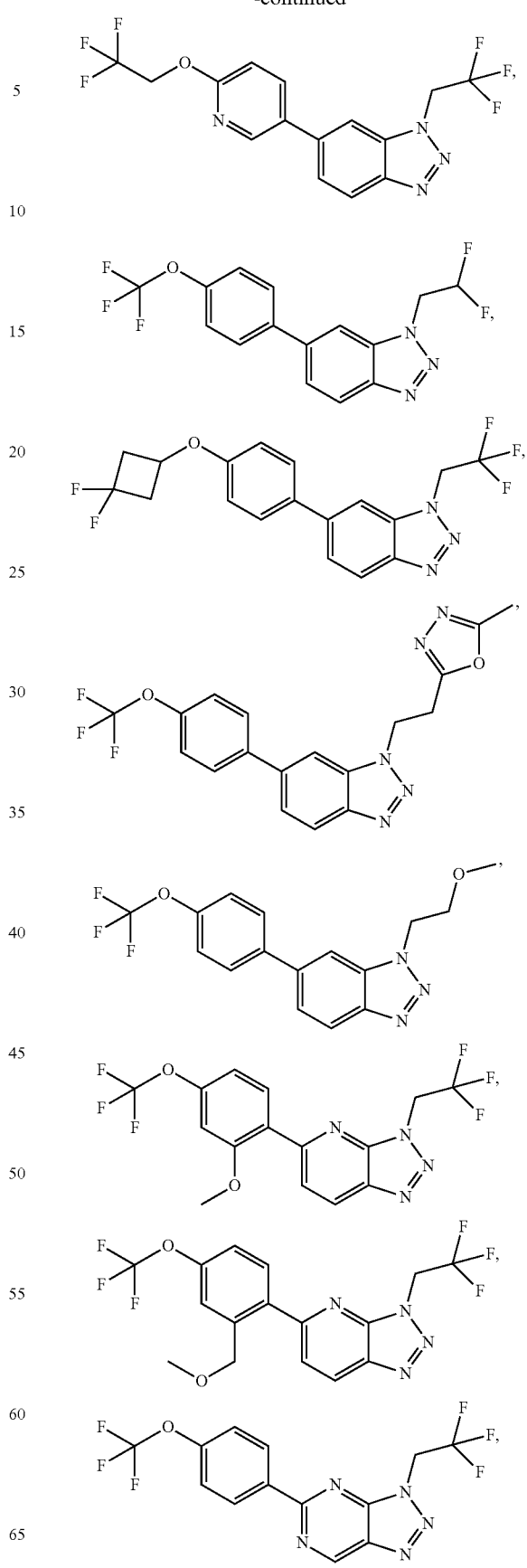

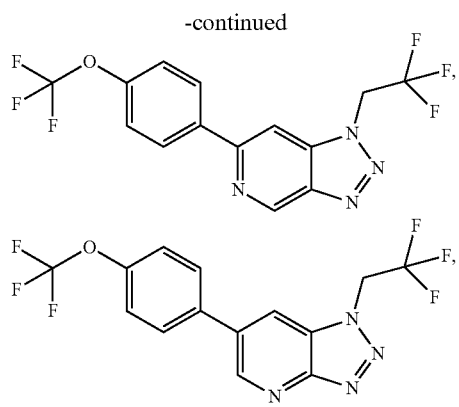

or a pharmaceutically acceptable salt thereof.

Methods of Treatment

Described herein are compounds and compositions thereof and their use to treat a disease, disorder, or condition relating to aberrant function of a sodium channel ion channel, e.g., abnormal late sodium (INaL) current. In some embodiments, a compound provided by the present invention is effective in the treatment of epilepsy or an epilepsy syndrome, a neurodevelopmental disorder, pain, or a neuromuscular disorder. Compounds of the invention may also modulate all sodium ion channels, or may be specific to only one or a plurality of sodium ion channels, e.g., $Na_V$ 1.1, 1.2, 1.5, 1.6, 1.7, 1.8, and/or 1.9.

In typical embodiments, the present invention is intended to encompass the compounds disclosed herein, and the pharmaceutically acceptable salts, pharmaceutically acceptable esters, tautomeric forms, polymorphs, and prodrugs of such compounds. In some embodiments, the present invention includes a pharmaceutically acceptable addition salt, a pharmaceutically acceptable ester, a hydrate of an addition salt, a tautomeric form, a polymorph, an enantiomer, a mixture of enantiomers, a stereoisomer or mixture of stereoisomers (pure or as a racemic or non-racemic mixture) of a compound described herein, e.g. a compound of Formula (I), (I-a), (I-b), (I-c), (II), (II-a), (III), (IV), or (IV-a); such as a compound of Formula (I), (I-a), (I-b), (I-c), (II), (II-a), (III), (IV), or (IV-a) named herein.

Epilepsy and Epilepsy Syndromes

The compounds described herein are useful in the treatment of epilepsy and epilepsy syndromes. Epilepsy is a CNS disorder in which nerve cell activity in the brain becomes disrupted, causing seizures or periods of unusual behavior, sensations and sometimes loss of consciousness. Seizure symptoms will vary widely, from a simple blank stare for a few seconds to repeated twitching of their arms or legs during a seizure.

Epilepsy may involve a generalized seizure or a partial or focal seizure. All areas of the brain are involved in a generalized seizure. A person experiencing a generalized seizure may cry out or make some sound, stiffen for several seconds to a minute a then have rhythmic movements of the arms and legs. The eyes are generally open, the person may appear not to be breathing and actually turn blue. The return to consciousness is gradual and the person maybe confused from minutes to hours. There are six main types of generalized seizures: tonic-clonic, tonic, clonic, myoclonic, absence, and atonic seizures. In a partial or focal seizure, only part of the brain is involved, so only part of the body is affected. Depending on the part of the brain having abnormal electrical activity, symptoms may vary.

Epilepsy, as described herein, includes a generalized, partial, complex partial, tonic clonic, clonic, tonic, refractory seizures, status epilepticus, absence seizures, febrile seizures, or temporal lobe epilepsy.

The compounds described herein may also be useful in the treatment of epilepsy syndromes. Severe syndromes with diffuse brain dysfunction caused, at least partly, by some aspect of epilepsy, are also referred to as epileptic encephalopathies. These are associated with frequent seizures that are resistant to treatment and severe cognitive dysfunction, for instance West syndrome.

In some embodiments, the epilepsy syndrome comprises an epileptic encephalopathy, such as Dravet syndrome, Angelman syndrome, CDKL5 disorder, frontal lobe epilepsy, infantile spasms, West's syndrome, Juvenile Myoclonic Epilepsy, Landau-Kleffner syndrome, Lennox-Gastaut syndrome, Ohtahara syndrome, PCDH19 epilepsy, or Glut1 deficiency.

In some embodiments, the epilepsy or epilepsy syndrome is a genetic epilepsy or a genetic epilepsy syndrome. In some embodiments, epilepsy or an epilepsy syndrome comprises epileptic encephalopathy, epileptic encephalopathy with SCN1A, SCN2A, SCN8A mutations, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, or KCNT1 epileptic encephalopathy.

In some embodiments, the methods described herein further comprise identifying a subject having epilepsy or an epilepsy syndrome (e.g., epileptic encephalopathy, epileptic encephalopathy with SCN1A, SCN2A, SCN8A mutations, early infantile epileptic encephalopathy, Dravet syndrome, Dravet syndrome with SCN1A mutation, generalized Epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, or KCNT1 epileptic encephalopathy) prior to administration of a compound described herein (e.g., a compound of Formula (I), (I-a), (I-b), (I-c), (II), (II-a), (III), (IV), or (IV-a)).

In one aspect, the present invention features a method of treating epilepsy or an epilepsy syndrome (e.g., epileptic encephalopathy, epileptic encephalopathy with SCN1A, SCN2A, SCN8A mutations, early infantile epileptic encephalopathy, Dravet syndrome, Dravet syndrome with SCN1A mutation, generalized Epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, or KCNT1 epileptic encephalopathy) comprising administering to a subject in need thereof a compound of Formula (I):

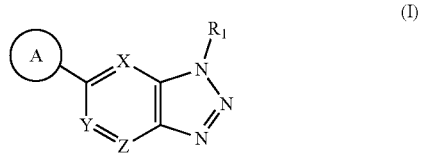

or a pharmaceutically acceptable salt thereof, wherein each of X, Y, and Z is independently N or $CR^2$; A is aryl or heteroaryl (e.g., a monocyclic 6-membered aryl or heteroaryl), wherein aryl and heteroaryl are optionally substituted with one or more (e.g., 1, 2, 3, or 4; e.g., 1, 2, or 3) $R^3$; $R^1$ is independently hydrogen, alkyl, alkenyl, alkynyl, carbocyclyl, heterocyclyl, aryl, or heteroaryl, wherein alkyl, alkenyl, alkynyl, carbocyclyl, heterocyclyl, aryl, and heteroaryl are optionally substituted with one or more (e.g., 1, 2, 3, or 4; e.g., 1, 2, or 3) $R^4$; $R^2$ is hydrogen, alkyl or halogen; each $R^3$ is independently alkyl, halo, cyano, nitro, carbocyclyl, heterocyclyl, —$OR^c$, —$N(R^d)_2$, —$C(O)R^c$, —$C(O)OR^c$, or —$C(O)N(R^d)_2$, wherein alkyl, carbocyclyl, and heterocyclyl are optionally substituted with one or more (e.g., 1, 2, 3, or 4; e.g., 1, 2, or 3) $R^5$; each $R^4$ and $R^5$ is independently alkyl, halo, cyano, nitro, or —$OR^c$; each $R^c$ is independently hydrogen, alkyl, aryl, or heteroaryl, wherein alkyl, aryl, and heteroaryl is optionally substituted by one or more (e.g., 1, 2, 3, or 4; e.g., 1, 2, or 3) $R^6$; each $R^d$ is independently hydrogen or alkyl; and each $R^6$ is independently alkyl, carbocyclyl, heterocyclyl, halo, cyano, nitro, or —OH.

A compound of the present invention (e.g., a compound of Formula (I), (I-a), (I-b), (I-c), (II), (II-a), (III), (IV), or (IV-a)) may also be used to treat an epileptic encephalopathy, wherein the subject has a mutation in one or more (e.g., 1, 2, 3, or 4; e.g., 1, 2, or 3) of ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDC5, DNM1, EEF1A2, EPM2A, EPM2B, GABRA1, GABRB3, GABRG2, GNAO1, GOSR2, GRIN1, GRIN2A, GRIN2B, HCN1, IER3IP1, KCNA2, KCNB1, KCNC1, KCNMA1, KCNQ2, KCNQ3, KCNT1, KCTD7, LGI1, MEF2C, NHLRC1, PCDH19, PLCB1, PNKP, PNPO, PRICKLE1, PRICKLE2, PRRT2, RELN, SCARB2, SCN1A, SCN1B, SCN2A, SCN8A, SCN9A, SIAT9, SDC1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, and WWOX.

In some embodiments, the methods described herein further comprise identifying a subject having a mutation in one or more (e.g., 1, 2, 3, or 4; e.g., 1, 2, or 3) of ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDC5, DNM1, EEF1A2, EPM2A, EPM2B, GABRA1, GABRB3, GABRG2, GNAO1, GOSR2, GRIN1, GRIN2A, GRIN2B, HCN1, IER3IP1, KCNA2, KCNB1, KCNC1, KCNMA1, KCNQ2, KCNQ3, KCNT1, KCTD7, LGI1, MEF2C, NHLRC1, PCDH19, PLCB1, PNKP, PNPO, PRICKLE1, PRICKLE2, PRRT2, RELN, SCARB2, SCN1A, SCN1B, SCN2A, SCN8A, SCN9A, SIAT9, SDC1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, and WWOX prior to administration of a compound described herein (e.g., a compound of Formula (I), (I-a), (I-b), (I-c), (II), (II-a), (III), (IV), or (IV-a)).

Neurodevelopmental Disorders

The compounds described herein may be useful in the treatment of a neurodevelopmental disorder. In some embodiments, the neurodevelopmental disorder comprises autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy. In some embodiments, the methods described herein further comprise identifying a subject having a neurodevelopmental disorder (e.g., autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy) prior to administration of a compound described herein (e.g., a compound of Formula (I), (I-a), (I-b), (I-c), (II), (II-a), (III), (IV), or (IV-a)).

In one aspect, the present invention features a method of treating a neurodevelopmental disorder (e.g., autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy) comprising administering to a subject in need thereof a compound of Formula (I):

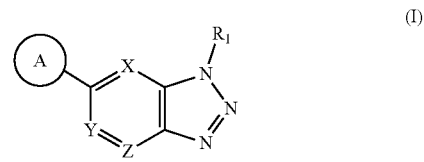

or a pharmaceutically acceptable salt thereof, wherein each of X, Y, and Z is independently N or $CR^2$; A is aryl or heteroaryl (e.g., a monocyclic 6-membered aryl or heteroaryl), wherein aryl and heteroaryl are optionally substituted with one or more (e.g., 1, 2, 3, or 4; e.g., 1, 2, or 3) $R^3$; $R^1$ is independently hydrogen, alkyl, alkenyl, alkynyl, carbocyclyl, heterocyclyl, aryl, or heteroaryl, wherein alkyl, alkenyl, alkynyl, carbocyclyl, heterocyclyl, aryl, and heteroaryl are optionally substituted with one or more (e.g., 1, 2, 3, or 4; e.g., 1, 2, or 3) $R^4$; $R^2$ is hydrogen, alkyl or halogen; each $R^3$ is independently alkyl, halo, cyano, nitro, carbocyclyl, heterocyclyl, —$OR^c$, —$N(R^d)_2$, —$C(O)R^c$, —$C(O)OR^c$, or —$C(O)N(R^d)_2$, wherein alkyl, carbocyclyl, and heterocyclyl are optionally substituted with one or more (e.g., 1, 2, 3, or 4; e.g., 1, 2, or 3) $R^5$; each $R^4$ and $R^5$ is independently alkyl, halo, cyano, nitro, or —$OR^c$; each $R^c$ is independently hydrogen, alkyl, aryl, or heteroaryl, wherein alkyl, aryl, and heteroaryl is optionally substituted by one or more (e.g., 1, 2, 3, or 4; e.g., 1, 2, or 3) $R^6$; each $R^d$ is independently hydrogen or alkyl; and each $R^6$ is independently alkyl, carbocyclyl, heterocyclyl, halo, cyano, nitro, or —OH.

Neuromuscular Disorders

The compounds described herein may be useful in the treatment of a neuromuscular disorder. In some embodiments, the neuromuscular disorder comprises amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation. In some embodiments, the methods described herein further comprise identifying a subject having a neuromuscular disorder (e.g., amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation) prior to administration of a compound described herein (e.g., a compound of Formula (I), (I-a), (I-b), (I-c), (II), (II-a), (III), (IV), or (IV-a)).

In one aspect, the present invention features a method of treating a neuromuscular disorder (e.g., amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation) comprising administering to a subject in need thereof a compound of Formula (I):

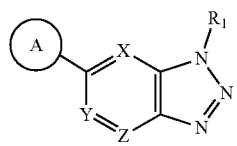

(I)

or a pharmaceutically acceptable salt thereof, wherein each of X, Y, and Z is independently N or $CR^2$; A is aryl or heteroaryl (e.g., a monocyclic 6-membered aryl or heteroaryl), wherein aryl and heteroaryl are optionally substituted with one or more (e.g., 1, 2, 3, or 4; e.g., 1, 2, or 3) $R^3$; $R^1$ is independently hydrogen, alkyl, alkenyl, alkynyl, carbocyclyl, heterocyclyl, aryl, or heteroaryl, wherein alkyl, alkenyl, alkynyl, carbocyclyl, heterocyclyl, aryl, and heteroaryl are optionally substituted with one or more (e.g., 1, 2, 3, or 4; e.g., 1, 2, or 3) $R^4$; $R^2$ is hydrogen, alkyl or halogen; each $R^3$ is independently alkyl, halo, cyano, nitro, carbocyclyl, heterocyclyl, $-OR^c$, $-N(R^d)_2$, $-C(O)R^c$, $-C(O)OR^c$, or $-C(O)N(R^d)_2$, wherein alkyl, carbocyclyl, and heterocyclyl are optionally substituted with one or more (e.g., 1, 2, 3, or 4; e.g., 1, 2, or 3) $R^5$; each $R^4$ and $R^5$ is independently alkyl, halo, cyano, nitro, or $-OR^c$; each $R^c$ is independently hydrogen, alkyl, aryl, or heteroaryl, wherein alkyl, aryl, and heteroaryl is optionally substituted by one or more (e.g., 1, 2, 3, or 4; e.g., 1, 2, or 3) $R^6$; each $R^d$ is independently hydrogen or alkyl; and each $R^6$ is independently alkyl, carbocyclyl, heterocyclyl, halo, cyano, nitro, or $-OH$.

Pain

The compounds described herein may be useful in the treatment of pain. In some embodiments, the pain comprises neuropathic pain, trigeminal neuralgia, migraine, hemiplegic migraine, familial hemiplegic migraine, familial hemiplegic migraine type 3, cluster headache, trigeminal neuralgia, cerebellar ataxia, or a related headache disorder. In some embodiments, the methods described herein further comprise identifying a subject having pain (e.g., neuropathic pain, trigeminal neuralgia, migraine, hemiplegic migraine, familial hemiplegic migraine, familial hemiplegic migraine type 3, cluster headache, trigeminal neuralgia, cerebellar ataxia, or a related headache disorder) prior to administration of a compound described herein (e.g., a compound of Formula (I), (I-a), (I-b), (I-c), (II), (II-a), (III), (IV), or (IV-a)).

In one aspect, the present invention features a method of treating pain (e.g., neuropathic pain, trigeminal neuralgia, migraine, hemiplegic migraine, familial hemiplegic migraine, familial hemiplegic migraine type 3, cluster headache, trigeminal neuralgia, cerebellar ataxia, or a related headache disorder) comprising administering to a subject in need thereof a compound of Formula (I):

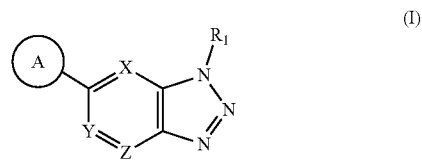

(I)

or a pharmaceutically acceptable salt thereof, wherein each of X, Y, and Z is independently N or $CR^2$; A is aryl or heteroaryl (e.g., a monocyclic 6-membered aryl or heteroaryl), wherein aryl and heteroaryl are optionally substituted with one or more (e.g., 1, 2, 3, or 4; e.g., 1, 2, or 3) $R^3$; $R^1$ is independently hydrogen, alkyl, alkenyl, alkynyl, carbocyclyl, heterocyclyl, aryl, or heteroaryl, wherein alkyl, alkenyl, alkynyl, carbocyclyl, heterocyclyl, aryl, and heteroaryl are optionally substituted with one or more (e.g., 1, 2, 3, or 4; e.g., 1, 2, or 3) $R^4$; $R^2$ is hydrogen, alkyl or halogen; each $R^3$ is independently alkyl, halo, cyano, nitro, carbocyclyl, heterocyclyl, $-OR^c$, $-N(R^d)_2$, $-C(O)R^c$, $-C(O)OR^c$, or $-C(O)N(R^d)_2$, wherein alkyl, carbocyclyl, and heterocyclyl are optionally substituted with one or more (e.g., 1, 2, 3, or 4; e.g., 1, 2, or 3) $R^5$; each $R^4$ and $R^5$ is independently alkyl, halo, cyano, nitro, or $-OR^c$; each $R^c$ is independently hydrogen, alkyl, aryl, or heteroaryl, wherein alkyl, aryl, and heteroaryl is optionally substituted by one or more (e.g., 1, 2, 3, or 4; e.g., 1, 2, or 3) $R^6$; each $R^d$ is independently hydrogen or alkyl; and each $R^6$ is independently alkyl, carbocyclyl, heterocyclyl, halo, cyano, nitro, or $-OH$.

Other Disorders

In some embodiments, a compound of the present invention (e.g., a compound of Formula (I), (I-a), (I-b), (I-c), (II), (II-a), (III), (IV), or (IV-a)) may have appropriate pharmacokinetic properties such that they may active with regard to the central and/or peripheral nervous system. In some embodiments, the compounds provided herein are used to treat a cardiovascular disease such as atrial and ventricular arrhythmias, including atrial fibrillation, Prinzmetal's (variant) angina, stable angina, unstable angina, ischemia and reperfusion injury in cardiac, kidney, liver and the brain, exercise induced angina, pulmonary hypertension, congestive heart disease including diastolic and systolic heart failure, and myocardial infarction. In some embodiments, the compounds provided herein may be used in the treatment of diseases affecting the neuromuscular system resulting in itching, seizures, or paralysis, or in the treatment of diabetes or reduced insulin sensitivity, and disease states related to diabetes, such as diabetic peripheral neuropathy.

In one aspect, the present invention provides a method of treating a neurological disorder or a psychiatric disorder, wherein the method comprises administering to a subject in need thereof a compound disclosed herein or a pharmaceutically acceptable salt thereof or a pharmaceutical composition disclosed herein.
In any and all aspects, in some embodiments, the compound of Formulae (I), (I-a), (I-b), (I-c), (II), (II-a), (III), (IV), or (IV-a) is selected from:
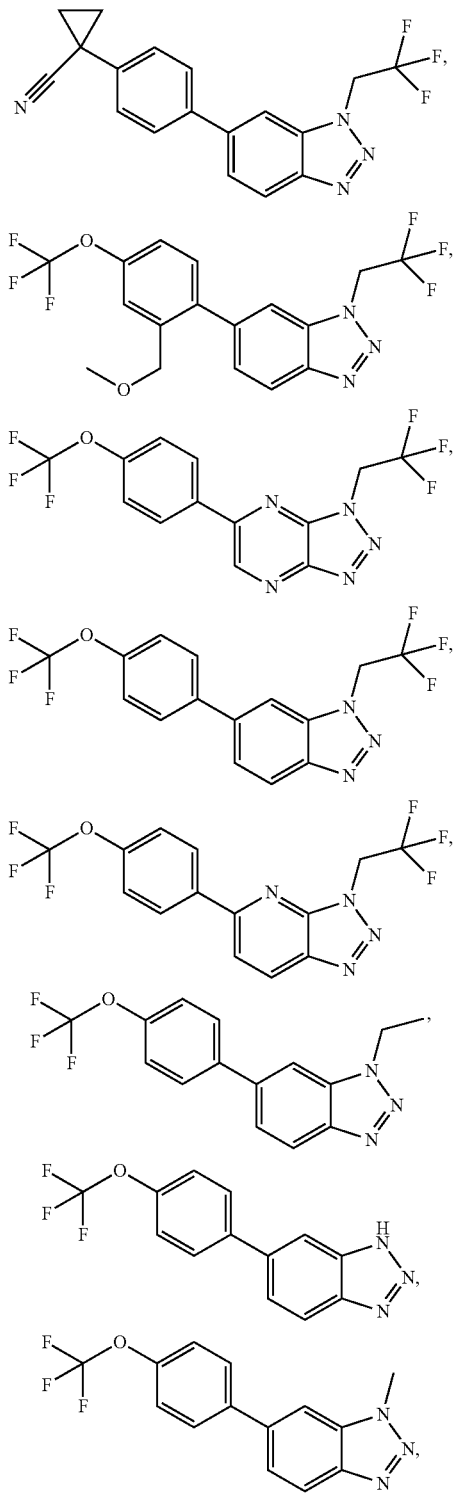
-continued
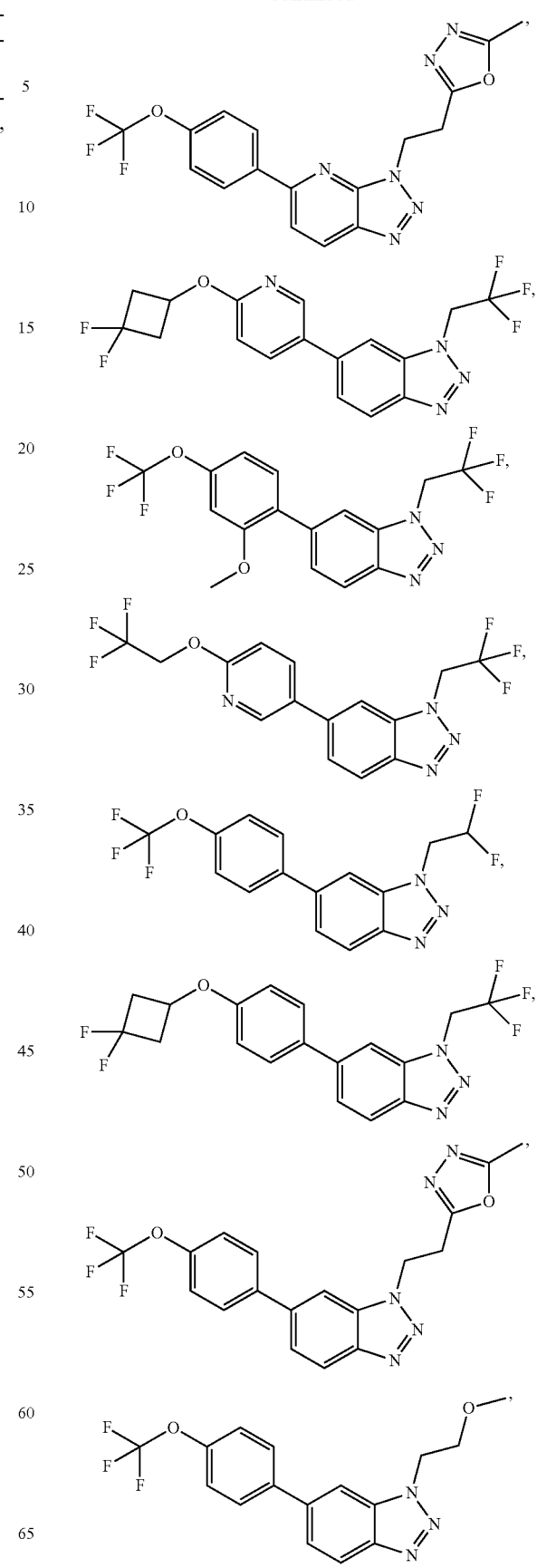

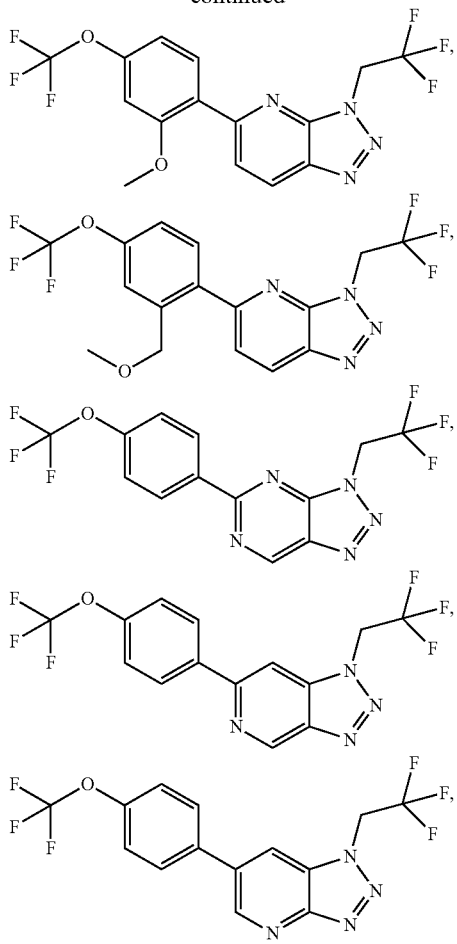

or a pharmaceutically acceptable salt thereof.

Pharmaceutical Compositions and Routes of Administration

Compounds provided in accordance with the present invention are usually administered in the form of pharmaceutical compositions. This invention therefore provides pharmaceutical compositions that contain, as the active ingredient, one or more (e.g., 1, 2, 3, or 4; e.g., 1, 2, or 3) of the compounds described, or a pharmaceutically acceptable salt or ester thereof, and one or more (e.g., 1, 2, 3, or 4; e.g., 1, 2, or 3) pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

In one aspect, the present invention provides a pharmaceutical composition comprising a compound disclosed herein, or pharmaceutically acceptable salt thereof, and a pharmaceutically acceptable carrier.

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g of a compound described herein, and for parenteral administration, preferably from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Combination Therapy

A compound or composition described herein (e.g., for use in modulating a sodium ion channel, e.g., the late sodium (INaL) current) may be administered in combination with another agent or therapy. A subject to be administered a compound disclosed herein may have a disease, disorder, or condition, or a symptom thereof, that would benefit from treatment with another agent or therapy. These diseases or conditions can relate to epilepsy or an epilepsy syndrome, a neurodevelopmental disorder, pain, or a neuromuscular disorder.

Antiepilepsy Agents

Anti-epilepsy agents include brivaracetam, carbamazepine, clobazam, clonazepam, diazepam, divalproex, eslicarbazepine, ethosuximide, ezogabine, felbamate, gabapentin, lacosamide, lamotrigine, levetiracetam, lorazepam, oxcarbezepine, permpanel, phenobarbital, phenytoin, pregabalin, primidone, ruflnamide, tigabine, topiramate, valproic acid, vigabatrin, zonisamide.

Cardiovascular Agent Combination Therapy

Cardiovascular related diseases or conditions that can benefit from a combination treatment of the sodium channel blockers of the invention with other therapeutic agents include, without limitation, angina including stable angina, unstable angina (UA), exercised-induced angina, variant angina, arrhythmias, intermittent claudication, myocardial infarction including non-STE myocardial infarction (NSTEMI), pulmonary hypertension including pulmonary arterial hypertension, heart failure including congestive (or chronic) heart failure and diastolic heart failure and heart failure with preserved ejection fraction (diastolic dysfunction), acute heart failure, or recurrent ischemia.

Therapeutic agents suitable for treating cardiovascular related diseases or conditions include anti-anginals, heart failure agents, antithrombotic agents, anti arrhythmic agents, antihypertensive agents, and lipid lowering agents.

The co-administration of the sodium channel blockers of the invention with therapeutic agents suitable for treating cardiovascular related conditions allows enhancement in the standard of care therapy the patient is currently receiving.

Anti-Anginals

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol (Sectral), atenolol (Tenormin), betaxolol (Kerlone), bisoprolol/hydrochlorothiazide (Ziac), bisoprolol (Zebeta), carteolol (Cartrol), esmolol (Brevibloc), labetalol (Normodyne, Trandate), metoprolol (Lopressor, Toprol XL), nadolol (Corgard), propranolol (Inderal), sotalol (Betapace), and timolol (Blocadren).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine (Norvasc, Lotrel), bepridil (Vascor), diltiazem (Cardizem, Tiazac), felodipine (Plendil), nifedipine (Adalat, Procardia), nimodipine (Nimotop), nisoldipine (Sular), verapamil (Calan, Isoptin, Verelan), and nicardipine.

Heart Failure Agents

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn), furosemide (Lasix), bumetanide (Bumex), spironolactone (Aldactone), and eplerenone (lnspra).

Angiotensin converting enzyme (ACE) inhibitors reduce the workload on the heart by expanding the blood vessels and decreasing resistance to blood flow. Examples of ACE inhibitors include benazepril (Lotensin), captopril (Capoten), enalapril (Vasotec), fosinopril (Monopril), lisinopril (Prinivil, Zestril), moexipril (Univasc), perindopril (Aceon), quinapril (Accupril), ramipril (Altace), and trandolapril (Mavik).

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotic Agents

Antithrombotics inhibit the clotting ability of the blood. There are three main types of antithrombotics-platelet inhibitors, anticoagulants, and thrombolytic agents.

Platelet inhibitors inhibit the clotting activity of platelets, thereby reducing clotting in the arteries. Examples of platelet inhibitors include acetylsalicylic acid (aspirin), ticlopidine, clopidogrel (plavix), dipyridamole, cilostazol, persantine sulfinpyrazone, dipyridamole, indomethacin, and glycoprotein IIb/IIIa inhibitors, such as abciximab, tirofiban, and eptifibatide (Integrelin). Beta blockers and calcium channel blockers also have a platelet-inhibiting effect.

Anticoagulants prevent blood clots from growing larger and prevent the formation of new clots. Examples of anticoagulants include bivalirudin (Angiomax), warfarin (Coumadin), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNK), and tissue plasminogen activator (t-PA).

Antiarrhythmic Agents

Antiarrhythmic agents are used to treat disorders of the heart rate and rhythm. Examples of antiarrhythmic agents include amiodarone, dronedarone, quinidine, procainamide, lidocaine, and propafenone. Cardiac glycosides and beta blockers are also used as antiarrhythmic agents.

Combinations with amiodarone and dronedarone are of particular interest given the recently discovered synergistic effects of the sodium channel blocker ranolazine and amioarone and dronedarone.

Antihypertensive Agents

Antihypertensive agents are used to treat hypertension, a condition in which the blood pressure is consistently higher than normal. Hypertension is associated with many aspects of cardiovascular disease, including congestive heart failure, atherosclerosis, and clot for illation. Examples of antihypertensive agents include alpha-1-adrenergic antagonists, such as prazosin (Minipress), doxazosin mesylate (Cardura), prazosin hydrochloride (Minipress), prazosin, polythiazide (Minizide), and terazosin hydrochloride (Hytrin); beta-adrenergic antagonists, such as propranolol (Inderal), nadolol (Corgard), timolol (Blocadren), metoprolol (Lopressor), and pindolol (Visken); central alpha-adrenoceptor agonists, such as clonidine hydrochloride (Catapres), clonidine hydrochloride and chlorthalidone (Clorpres, Combipres), guanabenz Acetate (Wytensin), guanfacine hydrochloride (Tenex), methyldopa (Aldomet), methyldopa and chlorothiazide (Aldoclor), methyldopa and hydrochlorothiazide (Aldoril); combined alpha/beta-adrenergic antagonists, such as labetalol (Normodyne, Trandate), Carvedilol (Coreg); adrenergic neuron blocking agents, such as guanethidine (ismelin), reserpine (Serpasil); central nervous system-acting antihypertensives, such as clonidine (Catapres), methyldopa (Aldomet), guanabenz (Wytensin); anti-angiotensin II agents; ACE inhibitors, such as perindopril (Aceon) captopril (Capoten), enalapril (Vasotec), lisinopril (Prinivil, Zestril); angiotensin-II receptor antagonists, such as Candesartan (Atacand), Eprosartan (Teveten), Irbesartan (Avapro), Losartan (Cozaar), Telmisartan (Micardis), Valsartan (Diovan); calcium channel blockers, such as verapamil (Calan, Isoptin), diltiazem (Cardizem), nifedipine (Adalat, Procardia); diuretics; direct vasodilators, such as nitroprusside (Nipride), diazoxide (Hyperstat IV), hydralazine (Apresoline), minoxidil (Loniten), verapamil; and potassium channel activators, such as aprikalim, bimakalim, cromakalim, emakalim, nicorandil, and pinacidil.

Lipid Lowering Agents

Lipid lowering agents are used to lower the amounts of cholesterol or fatty sugars present in the blood. Examples of lipid lowering agents include bezafibrate (Bezalip), ciprofibrate (Modalim), and statins, such as atorvastatin (Lipitor), fluvastatin (Lescol), lovastatin (Mevacor, Altocor), mevastatin, pitavastatin (Livalo, Pitava) pravastatin (Lipostat), rosuvastatin (Crestor), and simvastatin (Zocor).

In this invention, the patient presenting with an acute coronary disease event often suffers from secondary medical conditions such as one or more of a metabolic disorder, a pulmonary disorder, a peripheral vascular disorder, or a gastrointestinal disorder. Such patients can benefit from treatment of a combination therapy comprising administering to the patient ranolazine in combination with at least one therapeutic agent.

Pulmonary Disorders Combination Therapy

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire, Bricanyl), albuterol (Proventil), salmeterol (Serevent, Serevent Diskus), theophylline, ipratropium bromide (Atrovent), tiotropium (Spiriva), methylprednisolone (Solu-Medrol, Medrol), magnesium, and potassium.

Metabolic Disorders Combination Therapy

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics.

Peripheral Vascular Disorders Combination Therapy

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Gastrointestinal Disorders Combination Therapy

Gastrointestinal disorders refer to diseases and conditions associated with the gastrointestinal tract. Examples of gastrointestinal disorders include gastroesophageal reflux disease (GERD), inflammatory bowel disease (IBD), gastroenteritis, gastritis and peptic ulcer disease, and pancreatitis.

Examples of therapeutic agents used to treat gastrointestinal disorders include proton pump inhibitors, such as pantoprazole (Protonix), lansoprazole (Prevacid), esomeprazole (Nexium), omeprazole (Prilosec), rabeprazole; H2 blockers, such as cimetidine (Tagamet), ranitidine (Zantac), famotidine (Pepcid), nizatidine (Axid); prostaglandins, such as misoprostoL (Cytotec); sucralfate; and antacids.

Antibiotics, Analgesics, Antidepressants and Anti-Anxiety Agents Combination Therapy Patients presenting with an acute coronary disease event may exhibit conditions that benefit from administration of therapeutic agent or agents that are antibiotics, analgesics, antidepressant and anti-anxiety agents in combination with ranolazine.

Antibiotics

Antibiotics are therapeutic agents that kill, or stop the growth of, microorganisms, including both bacteria and fungi. Example of antibiotic agents include .beta.-Lactam antibiotics, including penicillins (amoxicillin), cephalosporins, such as cefazolin, cefuroxime, cefadroxil (Duricef), cephalexin (Keflex), cephradine (Velosef), cefaclor (Ceclor), cefuroxime axtel (Ceftin), cefprozil (Cefzil), loracarbef (Lorabid), cefixime (Suprax), cefpodoxime proxetil (Vantin), ceftibuten (Cedax), cefdinir (Omnicef), ceftriaxone (Rocephin), carbapenems, and monobactams; tetracyclines, such as tetracycline; macrolide antibiotics, such as erythromycin; aminoglycosides, such as gentamicin, tobramycin, amikacin; quinolones such as ciprofloxacin; cyclic peptides, such as vancomycin, streptogramins, polymyxins; lincosamides, such as clindamycin; oxazolidinoes, such as linezolid; and sulfa antibiotics, such as sulfisoxazole.

Analgesics

Analgesics are therapeutic agents that are used to relieve pain. Examples of analgesics include opiates and morphinomimetics, such as fentanyl and morphine; paracetamol; NSAIDs, and COX-2 inhibitors. Given the ability of the sodium channel blockers of the invention to treat neuropathic pain via inhibition of the $Na_V$ 1.7 and 1.8 sodium channels, combination with analgesics are particularly envisioned. See U.S. Patent Application Publication 20090203707.

Antidepressant and Anti-Anxiety Agents

Antidepressant and anti-anxiety agents include those agents used to treat anxiety disorders, depression, and those used as sedatives and tranquillizers. Examples of antidepressant and anti-anxiety agents include benzodiazepines, such as diazepam, lorazepam, and midazolam; barbiturates; glutethimide; chloral hydrate; meprobamate; sertraline (Zoloft, Lustral, Apo-Sertral, Asentra, Gladem, Serlift, Stimuloton); escitalopram (Lexapro, Cipralex); fluoxetine (Prozac, Sarafem, Fluctin, Fontex, Prodep, Fludep, Lovan); venlafaxine (Effexor XR, Efexor); citalopram (Celexa, Cipramil, Talohexane); paroxetine (Paxil, Seroxat, Aropax); trazodone (Desyrel); amitriptyline (Elavil); and bupropion (Wellbutrin, Zyban).

Accordingly, one aspect of the invention provides for a composition comprising the sodium channel blockers of the invention and at least one therapeutic agent. In an alternative embodiment, the composition comprises the sodium channel blockers of the invention and at least two therapeutic agents. In further alternative embodiments, the composition comprises the sodium channel blockers of the invention and at least three therapeutic agents, the sodium channel blockers of the invention and at least four therapeutic agents, or the sodium channel blockers of the invention and at least five therapeutic agents.

The methods of combination therapy include co-administration of a single formulation containing the sodium channel modulators (e.g., blockers) of the invention and therapeutic agent or agents, essentially contemporaneous administration of more than one formulation comprising the sodium channel modulator (e.g., blocker) of the invention and therapeutic agent or agents, and consecutive administration of a sodium channel blocker of the invention and therapeutic agent or agents, in any order, wherein preferably there is a time period where the sodium channel blocker of the invention and therapeutic agent or agents simultaneously exert their therapeutic effect.

EXAMPLES

In order that the invention described herein may be more fully understood, the following examples are set forth. The synthetic and biological examples described in this application are offered to illustrate the compounds, pharmaceutical compositions and methods provided herein and are not to be construed in any way as limiting their scope.

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimal reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include recrystallization, filtration, flash chromatography, trituration, high pressure liquid chromatography (HPLC), or supercritical fluid chromatography (SFC). Note that flash chromatography may either be performed manually or via an automated system. The compounds provided herein may be characterized by known standard procedures, such as nuclear magnetic resonance spectroscopy (NMR) or liquid chromatography mass spectrometry (LCMS). NMR chemical shifts are reported in part per million (ppm) and are generated using methods well known to those of skill in the art.

Exemplary general methods for analytical LCMS include Method A (Xtimate $C_{18}$ (2.1 mm×30 mm, 3 μm); A=$H_2O$ (0.04% TFA) and B=$CH_3CN$ (0.02% TFA); 50° C.; 1.2 mL/min; 10-80% B over 0.9 minutes, then 80% B for 0.6 minutes) and Method B (Chromolith Flash RP-18 end-capped $C_{18}$ (2 mm×25 mm); A=$H_2O$ (0.04% TFA) and B=$CH_3CN$ (0.02% TFA); 50° C.; 1.5 mL/min; 5-95% B over 0.7 minutes, then 95% B for 0.4 minutes).

LIST OF ABBREVIATIONS

EtOAc ethyl acetate
DMF N N-dimethylformamide
THF tetrahydrofuran
MeOH methanol
DCM dichloromethane
EtOH ethanol
TFA trifluoroacetic acid
dppf 1,1'-bis(diphenylphosphino)ferrocene
DMSO dimethyl sulfoxide
Pd(t-$Bu_3P)_2$ bis(tri-tert-butylphosphine)palladium(0)
NaH sodium hydride
Et$NH_2$ ethylamine
Me$NH_2$ methylamine
TBAB tetra-n-butylammonium bromide
NCS A-chlorosuccinimide
PMB p-methoxybenzane
TsOH p-toluenesulfonic acid
DIPEA N,N-diisopropylethylamine
DEAD diethyl azodicarboxylate
$PPh_3$ triphenylphosphine
$CF_3CH_2OTf$ trifluoroethyl trifluoromethanesulfonate Example 1: Synthesis of Compound 1

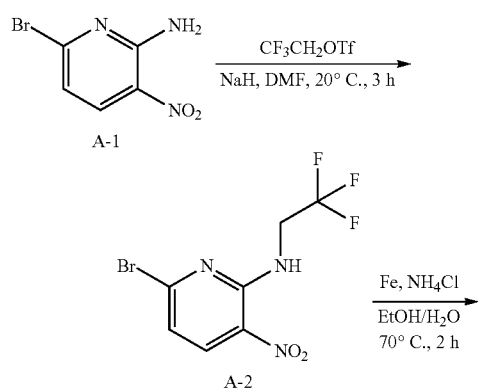

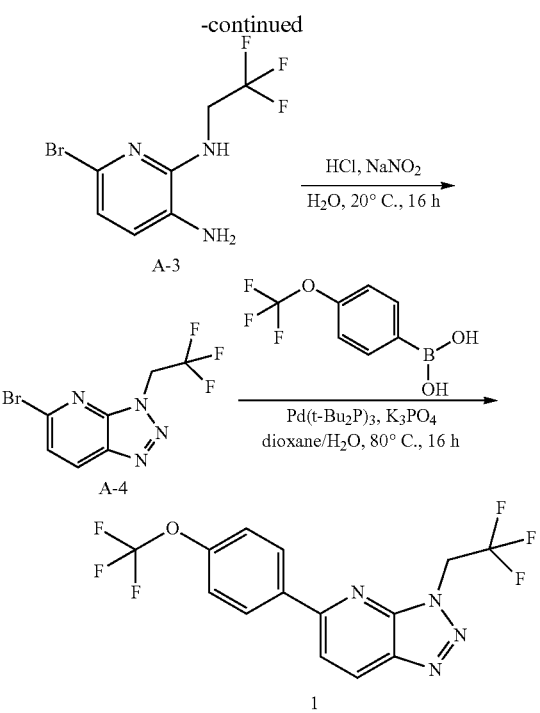

Synthesis of A-2: To a mixture of A-1 (200 mg, 917.40 μmol, 1 eq) in DMF (10 mL) was added NaH (40.37 mg, 1.01 mmol, 60% purity, 1.1 eq) and 2,2,2-trifluoroethyl trifluoromethane-sulfonate (234.22 mg, 1.01 mmol, 1.1 eq), and the mixture was stirred at 20° C. for 3 hours. The reaction was quenched with sat. $NH_4Cl$ (10 mL), and the mixture was extracted with EtOAc (20 mL×2). The combined organic phase was washed with brine (10 mL), dried over $Na_2SO_4$, filtered and concentrated to give A-2 (500 mg) as an oil. $^1H$ NMR (400 MHz, $CDCl_3$) $\delta_H$ 8.27 (d, 1H), 6.95 (d, 1H), 4.42-4.33 (m, 2H).

Synthesis of A-3: A mixture of A-3 (500 mg, 1.67 mmol, 1 eq), Fe (930.65 mg, 16.66 mmol, 10 eq) and $NH_4Cl$ (891.43 mg, 16.66 mmol, 582.63 μL, 10 eq) in EtOH (10 mL) and $H_2O$ (10 mL) was stirred at 70° C. for 2 hours. The mixture was filtered through Celite and eluted with EtOAc (20 mL×2). The filtrate was concentrated to give a solid, and the mixture was diluted with EtOAc (50 mL), washed with $H_2O$ (30 mL×2) and brine (20 mL), dried over $Na_2SO_4$, filtered and concentrated to afford A-3 (500 mg) as a solid. LCMS $R_f$=0.781 min in 1.5 min chromatography, MS ESI calcd. for $C_7H_8BrF_3N_3$ $[M+H]^+$ 270.0, found 269.8.

Synthesis of A-4: To a mixture of A-3 (200 mg, 740.60 μmol, 1 eq) in HCl (1 M, 37.03 mL, 50 eq) was added $NaNO_2$ (61.32 mg, 888.73 μmol, 48.29 μL, 1.2 eq). The mixture was stirred at 20° C. for 16 hours. The mixture was adjusted to pH=9 by 1M NaOH, then extracted with EtOAc (50 mL×2). The combined organic layers were washed with brine (30 mL), dried over $Na_2SO_4$, filtered and concentrated to give the crude product, which was purified by silica gel (EtOAc in PE=0 to 50% to 100%) to give A-4 (140 mg, 468.95 umol) as a solid. LCMS $R_f$=0.756 min in 1.5 min chromatography, MS ESI calcd. for $C_7H_5BrF_3N_4$ $[M+2+H]^+$ 283.0, found 282.8.

Synthesis of Compound 1: A mixture of A-4 (140 mg, 498.16 μmol, 1 eq), (4-(trifluoromethoxy)phenyl)boronic acid (205.17 mg, 996.33 μmol, 2 eq), Pd(dppf)$Cl_2$.$CH_2Cl_2$ (81.36 mg, 99.63 μmol, 0.2 eq) and $K_2CO_3$ (137.70 mg, 996.33 μmol, 2 eq) in dioxane (3 mL) and H$_2$O (0.5 mL) was stirred at 90° C. for 16 hours. The mixture was then filtered through silica gel and eluted with EtOAc (20 mL×2). The filtrate was concentrated and purified by Prep-HPLC to afford Compound 1 (75.81 mg, 207.63 umol) as a solid. $^1$H NMR (400 MHz, CDCl$_3$) δ$_H$ 8.50 (d, 1H), 8.18 (d, 2H), 7.88 (d, 1H), 7.39 (d, 2H), 5.39 (q, 2H). LCMS R$_t$=1.266 min in 2.0 min chromatography, MS ESI calcd. for C$_{14}$H$_9$F$_6$N$_4$O [M+H]$^+$ 363.1, found 362.9.

Example 2: Synthesis of Compound 2

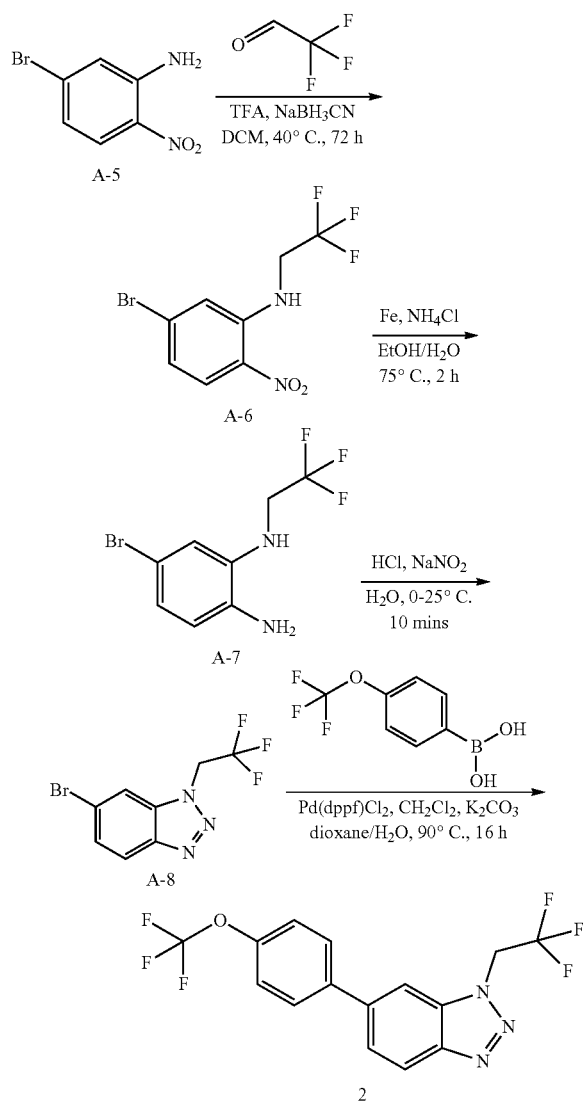

Synthesis of A-6: To a slurry of A-5 (2.00 g, 9.22 mmol, 1.00 eq) and NaBH$_3$CN (1.22 g, 19.36 mmol, 2.10 eq) in DCM (20 mL) was added TFA (13.46 g, 118.02 mmol, 8.74 mL, 12.80 eq) dropwise at 0° C. at a rate such that the internal temperature remained below 5° C. To the mixture was added 2,2,2-trifluoroacetaldehyde (3.01 g, 23.05 mmol, 2.50 eq) over mins. The mixture was stirred at 40° C. for 72 hours. The mixture was slowly poured into sat. NaHCO$_3$ (100 mL) at 0° C. and neutralized by the portion wise addition of solid NaHCO$_3$. The mixture was stirred for 30 mins and the precipitated solids were collected by filtration. Organic and aqueous phases of the filtrate were separated, and the aqueous layer was extracted with DCM (3×50 mL). The combined organic extracts were concentrated to dryness, combined with the solids collected previously, dissolved in EtOAc (100 mL), washed with H$_2$O (50 mL), brine (30 mL) dried over Na$_2$SO$_4$, filtered and concentrated. The crude product was purified by silica gel (PE:EtOAc=PE to 50:1 to 40:1 to 30:1) to afford A-6 (500.00 mg, 1.67 mmol) as a solid. $^1$H NMR (400 MHz, CDCl$_3$) δ$_H$ 8.28 (br s, 1H), 8.09 (d, 1H), 7.12 (d, 1H), 6.95 (dd, 1H), 4.04-3.89 (m, 2H).

Synthesis of A-7: A mixture of A-6 (400.00 mg, 1.34 mmol, 1.00 eq), Fe (748.39 mg, 13.40 mmol, 10.00 eq) and NH$_4$Cl (716.77 mg, 13.40 mmol, 468.48 mL, 10.00 eq) in EtOH (10.00 mL) and H$_2$O (10.00 mL) was stirred at 75° C. for 2 hours. The mixture was then filtered through Celite and eluted with EtOAc (50 mL×2), and the filtrate was concentrated to give an oil. The mixture was diluted with EtOAc (100 mL), washed with H$_2$O (20 mL×2) and brine (20 mL), dried over Na$_2$SO$_4$, filtered and concentrated to afford A-7 (390 mg) as an oil. LCMS R$_t$=0.726 min in 1.5 min chromatography, MS ESI calcd. for C$_8$H$_8$BrF$_3$N$_2$ [M+H]$^+$ 269.0, found 268.8.

Synthesis of A-8: To a mixture of A-7 (390 mg, 1.45 mmol, 1 eq) in HCl (1 M, 72.47 mL, 50 eq) was added a mixture of NaNO$_2$ (120.01 mg, 1.74 mmol, 94.50 μL, 1.2 eq) in H$_2$O (50 mL) at 0° C. The mixture was allowed to warm to 25° C. and stirred at 25° C. for 10 mins. The mixture was then basified with NaOH (1M) to pH=9, then extracted with EtOAc (50 mL×2). The combined organic phase was washed with brine (30 mL), dried over Na$_2$SO$_4$, filtered and concentrated. The crude product was purified by silica gel (PE:EtOAc=10:1) to afford A-8 (330 mg, 1.18 mmol) as a solid.

$^1$H NMR (400 MHz, CDCl$_3$) δ$_H$ 8.00 (d, 1H), 7.78 (s, 1H), 7.56 (dd, 1H), 5.21 (q, 2H).

Synthesis of Compound 2: A mixture of A-8 (100 mg, 357.09 μmol, 1 eq), [4-(trifluoromethoxy)phenyl]boronic acid (147.07 mg, 714.17 μmol, 2 eq), Pd(dppf)Cl$_2$.CH$_2$Cl$_2$ (58.32 mg, 71.42 μmol, 0.2 eq) and K$_2$CO$_3$ (98.70 mg, 714.17 μmol, 2 eq) in dioxane (5 mL) and H$_2$O (1 mL) was stirred at 90° C. for 16 hours. The mixture was then concentrated to and purified by Prep-HPLC to afford Compound 2 (101.27 mg, 279.61 μmol) as a solid. $^1$H NMR (400 MHz, CDCl$_3$) δ$_H$ 8.19 (d, 1H), 7.72-7.62 (m, 4H), 7.36 (d, 2H), 5.29 (q, 2H). LCMS R$_t$=1.260 min in 2.0 min chromatography, MS ESI calcd. for C$_{15}$H$_{10}$F$_6$N$_3$O [M+H]$^+$ 362.1, found 361.8.

Example 3: Synthesis of Compound 3

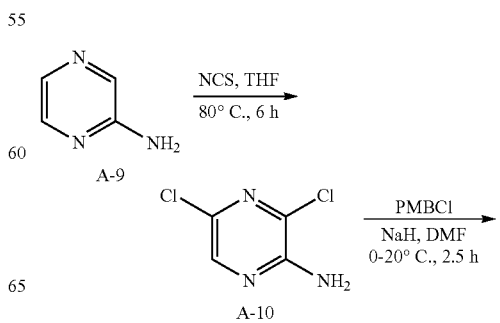

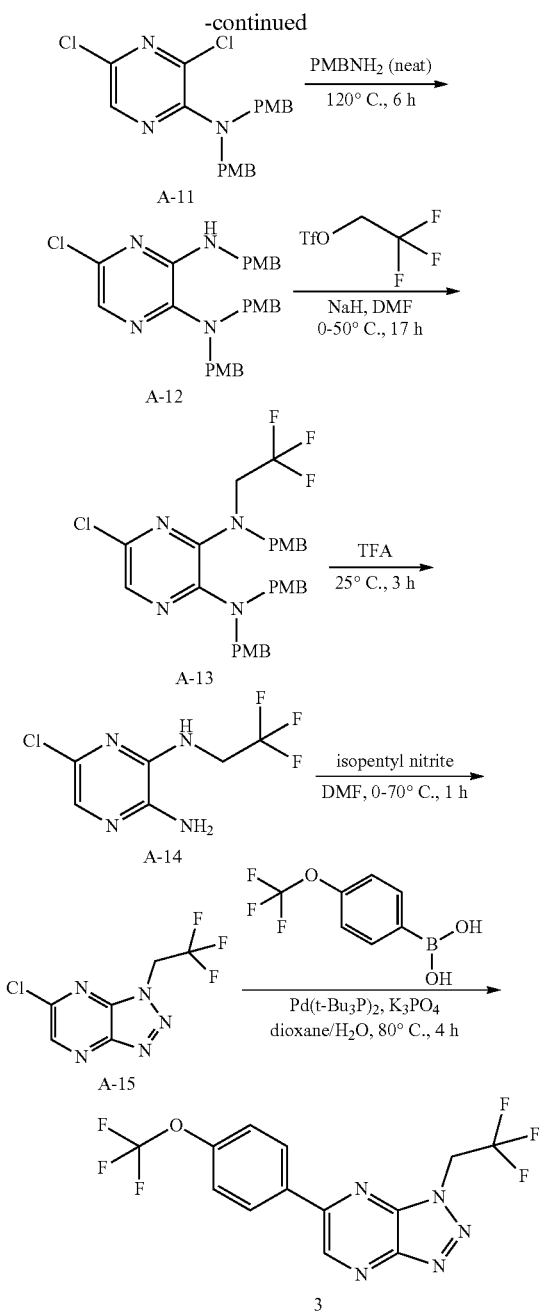

Synthesis of A-10: A mixture of A-9 (2 g, 21.03 mmol) and NCS (7.02 g, 52.58 mmol) in THF (60 mL) was stirred at 80° C. for 6 hours. The mixture was concentrated, and the residue was diluted with H$_2$O (30 mL) and extracted with EtOAc (50 mL×2). The combined organic phase was washed with water (20 mL×2) and brine (20 mL), dried over Na$_2$SO$_4$, filtered and concentrated. The crude product was purified by silica gel (EtOAc in PE=20% to 40% to 60%) to afford A-10 (3000 mg, 18.294 mmol) as a solid. $^1$H NMR (400 MHz, DMSO-d$_6$) δ$_H$ 8.08 (s, 1H), 7.05 (br s, 2H).

Synthesis of A-11: To a mixture of A-10 (3 g, 18.29 mmol) in DMF (30 mL) was added NaH (1.83 g, 45.73 mmol) at 0° C., then the mixture was stirred at 0° C. for 0.5 hour. 1-(chloromethyl)-4-methoxy-benzene (7.16 g, 45.73 mmol) was then added, and the mixture was stirred at 20° C. for 2 hours. The mixture was quenched with sat. NH$_4$Cl (100 mL), then extracted with EtOAc (200 mL×2). The combined organic phase was washed with water (50 mL×2) and brine (50 mL), dried over Na$_2$SO$_4$, filtered and concentrated. The crude product was purified by silica gel (EtOAc in PE=0% to 10% to 15%) to afford A-11 (5800 mg, 14.346 mmol) as an oil. $^1$H NMR (400 MHz, DMSO-d$_6$) δ$_H$ 8.34 (s, 1H), 7.18 (d, 4H), 6.87 (d, 4H), 4.51 (s, 4H), 3.71 (s, 6H).

Synthesis of A-12: A mixture of A-11 (5.5 g, 13.6 mmol) and (4-methoxyphenyl)methanamine (11.2 g, 81.62 mmol) was stirred at 120° C. for 6 hours. The mixture was then diluted with EtOAc (200 mL), and the combined organic phase was washed with 0.2 N HCl (30 mL×3), water (30 mL) and brine (30 mL), dried over Na$_2$SO$_4$, filtered and concentrated to give the crude product. The crude product was purified by silica gel (EtOAc in PE=0% to 10% to 15%) to afford A-12 (4500 mg, 8.9107 mmol) as an oil. $^1$H NMR (400 MHz, DMSO-d$_6$) δ$_H$ 7.43 (t, 1H), 7.33 (s, 1H), 7.24 (d, 2H), 7.07 (d, 4H), 6.86 (d, 2H), 6.81 (d, 4H), 4.50 (d, 2H), 4.16 (s, 4H), 3.71 (s, 3H), 3.71 (s, 6H).

Synthesis of A-13: To a mixture of A-12 (2.3 g, 4.55 mmol) in DMF (15 mL) was added NaH (546.52 mg, 13.66 mmol) at 0° C., then the mixture was stirred at 20° C. for 1 hour. 2,2,2-trifluoroethyl trifluoromethanesulfonate (3.17 g, 13.66 mmol) was then added, and the mixture was stirred at 50° C. for 16 hours. The mixture was quenched with sat. NH$_4$Cl (50 mL), then extracted with EtOAc (100 mL×2). The combined organic phase was washed with water (50 mL×2) and brine (50 mL), dried over Na$_2$SO$_4$, filtered and concentrated. The crude product was purified by purified by silica gel (EtOAc in PE=0% to 10% to 15%) to afford A-13 (500 mg, 0.3944 mmol, 9% yield) as an oil. LCMS R$_t$=1.057 min in 1.5 min chromatography, MS ESI calcd. for C$_{30}$H$_{31}$ClF$_3$N$_4$O$_3$ [M+H]$^+$ 587.2, found 587.3.

Synthesis of A-14: A mixture of A-13 (500 mg, 0.85 mmol) in TFA (20 mL, 85.17 mmol) was stirred at 25° C. for 3 hours. The mixture was concentrated, and the residue was diluted with H$_2$O (30 mL) and sat.NaHCO$_3$ (30 mL), and extracted with EtOAc (100 mL×2). The combined organic phase was washed with water (50 mL) and brine (50 mL), dried over Na$_2$SO$_4$, filtered and concentrated. The crude product was purified by Prep-TLC (PET/EtOAc=1/1) to afford A-14 (80 mg, 0.2425 mmol) as a solid. LCMS R$_t$=0.700 min in 1.5 min chromatography, MS ESI calcd. for C$_6$H$_7$ClF$_3$N$_4$ [M+H]$^+$ 227.0, found 226.8.

Synthesis of A-15: To a mixture of A-14 (75 mg, 0.30 mmol) in DMF (3 mL) was added isopentyl nitrite (70.59 mg, 0.60 mmol) at 0° C., then the mixture was stirred at 70° C. for 1 hour. The mixture was diluted with H$_2$O (15 mL), and the mixture was extracted with EtOAc (30 mL×2). The combined organic phase was washed with water (10 mL×2) and brine (10 mL), dried over Na$_2$SO$_4$, filtered and concentrated. The crude product was purified by Prep-TLC (PET/EtOAc=3/1) to afford A-15 (45 mg, 0.1646 mmol) as a solid. LCMS R$_t$=0.706 min in 1.5 min chromatography, MS ESI calcd. for C$_6$H$_4$ClF$_3$N$_5$ [M+H]$^+$ 238.0, found 237.9

Synthesis of Compound 3: A mixture of A-15 (50.71 mg, 0.25 mmol), Pd(t-Bu$_3$P)$_2$ (19.36 mg, 0.04 mmol) and K$_3$PO$_4$ (80.31 mg, 0.38 mmol) in 1,4-dioxane (4 mL) and water (0.40 mL) was stirred at 80° C. for 4 hours under N$_2$. The mixture was diluted with H$_2$O (15 mL) and extracted with EtOAc (30 mL×2). The combined organic phase was washed with water (10 mL×2) and brine (10 mL), dried over Na$_2$SO$_4$, filtered and concentrated. The crude product was purified by Prep-TLC (PET/EtOAc=3/1) afford Compound 3 (40.38 mg, 0.11 mmol) as a solid. $^1$H NMR (400 MHz, CDCl$_3$) δH 9.27 (s, 1H), 8.22 (d, 2H), 7.44 (d, 2H), 5.40 (q, 2H). LCMS $R_f$=1.311 min in 2.0 min chromatography, MS ESI calcd. for $C_{13}H_8F_6N_5O$ [M+H]$^+$ 364.1, found 364.0.

Example 4: Synthesis of Compound 4

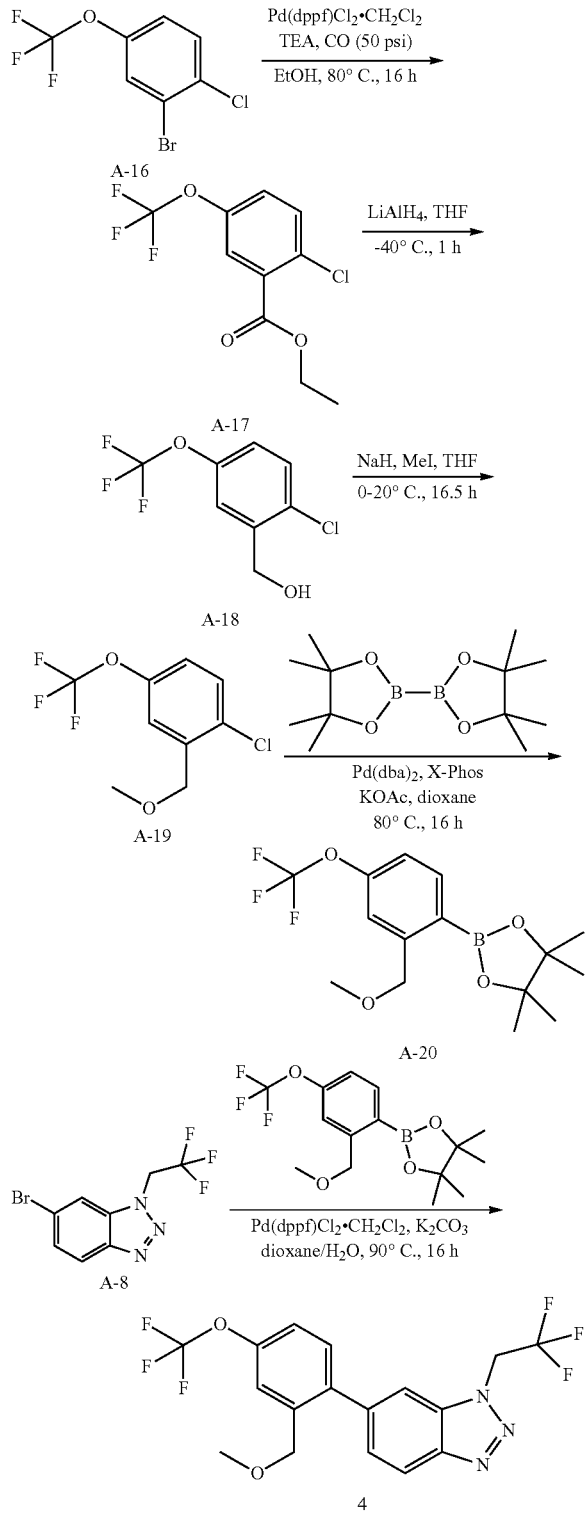

Synthesis of A-17: A mixture of 2-bromo-1-chloro-4-(trifluoromethoxy)benzene (5.00 g, 18.15 mmol), Pd(dppf) Cl$_2$·CH$_2$Cl$_2$ (1.48 g, 1.82 mmol) and Et$_3$N (7.55 mL, 54.45 mmol) in EtOH (30.00 mL) was degassed, and refilled with CO. The reaction was stirred under CO (50 psi) for 16 hours at 80° C. The reaction mixture was diluted with EtOH (20 mL), filtered through Celite, concentrated, and purified by flash chromatography on silica gel (EtOAc in PE=0%~5%) to afford A-17 (2.40 g, 8.93 mmol) as an oil. NMR (400 MHz, CDCl$_3$) $S_H$ 7.66-7.59 (m, 1H), 7.42 (d, 1H), 7.24-7.19 (m, 1H), 4.36 (q, 2H), 1.35 (t, 3H).

Synthesis of A-18: To a solution of A-17 (2.40 g, 8.93 mmol) in THF (30 mL) at -40° C. was added LiAlH$_4$ (406.67 mg, 10.72 mmol) slowly. The reaction was stirred at -40° C. for 1 hour. The reaction was quenched with sat.NH$_4$Cl (0.4 mL), diluted with EtOAc (30 mL), and the solid formed was filtered through Celite and eluted with EtOAc (30 mL). The filtrate was concentrated and purified by flash chromatography on silica gel (EtOAc in PE=0% to 10% to 20%) to afford A-18 (1.50 g, 6.62 mmol) as a solid. NMR (400 MHz, CDCl$_3$) $\delta_H$ 7.45-7.42 (m, 1H), 7.38 (d, 1H), 7.13-7.08 (m, 1H), 4.80 (d, 2H), 2.04 (t, 1H).

Synthesis of A-19: To a solution of A-18 (1.50 g, 6.62 mmol, 1.00 eq) in THF (20 mL) at 0° C. was added NaH (317.76 mg, 7.94 mmol, 60% purity) slowly. The mixture was stirred at 0° C. for 30 min, then MeI (1.24 mL, 19.86 mmol) was added, and the reaction was stirred at 20° C. for 16 hours. The reaction mixture was quenched with sat.NH$_4$Cl (50 mL), extracted with EtOAc (50 mL×3). The combined organic phase was washed with brine (50 mL), dried over Na$_2$SO$_4$, filtered, and concentrated, and the residue was purified by flash chromatography on silica gel (EtOAc in PE=0% to 5% to 10%) to afford A-19 (1.40 g, 5.82 mmol) as an oil. $^1$H NMR (400 MHz CDCl$_3$) $\delta_H$=7.43-7.32 (m, 2H), 7.09 (dd, 1H), 4.54 (s, 2H), 3.50 (s, 3H).

Synthesis of A-20: A mixture of A-19 (400.00 mg, 1.66 mmol), 4,4,5,5-tetramethyl-2-(4,4,5,5-tetramethyl-1,3,2-dioxaborolan-2-yl)-1,3,2-dioxaborolane (505.85 mg, 1.99 mmol), KOAc (325.82 mg, 3.32 mmol), X-Phos (197.84 mg, 415.00 μmol) and Pd$_2$(dba)$_3$ (152.01 mg, 166.00 μmol) in dioxane (6 mL) was stirred under N$_2$ at 80° C. for 16 hours. The mixture was cooled to room temperature, concentrated, and the residue was purified by flash chromatography on silica gel (PE:EtOAc=1:0 to 50:1) to afford A-20 (300.00 mg, 903.29 μmol) as an oil. LCMS $R_f$=0.99 min using Method B, MS ESI calcd. for $C_{15}H_{21}BF_3O_4$ [M+H]+ 333.1, found 332.7.

A mixture of 2-[2-(methoxymethyl)-4-(trifluoromethoxy) phenyl]-4,4,5,5-tetramethyl-1,3,2-dioxaborolane (189.76 mg, 0.57 mmol), A-8 (80 mg, 0.29 mmol), Pd(dppf) Cl$_2$·CH$_2$Cl$_2$ (46.66 mg, 0.06 mmol) and K$_2$CO$_3$ (78.97 mg, 0.5700 mmol) in 1,4-Dioxane (3 mL) and Water (0.5 mL) was stirred at 90° C. for 16 hours under N$_2$, at which point the desired product was observed by LCMS. The mixture was concentrated and purified by Prep-HPLC to afford Compound 4 (73.58 mg, 0.18 mmol) as an oil. $^1$H NMR (400 MHz, DMSO-d$_6$) $\delta_H$ 8.20 (d, 1H), 8.03 (s, 1H), 7.53-7.43 (m, 4H), 5.90 (q, 2H), 4.36 (s, 2H), 3.22 (s, 3H). LCMS $R_f$=1.356 min in 2.0 min chromatography, MS ESI calcd. for $C_{17}H_{14}F_6N_3O_2$ [M+H]$^+$ 406.1, found 405.9.

Example 5: Synthesis of Compound 5

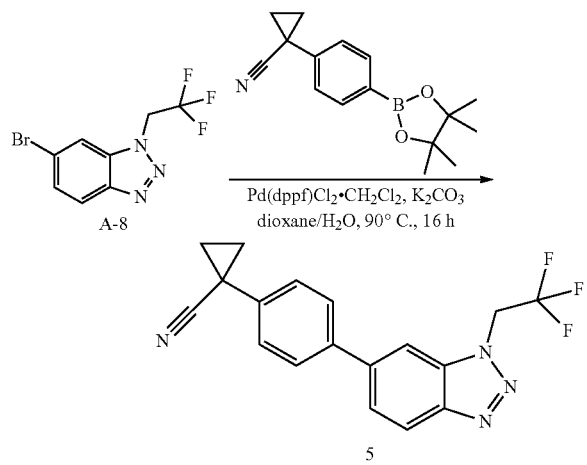

A mixture of A-8 (80 mg, 0.29 mmol), 1-[4-(4,4,5,5-tetramethyl-1,3,2-dioxaborolan-2-yl)phenyl]cyclopropanecarbonitrile (153.78 mg, 0.57 mmol), Pd(t-Bu$_3$P)$_2$ (29.2 mg, 0.06 mmol) and K$_3$PO$_4$ (121.28 mg, 0.57 mmol) in 1,4-dioxane (3 mL) and water (0.5 mL) was stirred at 80° C. for 16 hours under N$_2$. The crude product was concentrated and purified by Prep-HPLC to afford Compound 5 (20.66 mg, 0.06 mmol) as a solid. NMR (400 MHz, MeOD-d$_4$) δH 8.11 (d, 1H), 8.08 (s, 1H), 7.85-7.71 (m, 3H), 7.49 (d, 2H), 5.69 (q, 2H), 1.82-1.76 (m, 2H), 1.59-1.53 (m, 2H). LCMS R$_t$=1.140 min in 2.0 min chromatography, MS ESI calcd. for C$_{18}$H$_{14}$F$_3$N$_4$ [M+H]$^+$ 343.1, found 342.9.

Example 6: Synthesis of Compound 6

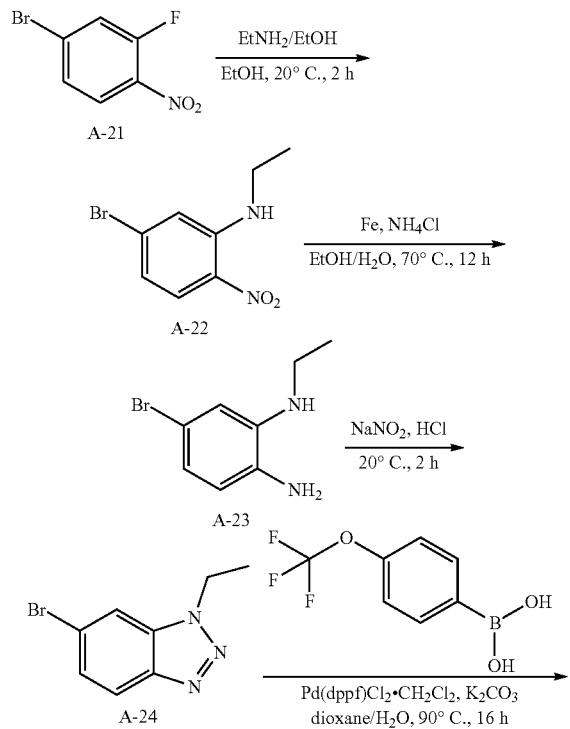

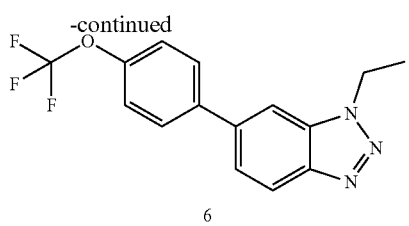

To a solution of 4-bromo-2-fluoro-1-nitro-benzene (2 g, 9.09 mmol) in Ethanol (15 mL) was added ethanamine (3725.62 mg, 27.27 mmol) and the mixture was stirred at 20° C. for 2 hours. The mixture was cooled to 0° C., the solid formed was collected by filtration, washed with i-Pr$_2$O (20 mL) and dried in oven to give the product of 5-bromo-N-ethyl-2-nitro-aniline (1950 mg, 7.96 mmol, 88% yield) as a solid. R$_t$=0.857 min in 1.5 min chromatography, MS ESI calcd. for C$_8$H$_{10}$BrN$_2$O$_2$ [M+H+2]$^+$ 247.0, found 246.8.

To a mixture of 5-bromo-N-ethyl-2-nitro-aniline (1 g, 4.08 mmol), NH$_4$Cl (2203.45 mg, 40.8 mmol) in Ethanol (10 mL) and Water (10 mL) was added Fe (2285.06 mg, 40.8 mmol), and the mixture was stirred at 70° C. for 2 hours. After cooling to r.t., the mixture was filtered through Celite and the filtrate was concentrated to give the residue. The residue was dissolved in water (20 mL), and the mixture was extracted with EtOAc (50 mL×2). The combined organic phase was washed with brine (10 mL), dried over Na$_2$SO$_4$, filtered and concentrated to give the crude product (930 mg, 4.0691 mmol) as a solid. R$_t$=0.609 min in 1.5 min chromatography, MS ESI calcd. for C$_8$H$_{11}$BrN$_2$ [M+H+2]$^+$ 217.0, found 216.8.

To a solution of 4-bromo-N2-ethyl-benzene-1,2-diamine (930 mg, 4.32 mmol) in HCl (20 mL, 4.65 mmol) was added NaNO$_2$ (358.01 mg, 5.19 mmol), and the mixture was stirred at 20° C. for 2 hours. The mixture was concentrated, diluted with H$_2$O (15 mL), and extracted with EtOAc (50 mL×2). The combined organic phase was washed with brine (15 mL), dried over Na$_2$SO$_4$, filtered and concentrated to give the crude product. The crude product was purified by Combi-flash (EtOAc in PE=10% to 20% to 40% to 60%) to give the product (560 mg, 2.4375 mmol) as a solid. R$_t$=0.737 min in 1.5 min chromatography, MS ESI calcd. for C$_8$H$_9$BrN$_3$ [M+H]$^+$ 226.0, found 225.9.

A mixture of [4-(trifluoromethoxy)phenyl]boronic acid (327.93 mg, 1.59 mmol), 6-bromo-1-ethyl-benzotriazole (300 mg, 1.33 mmol), Pd(dppf)Cl$_2$·CH$_2$Cl$_2$ (216.73 mg, 0.27 mmol) and K$_2$CO$_3$ (366.26 mg, 2.65 mmol) in 1,4-Dioxane (6 mL) and Water (0.50 mL) was stirred at 90° C. for 16 hours. The mixture was concentrated to give a crude product. The crude product was purified by Prep-HPLC (water (0.05% ammonia hydroxide v/v)-ACN) to give compound 6 (158.69 mg, 0.52 mmol) as a solid. $^1$H NMR DMSO-d$_6$ 400 MHz δ=8.23 (s, 1H), 8.12 (d, 1H), 7.94 (d, 2H), 7.73 (dd, 1H), 7.52 (d, 2H), 4.80 (q, 2H), 1.54 (t, 3H). LCMS R$_t$=1.435 min in 2.0 min chromatography, MS ESI calcd. for C$_{15}$H$_{13}$F$_3$N$_3$O [M+H]$^+$ 308.1, found 307.9.

Example 7: Synthesis of Compound 7

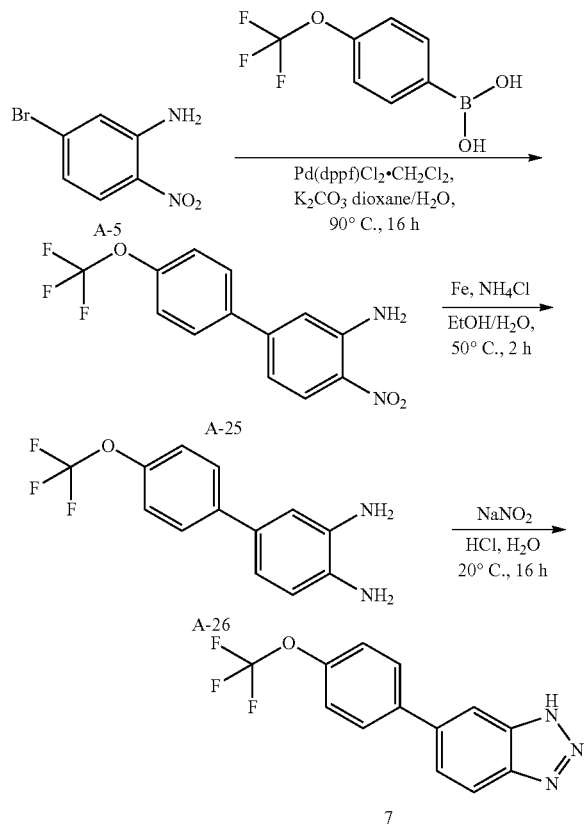

A mixture of 5-bromo-2-nitro-aniline (500 mg, 2.3 mmol), [4-(trifluoromethoxy)phenyl]boronic acid (569.34 mg, 2.76 mmol), $K_2CO_3$ (636.81 mg, 4.61 mmol), and Pd(dppf)Cl$_2$·CH$_2$Cl$_2$ (376.3 mg, 0.46 mmol) in 1,4-Dioxane (10 mL) and Water (2 mL) was stirred at 90° C. for 16 hours. After cooling to r.t., the mixture was concentrated to give the crude product. The crude product was purified by silica gel column (EtOAc in PE=20% to 40% to 60%) to give the product (600 mg, 2.01 mmol) as a solid. LCMS $R_t$=0.894 min in 1.5 min chromatography, MS ESI calcd. for $C_{13}H_{10}F_3N_2O_3$ [M+H]$^+$299.1, found 298.9.

To a solution of 2-nitro-5-[4-(trifluoromethoxy)phenyl] aniline (300 mg, 1.01 mmol), Fe (563.34 mg, 10.06 mmol) in Ethanol (10 mL), Water (10 mL) was added NH$_4$Cl (593.52 mg, 10.06 mmol), and the mixture was stirred at 50° C. for 2 hours. After cooling to r.t., the mixture was filtered through Celite and the filtrate was concentrated to give the residue. The residue was dissolved in water (15 mL) and extracted with EtOAc (50 mL×2). The combined organic phase was washed with brine (10 mL), dried over Na$_2$SO$_4$, filtered and concentrated to give the crude product (280 mg, 1.04 mmol, crude) as a solid. LCMS $R_t$=0.727 min in 1.5 min chromatography, 5-95AB, MS ESI calcd. for $C_{13}H_{12}F_3N_2O$ [M+H]$^+$269.1, found 268.9.

To a solution of 4-[4-(trifluoromethoxy)phenyl]benzene-1,2-diamine (180 mg, 0.67 mmol) in HCl (5 mL, 0.67 mmol) was added NaNO$_2$ (55.56 mg, 0.8100 mmol), and the mixture was stirred at 20° C. for 16 hours. The mixture was poured into water (20 mL), extracted with EtOAc (20 mL×2). The combined organic phase was washed with brine (10 mL), dried over Na$_2$SO$_4$, filtered and concentrated to give the crude product. The crude product was purified by Prep-HPLC (water (0.05% ammonia hydroxide v/v)-ACN) to give compound 7 (26.66 mg, 0.0951 mmol) as a solid. $^1$H NMR DMSO-d$_6$ 400 MHz δ=8.17 (s, 1H), 8.01 (d, 1H), 7.90 (d, 2H), 7.76 (d, 1H), 7.49 (d, 2H). LCMS $R_t$=1.324 min in 2.0 min chromatography, MS ESI calcd. for $C_{13}H_9F_3N_3O$ [M+H]$^+$ 280.1, found 279.8.

Example 8: Synthesis of Compound 8

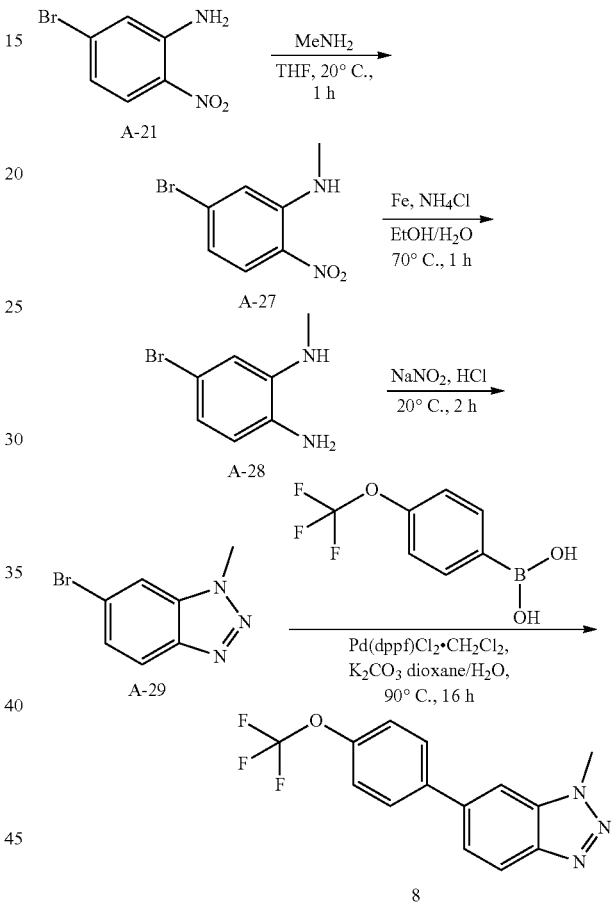

To a solution of 4-bromo-2-fluoro-1-nitro-benzene (1 g, 4.55 mmol) in THF (15 mL) was added methanamine (6.82 mL, 13.64 mmol) (2 M solution in THF), and the mixture was stirred at 20° C. for 2 hours.

The mixture was concentrated to give the crude product (1200 mg, 4.97 mmol) as a solid. LCMS $R_t$=0.815 min in 1.5 min chromatography, MS ESI calcd. for $C_7H_8BrN_2O_2$ [M+H]$^+$ 231.0, found 230.7.

To a mixture of 5-bromo-N-methyl-2-nitro-aniline (1.2 g, 5.19 mmol) and Fe (2908.46 mg, 51.94 mmol) in Ethanol (10 mL) and Water (10 mL) was added ammonia hydrochloride (2778.1 mg, 51.94 mmol), and the mixture was stirred at 70° C. for 1 hour. After cooling to r.t., the mixture was filtered through Celite and the filtration was concentrated to give the residue. The residue was dissolved in water (20 mL), and the mixture was extracted with EtOAc (50 mL×2). The combined organic phase was washed with brine (10 mL), dried over Na$_2$SO$_4$, filtered and concentrated to give the crude product (960 mg, 4.7747 mmol) as an oil. LCMS $R_t$=0.356 min in 1.5 min chromatography, MS ESI calcd. for $C_7H_{10}BrN_2$ [M+H]$^+$ 201.0, found 200.8.

To a solution of 4-bromo-N2-methyl-benzene-1,2-diamine nitrite (960 mg, 3.55 mmol) in HCl (20 mL, 1M, 20 mmol) was added NaNO$_2$ (411 mg, 5.2 mmol), and the mixture was stirred at 20° C. for 2 hours.

The mixture was poured into water (20 mL), extracted with EtOAc (50 mL×2). The combined organic phase was washed with brine (10 mL), dried over Na$_2$SO$_4$, filtered and concentrated to give the crude product. The crude product was purified by silica gel column (EtOAc in PE=20% to 40% to 60%) to give the product (500 mg, 2.26 mmol) as a solid. LCMS $R_t$=0.700 min in 1.5 min chromatography, MS ESI calcd. for $C_7H_7BrN_3$ [M+H+2]$^+$ 214.0, found 213.7.

A mixture of 6-bromo-1-methyl-benzotriazole (200 mg, 0.9400 mmol), [4-(trifluoromethoxy)phenyl]boronic acid (233.07 mg, 1.13 mmol), K$_2$CO$_3$ (260.32 mg, 1.89 mmol) and Pd(dppf)Cl$_2$.CH$_2$Cl$_2$ (154.04 mg, 0.19 mmol) in 1,4-Dioxane (6 mL) and Water (0.50 mL) was stirred at 90° C. for 16 hours. After cooling to r.t., the mixture was concentrated to give the crude product. The crude product was purified by Prep-HPLC (water (0.05% ammonia hydroxide v/v)-ACN) to give compound 8 (103.5 mg, 0.35 mmol) as a solid. $^1$H NMR (400 MHz, DMSO-d$_6$) $\delta_H$ 8.19 (s, 1H), 8.12 (d, 1H), 7.93 (d, 2H), 7.73 (d, 1H), 7.52 (d, 2H), 4.36 (s, 3H). LCMS $R_t$=1.150 min in 2.0 min chromatography, MS ESI calcd. for $C_{14}H_uF_3N_3O$ [M+H]$^+$ 294.1, found 293.9.

Example 9: Synthesis of Compound 9

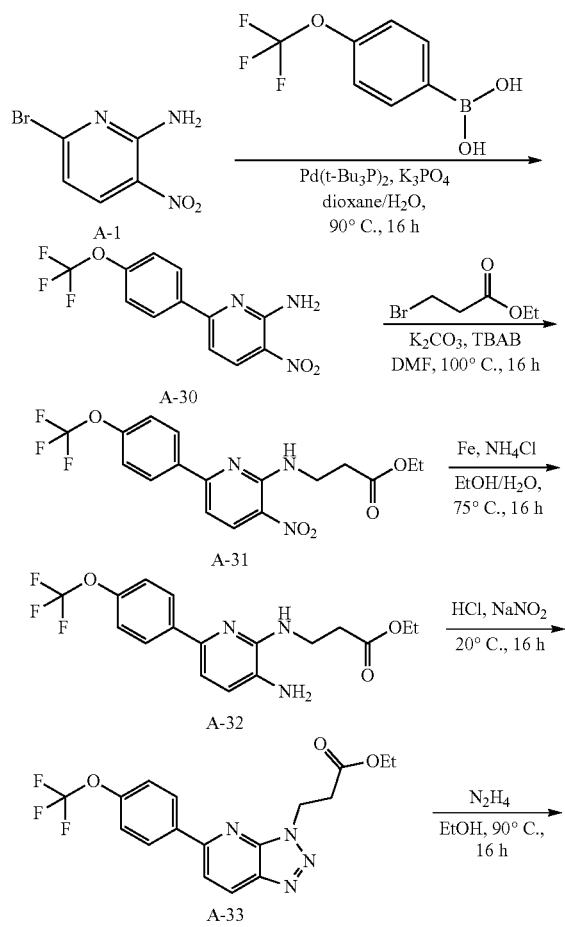

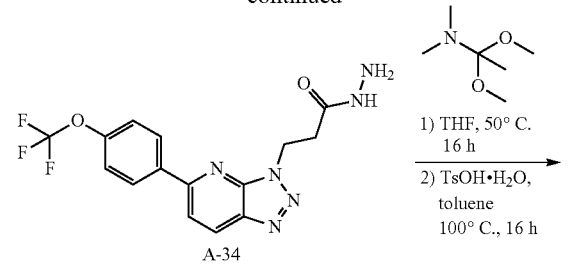

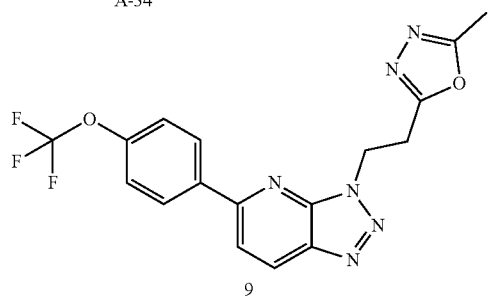

A mixture of (4-(trifluoromethoxy)phenyl)boronic acid (708.44 mg, 3.44 mmol, 1.5 eq), 6-bromo-3-nitro-pyridin-2-amine (500 mg, 2.29 mmol, 1 eq), Pd(t-Bu$_3$P)$_2$ (234.42 mg, 458.70 µmol, 0.2 eq) and K$_3$PO$_4$ (973.68 mg, 4.59 mmol, 2 eq) in dioxane (25 mL) and H$_2$O (5 mL) was stirred at 80° C. for 16 hours. After cooling to r.t, the mixture was concentrated and diluted with H$_2$O (50 mL) and extracted with EtOAc (50 mL×2). The combined organic phase was washed with H$_2$O (50 mL) and brine (30 mL), dried over Na$_2$SO$_4$, filtered and concentrated to give the product (1.17 g, crude) as a solid. LCMS $R_t$=0.869 min in 1.5n chromatography, MS ESI calcd. for $C_{12}H_9F_3N_3O_3$ [M+H]$^+$ 300.1, found 299.9.

A mixture of ethyl 3-bromopropanoate (302.51 mg, 1.67 mmol), 3-nitro-6-[4-(trifluoromethoxy)phenyl]pyridin-2-amine (500.00 mg, 1.67 mmol), K$_2$CO$_3$ (230.96 mg, 1.67 mmol) and tetrabutylammonium bromide (53.88 mg, 0.17 mmol) in DMF (25 mL) was stirred at 100° C. for 16 hours. The mixture was diluted with H$_2$O (50 mL) and extracted with EtOAc (50 mL×2). The combined organic phase was washed with brine (30 mL), dried over Na$_2$SO$_4$, filtered and concentrated to give the crude product. The crude product was purified by silica gel column (EtOAc in PE=0 to 40% to 100%) to give the product (330 mg, 0.82 mmol) as a solid. LCMS $R_t$=0.970 min in 1.5 min chromatography, MS ESI calcd. for $C_{17}H_{17}F_3N_3O_5$ [M+H]$^+$ 400.1, found 400.0.

A mixture of ethyl 3-[[3-nitro-6-[4-(trifluoromethoxy)phenyl]-2-pyridyl]amino]propanoate (300 mg, 0.75 mmol), Fe (419.59 mg, 7.51 mmol) and NH$_4$Cl (401.86 mg, 7.51 mmol) in Ethanol (10 mL) and Water (10 mL) was stirred at 75° C. for 16 hours. After cooling to r.t, the mixture was filtrated through Celite, and eluted with EtOAc (20 mL×2). The filtration was concentrated and diluted with EtOAc (30 mL), washed with water (10 mL×2) and brine (10 mL), dried over Na$_2$SO$_4$, filtered and concentrated to give the crude product (230 mg, 0.62 mmol) as an oil. The product was used for next step without further purification. LCMS $R_t$=0.768 min in 1.5 min chromatography, MS ESI calcd. for $C_{17}H_{19}F_3N_3O_3$ [M+H]$^+$ 370.1, found 370.1.

To a mixture of ethyl 3-[[3-amino-6-[4-(trifluoromethoxy)phenyl]-2-pyridyl]amino]propanoate (230 mg, 0.62 mmol) in HCl (1 M, 5 mL) was added NaNO$_2$ (51.56 mg, 0.75 mmol) at 0° C. The mixture was allowed to warm to room temperature and stirred for 16 hours. The reaction mixture was neutralized carefully with Na₂CO₃ (solid) to pH=7. The mixture was diluted with H₂O (10 mL) and extracted with EtOAc (10 mL×2). The combined organic phase was washed with brine (10 mL), dried over Na₂SO₄, filtered and concentrated to give the product. The crude product was purified by silica gel column (EtOAc in PE=0% to 50% to 100%) to give the product (150 mg, 0.39 mmol) as an oil. LCMS $R_t$=0.903 min in 1.5 min chromatography, MS ESI calcd. for $C_{17}H_{16}F_3N_4O_3$ [M+H]⁺ 381.1, found 381.0.

A mixture of ethyl 3-[5-[4-(trifluoromethoxy)phenyl]triazolo[4,5-b]pyridin-3-yl]propanoate (150 mg, 0.39 mmol) and hydrazine (63.2 mg, 1.97 mmol) in Ethanol (10 mL) was stirred at 90° C. for 16 hours. After cooling to r.t, the mixture was concentrated to give the crude product (150 mg, 0.35 mmol) as an oil. The product was used for next step without further purification. LCMS $R_t$=0.729 min in 1.5 min chromatography, MS ESI calcd. for $C_{15}H_{14}F_3N_6O_2$ [M+H]⁺ 367.1, found 367.0.

To a mixture of 3-[5-[4-(trifluoromethoxy)phenyl]triazolo[4,5-b]pyridin-3-yl]propanehydrazide (150 mg, 0.41 mmol) in THF (10 mL) was added 1,1-dimethoxy-N,N-dimethylethanamine (81.81 mg, 0.61 mmol). The resulting mixture was then stirred at 50° C. under N₂ for 16 hours to give a solution. The solution was concentrated to give a residue as foam. The foam was dissolved in anhydrous Toluene (10 mL) and then TsOH.H₂O (7.79 mg, 0.04 mmol) was added. The mixture was stirred at 100° C. for another 16 hours. After cooling to r.t, the mixture was concentrated to give the crude product. The crude product was purified by Prep-HPLC (column: Phenomenex Gemini C18 250*50 10u; mobile phase: [water(0.1% TFA)-ACN]; B %: 40%-70%, 8 min) to give compound 9 (16.21 mg, 0.04 mmol) as a solid. ¹H NMR (400 MHz, CDCl₃) $δ_H$/8.45 (d, 1H), 8.19-8.09 (m, 2H), 7.82 (d, 1H), 7.38 (d, 2H), 5.25 (t, 2H), 3.68 (t, 2H), 2.43 (s, 3H). LCMS $R_t$=1.253 min in 2.0 min chromatography, MS ESI calcd. for $C_{17}H_{14}F_3N_6O_2$ [M+H]⁺ 391.1, found 391.0.

Example 10: Synthesis of Compound 10

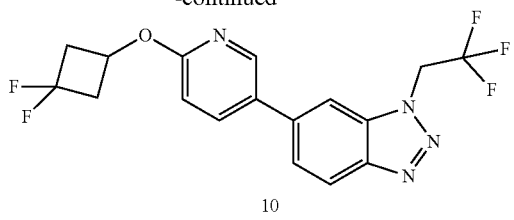

A mixture of 6-bromo-1-(2,2,2-trifluoroethyl)benzotriazole (300 mg, 1.07 mmol), (6-fluoro-3-pyridyl)boronic acid (226.43 mg, 1.61 mmol), Pd(dppf)Cl₂.CH₂Cl₂ (131.23 mg, 0.16 mmol) and K₂CO₃ (296.12 mg, 2.14 mmol) in 1,4-Dioxane (10 mL) and Water (2 mL) was stirred at 85° C. for 12 hours under N₂. After cooling to r.t., the mixture was concentrated. The residue was diluted with H₂O (20 mL), and the mixture was extracted with EtOAc (30 mL×2). The combined organic phase was washed with water (10 mL×2) and brine (10 mL), dried over Na₂SO₄, filtered and concentrated to give the crude product. The crude product was purified by silica gel column (EtOAc in PE=10% to 25% to 50%) to give the product (270 mg, 0.91 mmol) as a solid. ¹H NMR (400 MHz, DMSO-d₆) $δ_H$ 8.68 (d, 1H), 8.43 (s, 1H), 8.42-8.37 (m, 1H), 8.25 (d, 1H), 7.86 (dd, 1H), 7.40 (dd, 1H), 5.92 (q, 2H). LCMS $R_t$=0.773 min in 1.5 min chromatography, MS ESI calcd. for $C_{13}H_9F_4N_4$ [M+H]⁺ 297.1, found 296.9.

To a mixture of 3,3-difluorocyclobutanol (43.79 mg, 0.41 mmol) in THF (3 mL) was added NaH (21.61 mg, 0.54 mmol) at 0° C., then the mixture was stirred at 0° C. for 10 mins. To the mixture was added 6-(6-fluoro-3-pyridyl)-1-(2,2,2-trifluoroethyl)benzotriazole (80 mg, 0.27 mmol), then the mixture was stirred at 20° C. for 2 hours. The mixture was quenched with sat.NH₄Cl (10 mL), and then the mixture was extracted with EtOAc (20 mL×2). The combined organic phase was washed with brine (15 mL), dried over Na₂SO₄, filtered and concentrated to give the crude product. The crude product was purified by Prep-TLC (PET/EtOAc=2/1) to give compound 10 (15.76 mg, 0.0410 mmol) as a solid. ¹H NMR (400 MHz, CDCl₃) $δ_H$ 8.42 (d, 1H), 8.19 (d, 1H), 7.88 (dd, 1H), 7.64 (s, 1H), 7.61 (dd, 1H), 6.90 (d, 1H), 5.28 (q, 2H), 5.24-5.18 (m, 1H), 3.23-3.11 (m, 2H), 2.85-2.71 (m, 2H). LCMS $R_t$=1.292 min in 2.0 min chromatography, MS ESI calcd. for $C_{17}H_{14}F_5N_4O$ [M+H]⁺ 385.1, found 385.1.

Example 11: Synthesis of Compound 11

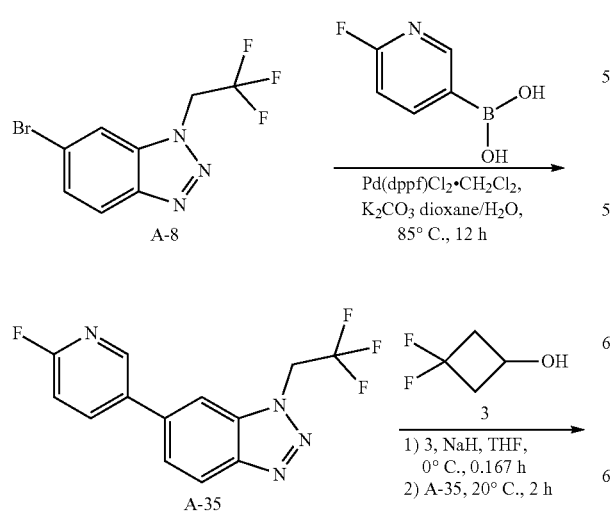

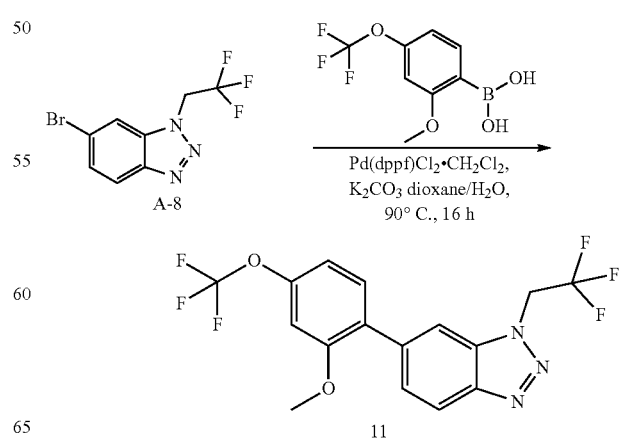

To a solution of 6-bromo-1-(2,2,2-trifluoroethyl)benzotriazole (100 mg, 0.36 mmol) in 1,4-Dioxane (2 mL) and Water Water (0.20 mL) was added [2-methoxy-4-(trifluoromethoxy)phenyl]boronic acid (101.11 mg, 0.43 mmol), Pd(pddf)Cl$_2$.CH$_2$Cl$_2$ (43.74 mg, 0.05 mmol) and K$_2$CO$_3$ (98.7 mg, 0.71 mmol). The resulting mixture was stirred at 90° C. under N$_2$ for 16 hours to give a suspension. The reaction mixture was cooled to room temperature and filtered through Celite. The filtrate was concentrated to give a crude product. The crude product was purified by Prep-HPLC (water (0.05% ammonia hydroxide v/v)-ACN) to give compound 11 (96.42 mg, 0.25 mmol) as a solid. $^1$H NMR (400 MHz, CDCl$_3$) $\delta_H$ 8.13 (d, 1H), 7.68 (s, 1H), 7.57 (dd, 1H), 7.38 (d, 1H), 6.96 (d, 1H), 6.88 (s, 1H), 5.26 (q, 2H), 3.85 (s, 3H). LCMS R$_t$=1.340 min in 2.0 min chromatography, MS ESI calcd. for C$_{16}$H$_{12}$F$_6$N$_3$O$_2$ [M+H]$^+$ 392.1, found 392.0.

Example 12: Synthesis of Compound 12

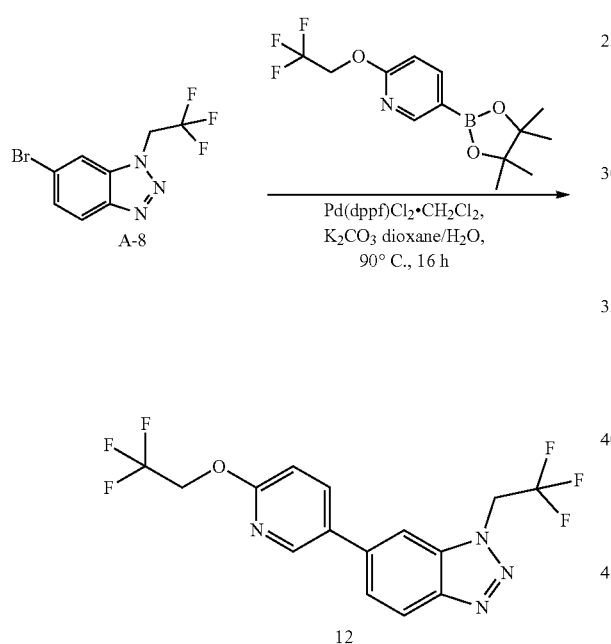

To a solution of 6-bromo-1-(2,2,2-trifluoroethyl)benzotriazole (100 mg, 0.36 mmol) in 1,4-Dioxane (2 mL) and Water (0.20 mL) was added 5-(4,4,5,5-tetramethyl-1,3,2-dioxaborolan-2-yl)-2-(2,2,2-trifluoroethoxy)pyridine (129.88 mg, 0.43 mmol), Pd(dppf)Cl$_2$.CH$_2$Cl$_2$ (43.74 mg, 0.05 mmol) and K$_2$CO$_3$ (98.7 mg, 0.71 mmol). The resulting mixture was stirred at 90° C. under N$_2$ for 16 hours to give a suspension The reaction mixture was cooled to room temperature and filtered through Celite. The filtrate was concentrated to give a crude product. The crude product was purified by Prep-HPLC (water (0.05% ammonia hydroxide v/v)-ACN) to give compound 12 (57.49 mg, 0.15 mmol) as a solid. $^1$H NMR (400 MHz, CDCl$_3$) $\delta_H$ 8.43 (d, 1H), 8.20 (d, 1H), 7.93 (dd, 1H), 7.66 (s, 1H), 7.62 (d, 1H), 7.02 (d, 1H), 5.29 (q, 2H), 4.85 (q, 2H). LCMS R$_t$=1.278 min in 2.0 min chromatography, MS ESI calcd. for C$_{15}$H$_{11}$F$_6$N$_4$O [M+H]$^+$ 377.1, found 377.0.

Example 13: Synthesis of Compound 13

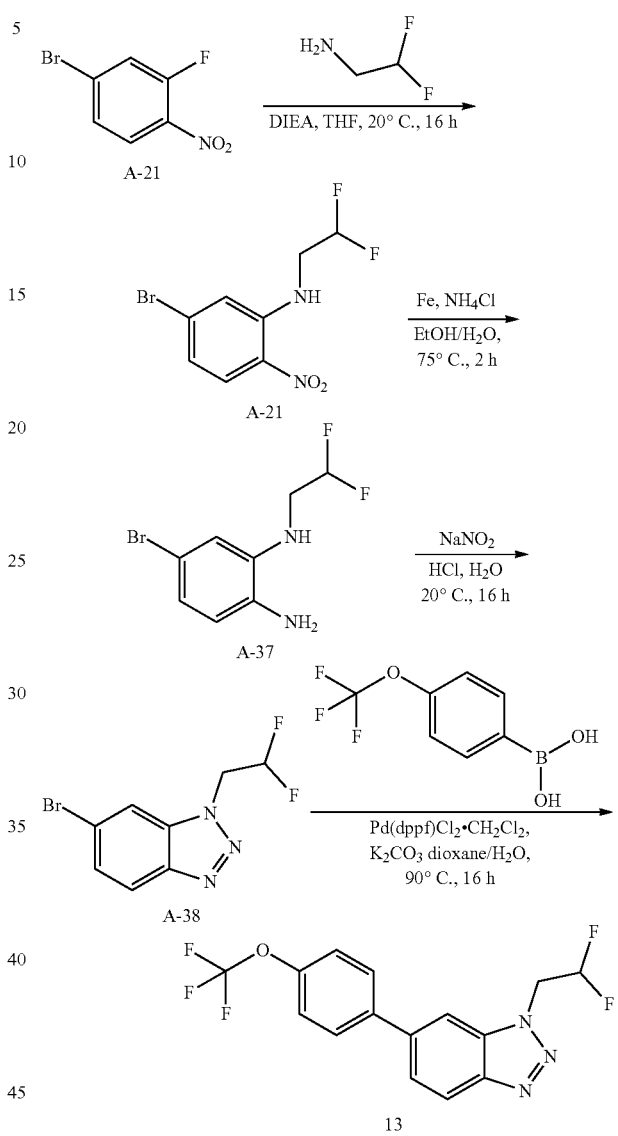

To a solution of 2,2-difluoroethanamine (552.68 mg, 6.82 mmol) and DIEA (1172.73 mg, 9.09 mmol) in THF (3 mL) was added 4-bromo-2-fluoro-1-nitro-benzene (1000 mg, 4.55 mmol) slowly and the solution was stirred at 20° C. for 16 hours. The mixture was concentrated to remove most of THF, and the residue was dissolved in EtOAc (10 mL), neutralized with sat.NaHCO$_3$ to pH=8-9. The mixture was extracted with EtOAc (10 mL×2). The combined organic phase was washed with brine (10 mL), dried over Na$_2$SO$_4$, filtered and concentrated to give the crude product (1200 mg, 4.27 mmol) as a solid. $^1$H NMR (400 MHz, CDCl$_3$) $\delta_H$ 8.21 (br s, 1H), 8.07 (d, 1H), 7.09 (d, 1H), 6.89 (dd, 1H), 6.17-5.85 (m, 1H), 3.81-3.70 (m, 2H).

To the mixture of 5-bromo-N-(2,2-difluoroethyl)-2-nitroaniline (1200 mg, 4.27 mmol) in Ethanol (5 mL) and Water (5 mL) was added NH$_4$Cl (2284.29 mg, 42.7 mmol) and Fe (2391.03 mg, 42.7 mmol) and the mixture was stirred at 75° C. for 2 hours. The mixture was filtered through Celite. The filtrate was concentrated to remove most of the EtOH and water. The residue was diluted with H₂O (10 mL), extracted with EtOAc (20 mL×2). The combined organic phase was washed with brine (10 mL), dried over Na₂SO₄, filtered and concentrated to give the product (1000 mg, 3.98 mmol) as a solid. $^1$H NMR (400 MHz, CDCl₃) $\delta_H$ 6.85 (dd, 1H), 6.77 (d, 1H), 6.62 (d, 1H), 6.15-5.82 (m, 1H), 3.67 (br s, 1H), 3.55-3.45 (m, 2H), 3.34 (br s, 2H).

To the mixture of 4-bromo-N-2-(2,2-difluoroethyl)benzene-1,2-diamine (1000 mg, 3.98 mmol) in 1N HCl (20 mL, 20 mmol) was added NaNO₂ (329.79 mg, 4.78 mmol), and the mixture was stirred at 20° C. for 16 hours. The mixture was basified with sat.NaHCO₃ to pH=8-9. Then the mixture was extracted with EtOAc (20 mL×2). The combined organic phase was washed with brine (10 mL), dried over Na₂SO₄, filtered and concentrated to give the crude product. The crude product was purified by silica gel column (PE:EtOAc=5:1 to 1:1) to give the product (700 mg, 2.67 mmol) as a solid. $^1$H NMR (400 MHz, CDCl₃) $\delta_H$ 7.97 (d, 1H), 7.79 (s, 1H), 7.54 (dd, 1H), 6.39-6.06 (m, 1H), 4.98 (dt, 2H).

A mixture of 6-bromo-1-(2,2-difluoroethyl)benzotriazole (150 mg, 0.57 mmol), [4-(trifluoromethoxy)phenyl]boronic acid (141.45 mg, 0.69 mmol), Pd(dppf)Cl₂·CH₂Cl₂ (70.06 mg, 0.09 mmol) and Cs₂CO₃ (372.07 mg, 1.14 mmol) in 1,4-Dioxane (2 mL) and Water (0.20 mL) was stirred at 90° C. for 16 hours. The mixture was cooled to r.t., diluted with EtOAc (5 mL), filtered through silica gel, eluted with EtOAc (5 mL) and concentrated to give the crude product. The crude product was purified by silica gel column (PE:EtOAc=5:1 to 3:1) to give compound 13 (162.95 mg, 0.47 mmol) as a solid. $^1$H NMR (400 MHz, CDCl₃) δH 8.16 (d, 1H), 7.70 (s, 1H), 7.68 (d, 2H), 7.63 (dd, 1H), 7.36 (d, 2H), 6.42-6.10 (m, 1H), 5.06 (dt, 2H). LCMS $R_t$=1.269 min in 2.0 min chromatography, MS ESI calcd. for $C_{15}H_{11}F_5N_3O$ [M+H]⁺ 344.1, found 344.0.

Example 14: Synthesis of Compound 14 mmol), (4-hydroxyphenyl)boronic acid (258.58 mg, 1.87 mmol) and K₂CO₃ (345.48 mg, 2.5 mmol) in 1,4-Dioxane (10 mL) and Water (2 mL) was stirred at 85° C. for 12 hours. After cooling to r.t., the mixture was concentrated. The residue was diluted with H₂O (20 mL), and the mixture was extracted with EtOAc (50 mL×2). The combined organic phase was washed with water (10 mL×2) and brine (10 mL), dried over Na₂SO₄, filtered and concentrated to give the crude product. The crude product was purified by silica gel column (EtOAc in PE=10% to 20% to 45%) to give the product A-39 (320 mg, 1.07 mmol) as a solid. $^1$H NMR (400 MHz, DMSO-d₆) $\delta_H$ 9.73 (s, 1H), 8.19 (s, 1H), 8.12 (d, 1H), 7.73 (dd, 1H), 7.63 (d, 2H), 6.91 (d, 2H), 5.90 (q, 2H). LCMS $R_t$=0.751 min in 1.5 min chromatography, MS ESI calcd. for $C_{14}H_{11}F_3N_3O$ [M+H]⁺ 294.1, found 293.9.

To a mixture of 4-[3-(2,2-trifluoroethyl)benzotriazol-5-yl]phenol (120 mg, 0.41 mmol), 3,3-difluorocyclobutanol (88.47 mg, 0.82 mmol) and Ph₃P (322.02 mg, 1.23 mmol) in THF (5 mL) was added DEAD (213.8 mg, 1.23 mmol) under N₂ at 0° C., then the mixture was stirred at 65° C. for 24 hours. After cooling to r.t., the mixture was concentrated to give the crude product. The crude product was purified by silica gel column (EtOAc in PE=5% 20 to 10% to 20%) to give the impure product. The impure product was purified by Prep-TLC (PET/EtOAc=2/1) to give compound 14 (14.69 mg, 0.037 mmol) as a solid. $^1$H NMR (400 MHz, CDCl₃) $\delta_H$ 8.15 (d, 1H), 7.67-7.62 (m, 2H), 7.59 (d, 2H), 6.94 (d, 2H), 5.27 (q, 2H), 4.79-4.66 (m, 1H), 3.22-3.08 (m, 2H), 2.90-2.75 (m, 2H). LCMS $R_t$=1.306 min in 2.0 min chromatography, MS ESI calcd. for $C_{18}H_{15}F_5N_3O$ [M+H]⁺ 384.1, found 384.0.

Example 15: Synthesis of Compound 15

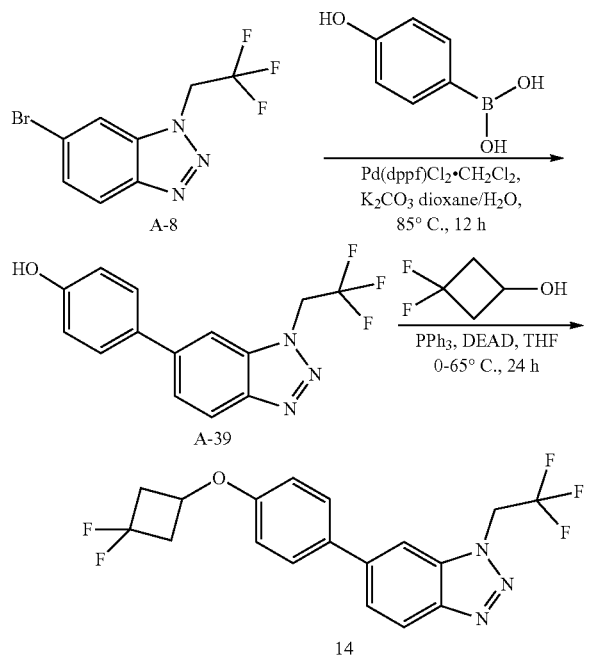

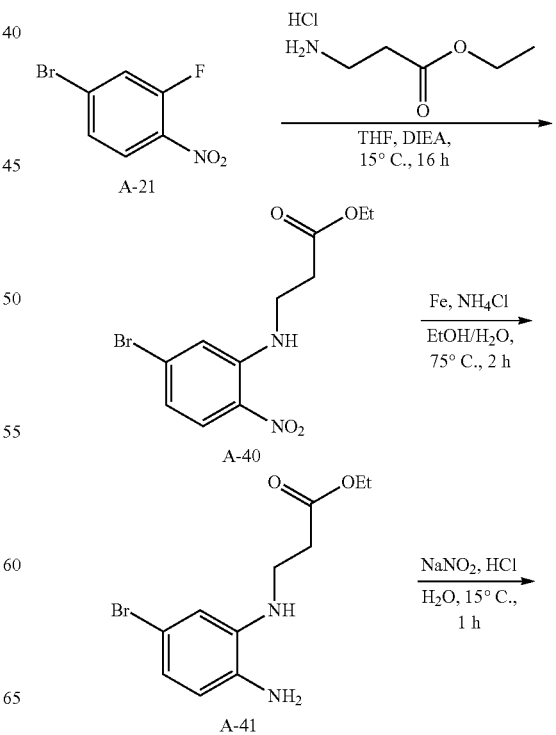

A mixture of Pd(dppf)Cl₂·CH₂Cl₂ (153.1 mg, 0.19 mmol), 6-bromo-1-(2,2-trifluoroethyl)benzotriazole (350 mg, 1.25

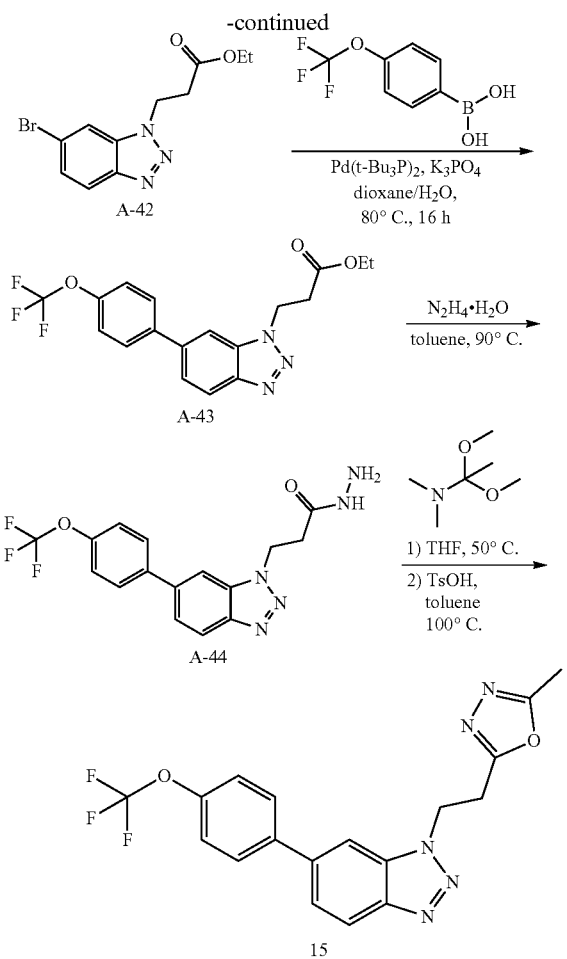

To a solution of 4-bromo-2-fluoro-1-nitro-benzene (2 g, 9.09 mmol) in THF (40 mL) was added (3-ethoxy-3-oxo-propyl)ammonium chloride (2.79 g, 18.18 mmol) and DIEA (4.7 g, 36.36 mmol). The resulting mixture was stirred at 15° C. for 16 hours to give a solution. EtOAc (30 mL) and water (15 mL) were added to the reaction solution. After separation, the organic layer was washed with brine (15 mL×2), dried over anhydrous Na$_2$SO$_4$, filtered and concentrated to give a crude product. The crude product was purified by silica gel column with EtOAc in PE=(0% to 10% to 20% to 30%) to give the product (2680 mg, 8.45 mmol) as a solid. $^1$H NMR (400 MHz, CDCl$_3$) δ$_H$ 8.23 (br s, 1H), 8.04 (d, 1H), 7.05 (d, 1H), 6.79 (dd, 1H), 4.21 (q, 2H), 3.63 (q, 2H), 2.72 (t, 2H), 1.30 (t, 3H).

To a solution of ethyl 3-(5-bromo-2-nitro-anilino)propanoate (2.68 g, 8.45 mmol) in Ethanol (20 mL) and Water (20 mL) was added Fe (4.73 g, 84.51 mmol) and NH$_4$Cl (4.52 g, 84.51 mmol). The resulting mixture was stirred at 75° C. for 1 hour. The reaction mixture was cooled to room temperature and filtered through Celite. The filtrate was concentrated to give a residue. The residue was dissolved in EtOAc (50 mL) and water (20 mL) and then separated, and the organic layer was washed with brine (30 mL×2), filtered and concentrated to give the crude product (2280 mg, 7.94 mmol) as an oil. $^1$H NMR (400 MHz, CDCl$_3$) 400 MHZ δ$_H$ 6.88-6.70 (m, 2H), 6.57 (d, 1H), 4.18 (q, 2H), 3.84-3.16 (m, 5H), 2.65 (t, 2H), 1.28 (t, 3H).

To a mixture of ethyl 3-(2-amino-5-bromo-anilino)propanoate (2.28 g, 7.94 mmol) in 1N HCl (35 mL, 35 mmol) was added NaNO$_2$ (657.44 mg, 9.53 mmol). The resulting mixture was stirred at 15° C. for 1 hour to give a suspension. Saturated NaHCO$_3$ aqueous (30 mL) and EtOAc (30 mL) was added to the mixture. After separation, the organic layer was washed with brine (30 mL×2), dried over anhydrous Na$_2$SO$_4$, filtered and concentrated to give the crude product. The crude product was purified by silica gel column with EtOAc in PE=(0% to 10% to 20%) to give the product (1600 mg, 5.37 mmol) as an oil. $^1$H NMR (400 MHz, CDCl$_3$) δ$_H$ 7.91 (d, 1H), 7.82 (d, 1H), 7.47 (dd, 1H), 4.86 (t, 2H), 4.12 (q, 2H), 3.09 (t, 2H), 1.20 (t, 3H). LCMS R$_t$=1.104 min in 2.0 min chromatography, MS ESI calcd. for C$_{11}$H$_{13}$BrN$_3$O$_2$ [M+H+2]$^+$ 300.0, found 299.8.

A mixture of ethyl 3-(6-bromobenzotriazol-1-yl)propanoate (300 mg, 1.01 mmol), [4-(trifluoromethoxy)phenyl]boronic acid (248.66 mg, 1.21 mmol), Pd(t-Bu$_3$P)$_2$ (77.14 mg, 0.15 mmol) and K$_3$PO$_4$ (427.25 mg, 2.01 mmol) in 1,4-Dioxane (5 mL) and Water (0.50 mL) was stirred at 80° C. under N$_2$ for 16 hours to give a suspension. The reaction mixture was cooled to room temperature and filtered through Celite. The filtrate was concentrated to give the crude product. The crude product was purified by silica gel column with EtOAc in PE (10% to 20% to 30%) to give the product (360 mg, 0.94 mmol) as a solid. $^1$H NMR (400 MHz, CDCl$_3$) δ$_H$ 8.11 (d, 1H), 7.75 (s, 1H), 7.68 (d, 2H), 7.58 (d, 1H), 7.35 (d, 2H), 4.96 (t, 2H), 4.12 (q, 2H), 3.13 (t, 2H), 1.23-1.16 (m, 3H). LCMS R$_t$=0.885 min in 1.5 min chromatography, MS ESI calcd. for C$_{18}$H$_{17}$F$_3$N$_3$O$_3$ [M+H]$^+$ 380.1, found 380.4.

To a solution of ethyl 3-[6-[4-(trifluoromethoxy)phenyl]benzotriazol-1-yl]propanoate (360 mg, 0.95 mmol) in Ethanol (4 mL) was added N$_2$H$_4$ (91.11 mg, 2.85 mmol). The resulting solution was stirred at 90° C. under N$_2$ for 16 hours to give a solution. The reaction solution was concentrated to give the crude product (300 mg, 0.82 mmol) as a solid. $^1$H NMR (400 MHz, CDCl$_3$) δ$_H$ 8.09 (d, 1H), 7.78 (s, 1H), 7.69 (d, 2H), 7.59 (dd, 1H), 7.35 (d, 2H), 7.07 (br s, 1H), 5.00 (t, 2H), 3.81 (br s, 2H), 3.00 (t, 2H).

To a solution of 3-[6-[4-(trifluoromethoxy)phenyl]benzotriazol-1-yl]propanehydrazide (300 mg, 0.82 mmol) in THF (4 mL) was added 1,1-dimethoxy-N,N-dimethyl-ethanamine (164.07 mg, 1.23 mmol). The resulting solution was stirred at 50° C. for 2 hours to give a solution. The reaction solution was concentrated. The residue was dissolved in Toluene (4 mL). To the solution was added TsOH.H$_2$O (15.62 mg, 0.08 mmol). The resulting mixture was stirred at 100° C. under N$_2$ for 16 hours to give a solution The reaction mixture was concentrated to give the crude product. The crude product was purified by Prep-HPLC (water (0.05% ammonia hydroxide v/v)-ACN) to give compound 15 (183.28 mg, 0.47 mmol) as a solid. $^1$H NMR (400 MHz, CDCl$_3$) δ$_H$ 8.12 (d, 1H), 7.67 (d, 2H), 7.64 (s, 1H), 7.59 (dd, 1H), 7.36 (d, 2H), 5.15 (t, 2H), 3.62 (t, 2H), 2.41 (s, 3H). LCMS R$_t$=1.179 min in 2.0 min chromatography, MS ESI calcd. for C$_{18}$H$_{15}$F$_3$N$_5$O$_2$ [M+H]$^+$ 390.1, found 390.0.

Example 16: Synthesis of Compound 16

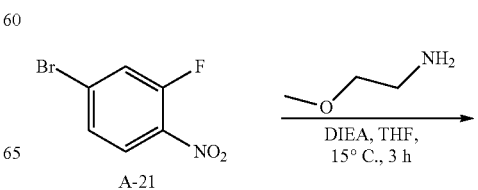

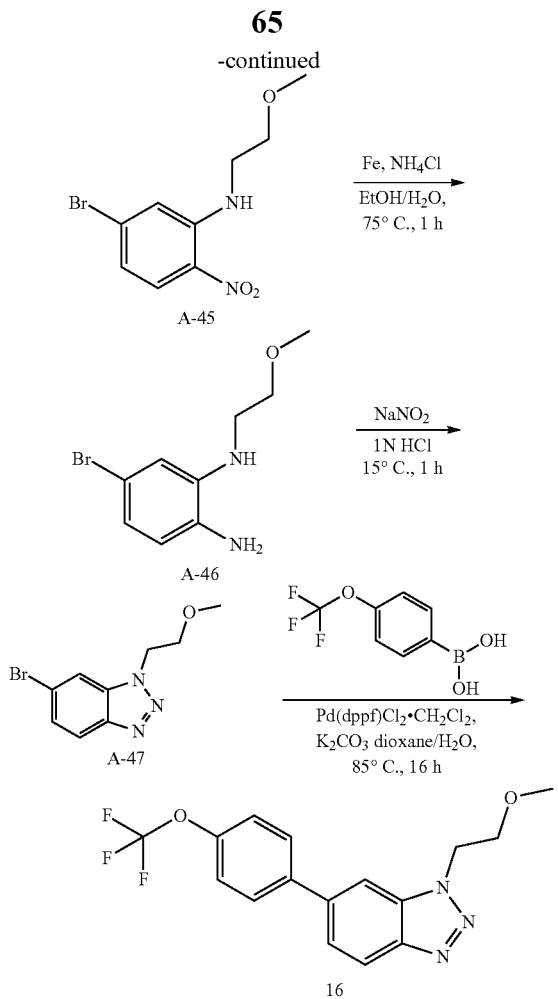

mmol) was added NaNO₂ (334.42 mg, 4.85 mmol) slowly. The resulting mixture was stirred at 15° C. for 1 hour to give a suspension. Saturated NaHCO₃ aqueous (30 mL) and EtOAc (30 mL) were added to the mixture. After separation, the organic layer was washed with brine (30 mL×2), dried over anhydrous Na₂SO₄, filtered and concentrated to give a crude product. The crude product was purified by silica gel column with EtOAc in PE (0% to 10% to 20%) to give the product (740 mg, 2.87 mmol) as an oil. ¹H NMR (400 MHz, CDCl₃) δ$_H$ 7.89 (d, 1H), 7.82 (d, 1H), 7.44 (dd, 1H), 4.76 (t, 2H), 3.86 (t, 2H), 3.30 (s, 3H). LCMS R$_t$=1.013 min in 2.0 min chromatography, MS ESI calcd. for C₉H$_u$BrN₃O [M+H+2]⁺ 258.0, found 257.7.

A mixture of 6-bromo-1-(2-m ethoxy ethyl)benzotriazole (200 mg, 0.78 mmol), [4-(trifluoromethoxy)phenyl]boronic acid (192.98 mg, 0.94 mmol), Pd(dppf)Cl₂·CH₂Cl₂ (95.66 mg, 0.12 mmol) and K₂CO₃ (215.87 mg, 1.56 mmol) in 1,4-Dioxane (4 mL) and Water (0.40 mL) was stirred at 85° C. under N₂ for 16 hours to give a suspension. The reaction mixture was cooled to room temperature and filtered through Celite. The filtrate was concentrated to give a crude product. The crude product was purified by Prep-HPLC (water (0.05% ammonia hydroxide) v/v) to give compound 16 (203.23 mg, 0.60 mmol) as a solid. ¹H NMR (400 MHz, CDCl₃) δ$_H$ 8.11 (d, 1H), 7.76 (s, 1H), 7.68 (d, 2H), 7.58 (dd, 1H), 7.35 (d, 2H), 4.86 (t, 2H), 3.93 (t, 2H), 3.33 (s, 3H). LCMS R$_t$=1.255 min in 2.0 min chromatography, MS ESI calcd. for C₁₆H₁₅F₃N₃O₂ [M+H]⁺ 338.1, found 338.0.

Example 17: Synthesis of Compound 17

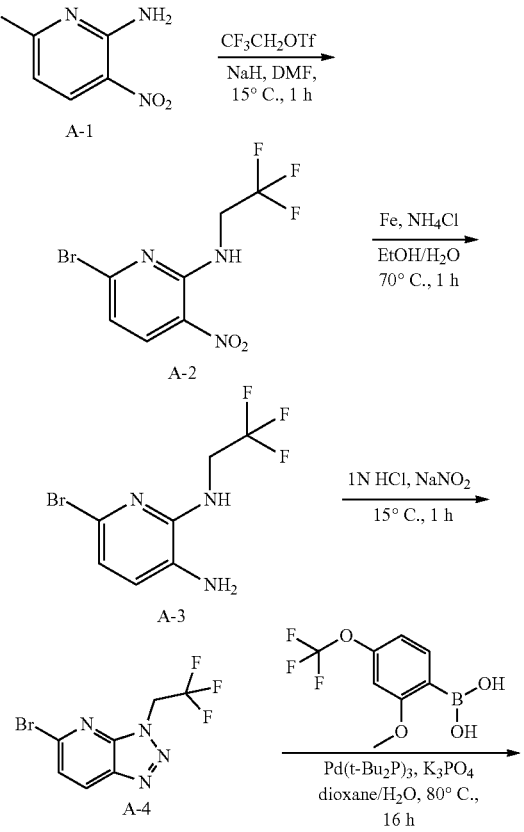

To a solution of 4-bromo-2-fluoro-1-nitro-benzene (1 g, 4.55 mmol) in THF (5 mL) was added 2-methoxyethanamine (512.11 mg, 6.82 mmol) and DIEA (1174.55 mg, 9.09 mmol). The resulting mixture was stirred at 15° C. for 3 hours to give a solution. EtOAc (30 mL) and water (15 mL) was added to the reaction solution. After separation, the organic layer was washed with brine (15 mL×2), dried over anhydrous Na₂SO₄, filtered and concentrated to give the crude product. The crude product was purified by silica gel column with EtOAc in PE (0% to 10% to 20% to 30%) to give the product (1160 mg, 4.22 mmol) as a solid. ¹H NMR (400 MHz, CDCl₃) δ$_H$ 8.23 (br s, 1H), 8.04 (d, 1H), 7.04 (d, 1H), 6.78 (dd, 1H), 3.71-3.67 (m, 2H), 3.50-3.46 (m, 2H), 3.45 (s, 3H).

To a solution of 5-bromo-N-(2-methoxyethyl)-2-nitroaniline (1.16 g, 4.22 mmol) in Ethanol (15 mL) and Water (15 mL) was added Fe (2.36 g, 42.17 mmol) and NH₄Cl (2.25 g, 42.17 mmol). The resulting mixture was stirred at 75° C. for 1 hour. The reaction mixture was cooled to room temperature and filtered through Celite. The filtrate was concentrated to give a residue. The residue was re-dissolved in EtOAc (50 mL) and water (20 mL) and then separated. The organic layer was washed with brine (30 mL×2), filtered and concentrated to give a crude product (990 mg, 4.04 mmol) as oil. ¹H NMR (400 MHz, CDCl₃) δH 6.78 (dd, 1H), 6.74 (d, 1H), 6.57 (d, 1H), 3.81 (d, 1H), 3.65 (t, 2H), 3.40 (s, 5H), 3.25 (t, 2H).

To a mixture of 4-bromo-N2-(2-methoxyethyl)benzene-1,2-diamine (990 mg, 4.04 mmol) in 1N HCl (20 mL, 20

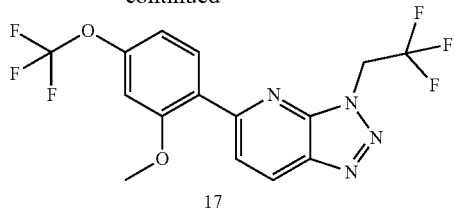

17

To a solution of 6-bromo-3-nitro-pyridin-2-amine (1 g, 4.59 mmol) in DMF (15 mL) was added NaH (220.17 mg, 5.5 mmol) slowly. The resulting mixture was stirred at 15° C. for 30 min. Then 2,2,2-trifluoroethyl trifluoromethanesulfonate (1.27 g, 5.5 mmol) was added to the mixture and the resulting mixture was stirred at 15° C. for 30 min to give a solution.

Saturated NH$_4$Cl aqueous (50 mL) and EtOAc (50 mL) were added to the reaction mixture. After separation, the organic layer was washed with brine (30 mL×2), dried over anhydrous Na$_2$SO$_4$, filtered and concentrated to give the crude product 1300 mg, 3.61 mmol) as a solid $^1$H NMR (400 MHz, CDCl$_3$) $\delta_H$ 8.50-8.35 (m, 1H), 8.27 (d, 1H), 6.95 (d, 1H), 4.38 (d, 2H).

To a solution of 6-bromo-3-nitro-N-(2,2,2-trifluoroethyl) pyridin-2-amine (1.3 g, 4.33 mmol) in Ethanol (20 mL) and Water (20 mL) was added Fe (2.43 g, 43.33 mmol) and NH$_4$Cl (2.32 g, 43.33 mmol). The resulting mixture was stirred at 75° C. for 1 hour to give a suspension. The reaction mixture was cooled to room temperature and filtered through Celite. The filtrate was concentrated to give a residue. The residue was re-dissolved in EtOAc (30 mL) and H$_2$O (20 mL). After separated, the organic layer was washed with brine (20 mL×2), dried over anhydrous Na$_2$SO$_4$, filtered and concentrated to give the crude product (1240 mg, 3.41 mmol) as a solid. LCMS R$_t$=0.751 min in 1.5 min chromatography, MS ESI calcd. for C$_7$H$_8$BrF$_3$N$_3$ [M+H]$^+$ 270.0, found 269.9.

To a stirred mixture of 6-bromo-N2-(2,2,2-trifluoroethyl) pyridine-2,3-diamine (1.24 g, 4.59 mmol) in 1N HCl (25 mL, 22.96 mmol) was added NaNO$_2$ (380.2 mg, 5.51 mmol). The resulting mixture was stirred at 15° C. for 1 hour to give a solution. Saturated NaHCO$_3$ aqueous (50 mL) and EtOAc (100 mL) were added to the reaction mixture. After separation, the organic layer was washed with brine (50 mL×2), dried over anhydrous Na$_2$SO$_4$, filtered and concentrated to give the crude product. The crude product was purified by silica gel column with EtOAc in PE (10% to 30% to 50%) to give the product (380 mg, 1.26 mmol) as a solid. $^1$H NMR (400 MHz, CDCl$_3$) $\delta_H$ 8.29 (d, 1H), 7.59 (d, 1H), 5.31 (q, 2H). LCMS R$_t$=0.760 min in 1.5 min chromatography, MS ESI calcd. for C$_7$H$_5$BrF$_3$N$_4$ [M+H+2]$^+$ 283.0, found 282.8.

A mixture of 5-bromo-3-(2,2,2-trifluoroethyl)triazolo[4,5-b]pyridine (150 mg, 0.53 mmol), [2-methoxy-4-(trifluoromethoxy)phenyl]boronic acid (151.13 mg, 0.64 mmol), K$_3$PO$_4$ (226.6 mg, 1.07 mmol) and Pd(t-Bu$_3$P)$_2$ (40.92 mg, 0.08 mmol) in 1,4-Dioxane (5 mL) and Water (0.50 mL) was stirred at 80° C. under N$_2$ for 16 hours to give a suspension. The reaction was cooled to room temperature and filtered through Celite. The filtrate was concentrated to give the crude product. The crude product was purified by silica gel column (EtOAc in PE=0% to 10% to 20%) to give compound 17 (87.24 mg, 0.22 mmol) as a solid. $^1$H NMR (400 MHz, CDCl$_3$) $\delta_H$ 8.42 (d, 1H), 7.99 (d, 1H), 7.90 (d, 1H), 7.02 (d, 1H), 6.90 (s, 1H), 5.37 (q, 2H), 3.93 (s, 3H). LCMS R$_t$=1.320 min in 2.0 min chromatography, MS ESI calcd. for C$_{15}$H$_{11}$F$_6$N$_4$O$_2$ [M+H]$^+$ 393.1, found 393.0.

Example 18: Synthesis of Compound 18

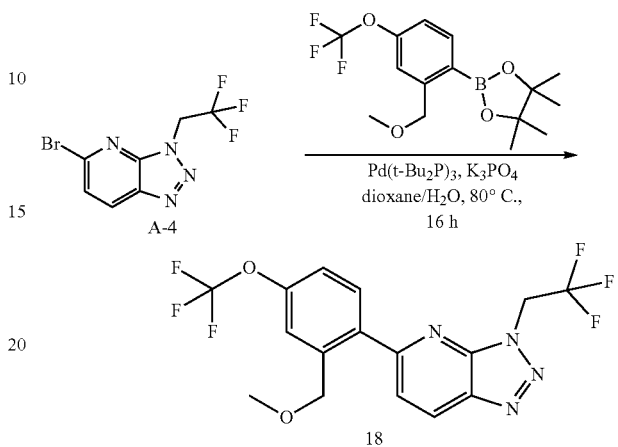

18

A mixture of 5-bromo-3-(2,2,2-trifluoroethyl)triazolo[4,5-b]pyridine (150 mg, 0.53 mmol), 2-[2-(methoxymethyl)-4-(trifluoromethoxy)phenyl]-4,4,5,5-tetramethyl-1,3,2-dioxaborolane (212.72 mg, 0.64 mmol), K$_3$PO$_4$ (226.6 mg, 1.07 mmol) and Pd(t-Bu$_3$P)$_2$ (40.92 mg, 0.08 mmol) in 1,4-Dioxane (5 mL) and Water (0.50 mL) was stirred at 80° C. for 16 hours to give a suspension. The reaction mixture was cooled to room temperature and filtered through Celite. The filtrate was concentrated to give the crude product. The crude product was purified by silica gel column with EtOAc in PE=(0% to 10% to 20%) to give compound 18 (123.75 mg, 0.30 mmol) as a solid. $^1$H NMR (400 MHz, CDCl$_3$) $\delta_H$ 8.52 (d, 1H), 7.65 (d, 1H), 7.61-7.54 (m, 2H), 7.29 (d, 1H), 5.36 (q, 2H), 4.62 (s, 2H), 3.35 (s, 3H). LCMS R$_t$=1.316 min in 2.0 min chromatography, MS ESI calcd. for C$_{16}$H$_{13}$F$_6$N$_4$O$_2$ [M+H]$^+$ 407.1, found 407.1.

Example 19: Synthesis of Compound 19

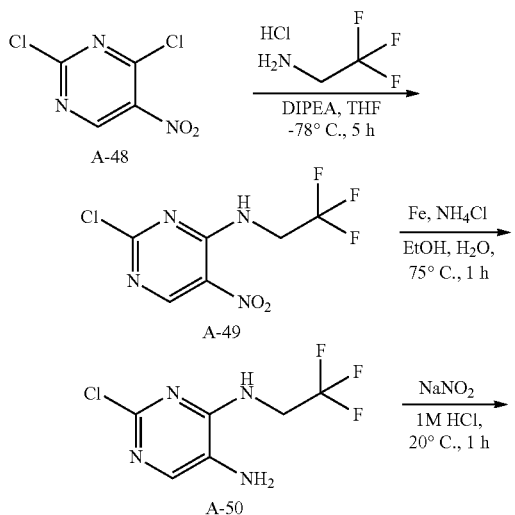

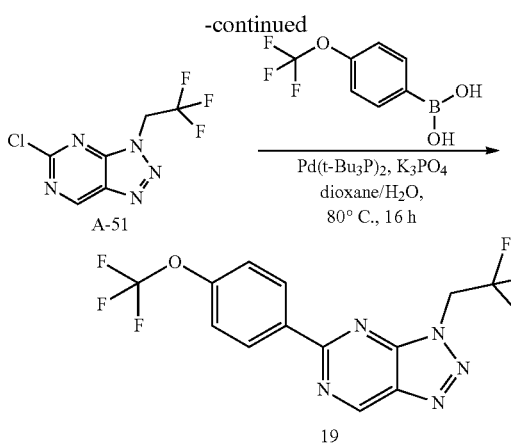

80° C. for 16 hours. After cooling to r.t., the mixture was concentrated. The residue was diluted with H₂O (20 mL), and the mixture was extracted with EtOAc (30 mL×2). The combined organic phase was washed with water (20 mL×2) and brine (20 mL), dried over Na₂SO₄, filtered and concentrated to give the crude product. The crude product was purified by Prep-TLC (PET/EtOAc=4/1) to give compound 19 (52.73 mg, 0.14 mmol) as a solid. ¹H NMR (400 MHz, CDCl₃) δ$_H$ 9.65 (s, 1H), 8.67 (d, 2H), 7.38 (d, 2H), 5.37 (q, 2H). LCMS R$_f$=1.345 min in 2.0 min chromatography, MS ESI calcd. for C₁₃H₈F₆N₅O [M+H]⁺ 364.1, found 364.0.

Example 20: Synthesis of Compound 20

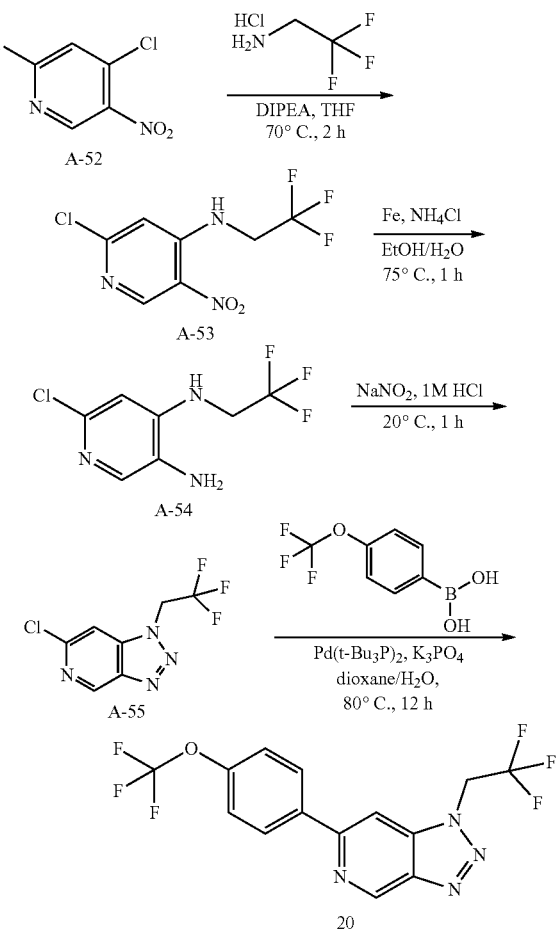

To a mixture of 2,4-dichloro-5-nitro-pyrimidine (4 g, 20.62 mmol) and 2,2,2-trifluoroethanamine hydrochloride (2.79 g, 20.62 mmol) in THF (15 mL) was added DIPEA (5.33 g, 41.24 mmol) at −78° C., then the mixture was stirred at −78° C. for 5 hours. The mixture was diluted with H₂O (30 mL), and the mixture was extracted with EtOAc (50 mL×2). The combined organic phase was washed with water (20 mL×2) and brine (20 mL), dried over Na₂SO₄, filtered and concentrated to give the crude product. The crude product was purified by silica gel column (EtOAc in PE=0% to 10% to 15%) to give the product (2100 mg, 8.11 mmol) as an oil. ¹H NMR (400 MHz, CDCl₃) δ$_H$ 9.15 (s, 1H), 8.58 (br s, 1H), 4.41 (qd, 2H). LCMS R$_f$=0.744 min in 1.5 min chromatography, MS ESI calcd. for C₆H₅ClF₃N₄O₂ [M+H]⁺ 257.0, found 256.8.

To a mixture of 2-chloro-5-nitro-N-(2,2,2-trifluoroethyl)pyrimidin-4-amine (2 g, 7.72 mmol) in Ethanol (20 mL) and Water (20 mL) was added Fe (4.31 g, 77.22 mmol) and NH₄Cl (4.13 g, 77.22 mmol), then the mixture was stirred at 75° C. for 1 hour. The mixture was filtered through Celite, eluted with EtOAc (30 mL×2), and the filtrate was concentrated. The residue was diluted with EtOAc (100 mL), the organic phase was washed with sat.Na₂CO₃ (30 mL), water (20 mL) and brine (20 mL), dried over Na₂SO₄, filtered and concentrated to give the crude product (1600 mg, 6.35 mmol) as a solid. ¹H NMR (400 MHz, CDCl₃) δ$_H$7.77 (S, 1H), 5.34 (br s, 1H), 4.30-4.18 (m, 2H), 3.06 (br s, 2H). LCMS R$_f$=0.594 min in 1.5 min chromatography, MS ESI calcd. for C₆H₇ClF₃N₄ [M+H]⁺ 227.0, found 226.8.

To a mixture of 2-chloro-N⁴-(2,2,2-trifluoroethyl)pyrimidine-4,5-diamine (1.6 g, 7.06 mmol) in 1M HCl (40 mL, 40 mmol) was added NaNO₂ (584.67 mg, 8.47 mmol), then the mixture was stirred at 20° C. for 1 hour. The mixture was basified with Na₂CO₃ (solid) to pH~9, and extracted with EtOAc (50 mL×2). The combined organic phase was washed with water (20 mL×2) and brine (20 mL), dried over Na₂SO₄, filtered and concentrated to give the crude product. The crude product was purified by silica gel column (EtOAc in PE=5% to 15% to 25%) to give the product (1200 mg, 5.05 mmol) as a solid. ¹H NMR (400 MHz, CDCl₃) δ$_H$ 9.48 (s, 1H), 5.30 (q, 2H). LCMS R$_f$=0.667 min in 1.5 min chromatography, MS ESI calcd. for C₆H₄ClF₃N₅ [M+H]⁺ 238.0, found 237.8.

A mixture of 5-chloro-3-(2,2,2-trifluoroethyl)triazolo[4,5-d]pyrimidine (75 mg, 0.32 mmol), [4-(trifluoromethoxy)phenyl]boronic acid (84.51 mg, 0.41 mmol), Pd(t-Bu₃P)₂ (24.2 mg, 0.05 mmol) and K₃PO₄ (134.03 mg, 0.63 mmol) in 1,4-Dioxane (3 mL) and Water (0.50 mL) was stirred at To a mixture of 2,4-dichloro-5-nitro-pyridine (1.5 g, 7.77 mmol) and 2,2,2-trifluoroethanamine hydrochloride (1.58 g, 11.66 mmol) in THF (10 mL) was added DIPEA (3.21 mL, 19.43 mmol), then the mixture was stirred at 70° C. for 2 hours. After cooling to r.t., the mixture was quenched with H₂O (30 mL), then the mixture was extracted with EtOAc (50 mL×2). The combined organic phase was washed with brine (15 mL), dried over Na₂SO₄, filtered and concentrated to give the crude product (2100 mg, 7.67 mmol) as a solid. ¹H NMR (400 MHz, CDCl₃) δ$_H$ 9.09 (s, 1H), 8.46 (br s, 1H), 6.87 (s, 1H), 4.07-3.95 (m, 2H). LCMS R$_f$=0.737 min in 1.5 min chromatography, MS ESI calcd. for C₇H₆ClF₃N₃O₂ [M+H]⁺ 256.0, found 255.8.

To a mixture of 2-chloro-5-nitro-N-(2,2,2-trifluoroethyl)pyridin-4-amine (1.5 g, 5.87 mmol) in Ethanol (20 mL) and Water (20 mL) was added Fe (3.28 g, 58.69 mmol) and NH₄Cl (3.14 g, 58.69 mmol), then the mixture was stirred at 75° C. for 1 hour. The mixture was filtered through Celite, eluted with EtOAc (30 mL×2), and the filtrate was concentrated. The residue was diluted with EtOAc (100 mL), the organic phase was washed with water (20 mL) and brine (20 mL), dried over Na₂SO₄, filtered and concentrated to give the crude product (1250 mg, 4.84 mmol) as a solid. ¹H NMR (400 MHz, CDCl₃) $\delta_H$ 7.74 (s, 1H), 6.56 (s, 1H), 4.86 (br s, 1H), 3.87-3.76 (m, 2H). LCMS $R_t$=0.279 min in 1.5 min chromatography, MS ESI calcd. for $C_7H_8ClF_3N_3$ [M+H]⁺ 226.0, found 226.0.

To a mixture of 6-chloro-N⁴-(2,2,2-trifluoroethyl)pyridine-3,4-diamine (350 mg, 1.55 mmol) in 1M HCl (10 mL, 10 mmol) was added NaNO₂ (128.45 mg, 1.86 mmol), then the mixture was stirred at 20° C. for 1 hour. The mixture was basified with Na₂CO₃ (solid) to pH~9, and extracted with EtOAc (50 mL×2). The combined organic phase was washed with water (20 mL×2) and brine (20 mL), dried over Na₂SO₄, filtered and concentrated to give the crude product. The crude product was purified by silica gel column (EtOAc in PE=5% to 10% to 20%) to give the product (300 mg, 1.25 mmol) as a solid. NMR (400 MHz, CDCl₃) $\delta_H$ 9.31 (d, 1H), 7.58 (s, 1H), 5.24 (q, 2H). LCMS $R_t$=0.692 min in 1.5 min chromatography, MS ESI calcd. for $C_7H_5ClF_3N_4$ [M+H]⁺ 237.0, found 236.8.

A mixture of 6-chloro-1-(2,2,2-trifluoroethyl)triazolo[4,5-c]pyridine (80 mg, 0.34 mmol), [4-(trifluoromethoxy)phenyl]boronic acid (83.56 mg, 0.41 mmol), Pd(t-Bu₃P)₂ (25.92 mg, 0.05 mmol) and K₃PO₄ (143.56 mg, 0.68 mmol) in 1,4-Dioxane (5 mL) and Water (1 mL) was stirred at 80° C. for 12 hours under N₂. After cooling to r.t., the mixture was concentrated. The residue was diluted with H₂O (20 mL), and the mixture was extracted with EtOAc (30 mL×2). The combined organic phase was washed with water (20 mL×2) and brine (20 mL), dried over Na₂SO₄, filtered and concentrated to give the crude product. The crude product was purified by Prep-TLC (PET/EtOAc=4/1) to give compound 20 (58.19 mg, 0.16 mmol) as a solid. ¹H NMR (400 MHz, CDCl₃) $\delta_H$ 9.58 (s, 1H), 8.13 (d, 2H), 7.84 (s, 1H), 7.38 (d, 2H), 5.37 (q, 2H). LCMS $R_t$=1.309 min in 2.0 min chromatography, MS ESI calcd. for $C_{14}H_9F_6N_4O$ [M+H]⁺ 363.1, found 363.0.

Example 21: Synthesis of Compound 21

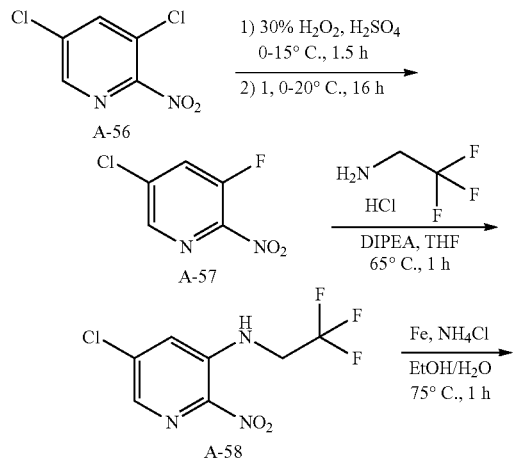

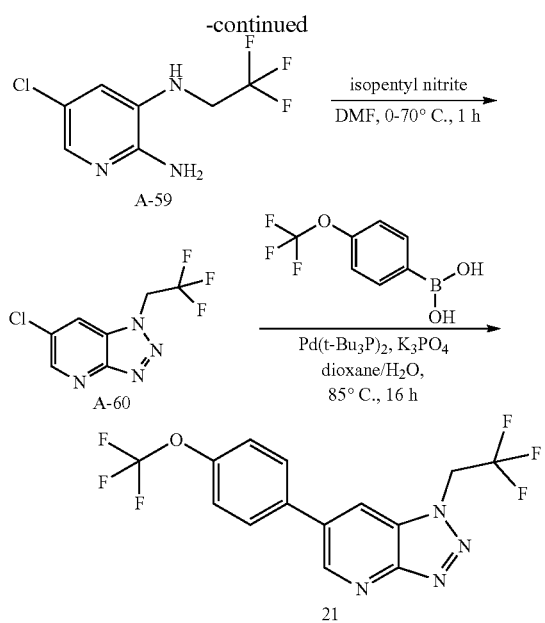

To H₂SO₄ (10 mL, 187.6 mmol) was added 30% H₂O₂ (5 mL, 48.52 mmol) at 0° C., then the mixture was stirred below 15° C. for 1.5 hours. To the mixture was added a solution of 5-chloro-3-fluoro-pyridin-2-amine (1300 mg, 8.87 mmol) in H₂SO₄ (10 mL, 187.6 mmol) at 0° C., then the mixture was stirred at 20° C. for 16 hours. The mixture was diluted with ice-water (150 mL) and the mixture was basified with Na₂CO₃ (solid) to pH~9, and extracted with EtOAc (50 mL×2). The combined organic phase was washed sequentially with 10% aq Na₂S₂O₄ (2×50 mL), sat. NaHCO₃ (50 mL) and brine (50 mL), dried and concentrated to give the crude product. The crude product was purified by silica gel column (EtOAc in PE=0% to 10% to 20%) to give the product (800 mg, 4.53 mmol) as oil. ¹H NMR (400 MHz, DMSO-d₆) $\delta_H$ 8.64 (dd, 1H), 8.61 (d, 1H).

To a mixture of 5-chloro-3-fluoro-2-nitro-pyridine (800 mg, 4.53 mmol) and 2,2,2-trifluoroethanamine hydrochloride (1.23 g, 9.06 mmol) in THF (8 mL) was added DIPEA (2.05 g, 15.86 mmol), then the mixture was stirred at 65° C. for 1 hours. After cooling to r.t., the mixture was concentrated to the residue. The residue was diluted with H₂O (30 mL), and the mixture was extracted with EtOAc (50 mL×2). The combined organic phase was washed with water (20 mL×2) and brine (20 mL), dried over Na₂SO₄, filtered and concentrated to give the crude product. The crude product was purified by silica gel column (EtOAc in PE=0% to 15% to 30%) to give the product (830 mg, 2.99 mmol) as a solid. ¹H NMR (400 MHz, CDCl₃) $\delta_H$ 8.08 (br s, 1H), 7.95 (d, 1H), 7.42 (d, 1H), 4.04-3.94 (m, 2H). LCMS $R_t$=0.758 min in 1.5 min chromatography, MS ESI calcd. for $C_7H_6ClF_3N_3O_2$ [M+H]⁺ 256.0, found 255.9.

To a mixture of 5-chloro-2-nitro-N-(2,2,2-trifluoroethyl)pyridin-3-amine (400 mg, 1.57 mmol) in Ethanol (5 mL) and Water (5 mL) was added Fe (876.44 mg, 15.65 mmol) and NH₄Cl (837.15 mg, 15.65 mmol), then the mixture was stirred at 75° C. for 1 hour. The mixture was filtered through Celite, eluted with EtOAc (20 mL×2), the filtrate was concentrated. The residue was diluted with EtOAc (100 mL), the organic phase was washed with water (20 mL) and brine (20 mL), dried over Na₂SO₄, filtered and concentrated to give the crude product (350 mg, 1.10 mmol) as an oil.

LCMS $R_t$=1.651 min in 3.0 min chromatography, MS ESI calcd. for $C_7H_8ClF_3N_3$ [M+H]$^+$ 226.0, found 226.0.

To a mixture of 5-chloro-N$^3$-(2,2,2-trifluoroethyl)pyridine-2,3-diamine (300 mg, 1.33 mmol) in DMF (5 mL) was added isopentyl nitrite (311.57 mg, 2.66 mmol) at 0° C., then the mixture was stirred at 70° C. for 1 hours. After cooling to r.t., the mixture was diluted with $H_2O$ (20 mL), and the mixture was extracted with EtOAc (30 mL×2). The combined organic phase was washed with water (15 mL×2) and brine (20 mL), dried over $Na_2SO_4$, filtered and concentrated to give the crude product. The crude product was purified by silica gel column (EtOAc in PE=0% to 10% to 20%) to give the product (150 mg, 0.32 mmol) as a solid. $^1$H NMR (400 MHz, CDCl$_3$) $\delta_H$ 8.76 (d, 1H), 8.00 (d, 1H), 5.26 (q, 2H). LCMS $R_t$=0.689 min in 1.5 min chromatography, MS ESI calcd. for $C_7H_5ClF_3N_4$ [M+H]$^+$ 237.0, found 236.9.

A mixture of 6-chloro-1-(2,2,2-trifluoroethyl)triazolo[4,5-b]pyridine (60 mg, 0.25 mmol), [4-(trifluoromethoxy)phenyl]boronic acid (62.67 mg, 0.30 mmol), Pd(t-Bu$_3$P)$_2$ (19.44 mg, 0.04 mmol) and $K_3PO_4$ (107.68 mg, 0.51 mmol) in 1,4-Dioxane (3 mL) and Water (0.50 mL) was stirred at 85° C. for 16 hours under $N_2$. After cooling to r.t., the mixture was concentrated to a residue. The residue was diluted with $H_2O$ (20 mL), and the mixture was extracted with EtOAc (30 mL×2). The combined organic phase was washed with water (15 mL×2) and brine (20 mL), dried over $Na_2SO_4$, filtered and concentrated to give the crude product. The crude product was purified by Prep-TLC (PET/EtOAc=3/1) to give compound 21 (39.17 mg, 0.11 mmol) as a solid. $^1$H NMR (400 MHz, CDCl$_3$) $\delta_H$ 9.03 (d, 1H), 8.05 (s, 1H), 7.69 (d, 2H), 7.42 (d, 2H), 5.33 (q, 2H). LCMS $R_t$=1.215 min in 2.0 min chromatography, MS ESI calcd. for $C_{14}H_9F_6N_4O$ [M+H]$^+$ 363.1, found 363.0.

Example 21: Efficacy of Exemplary Compounds in the Modulation of Late (Persistent) Sodium Current (INaL)

Functional characterization of exemplary compounds to modulate INaL expressed by the Na$_V$1.6 voltage-gated sodium channel was accomplished using the PatchXpress™ high throughput electrophysiology platform (Molecular Devices, Sunnyvale, Calif.). HEK-293 cells expressing recombinant, human Na$_V$1.6 (hNa$_V$1.6) were grown in DMEM/high-glucose Dulbecco's modified, 10% FBS, 2 mM sodium pyruvate, 10 mM HEPES and 400 µg/mL G418. Cells were grown to 50%-80% confluency prior to harvesting. Trypsinized cells were washed, allowed to recover for 1 hour and then resuspended in extracellular recording solution at a concentration of 1×10$^6$ cells/ml. The onboard liquid handling facility of the PatchXpress was used for dispensing cells and applying test compounds. Na$_V$ late currents were evoked by the application of 300 nM ATX-II. INaL was evoked by depolarizing pulses to 0 mV for 200 ms from a non-inactivating holding potential (e.g., −120 mV) at a frequency of 0.1 Hz. INaL amplitude and stability were determined by analyzing the mean current amplitude over the final 20 ms of the test pulse. Following steady state block with exemplary compounds (e.g., as described herein), a Na$^+$ free solution containing an impermeant cation (e.g., Choline or NDMG) was added to confirm the identify of the sodium current. Percent steady-state inhibition of INaL was calculated as: [(INaL_compound)/(INaL_control)]*100, where INaL_compound and INaL_control represent INaL recorded in the presence or absence of compound, respectively.

Results from this assay relating to percent inhibition of NaV1.6 at 1 µM are summarized in Table 1 below. In this table, "A" indicates inhibition of less than 30%; "B" indicates inhibition of between about 30% to about 70%; and "C" indicates inhibition of greater than 70%.

TABLE 1

| Compound No. | INaL hNa$_V$1.6 (1 µM, % inhibition) |
| --- | --- |
| 1 | B |
| 2 | C |
| 3 | B |
| 4 | B |
| 5 | A |
| 6 | B |
| 7 | A |
| 8 | B |
| 9 | B |
| 10 | A |
| 11 | A |
| 12 | B |
| 13 | A |
| 14 | B |
| 15 | B |
| 16 | B |
| 17 | C |
| 18 | C |
| 19 | A |
| 20 | A |
| 21 | A |

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The invention claimed is:

1. A compound of Formula (II), (III) or (IV), wherein the compound of Formula (II) is:

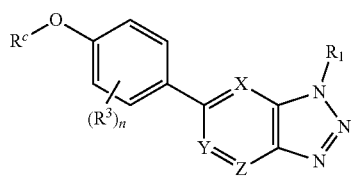

(II)

or a pharmaceutically acceptable salt thereof, wherein:
each of X, Y, and Z is independently N or $CR^2$;
$R^1$ is independently alkyl, alkenyl, alkynyl, carbocyclyl, heterocyclyl, or heteroaryl, wherein alkyl, alkenyl, alkynyl, carbocyclyl, heterocyclyl, and heteroaryl are optionally substituted with one or more $R^4$;
$R^2$ is hydrogen, alkyl or halogen;
each $R^3$ is independently alkyl, halo, cyano, nitro, carbocyclyl, heterocyclyl, —$OR^c$, —$N(R^d)_2$, —$C(O)R^c$, —$C(O)OR^c$, or —$C(O)N(R^d)_2$, wherein alkyl, carbocyclyl, and heterocyclyl are optionally substituted with one or more $R^5$;
each $R^4$ and $R^5$ is independently alkyl, halo, cyano, nitro, 5 or 6-membered heteroaryl, or —$OR^c$, wherein the 5 or 6 membered heteroaryl is optionally substituted with alkyl;
each $R^c$ is independently hydrogen, alkyl, aryl, carbocyclyl, or heteroaryl, wherein alkyl, aryl, carbocyclyl, and heteroaryl is optionally substituted by one or more $R^6$;
each $R^d$ is independently hydrogen or alkyl;
each $R^6$ is independently alkyl, carbocyclyl, heterocyclyl, halo, cyano, nitro, or —OH, and
n is 0, 1, 2, or 3;

wherein the compound is not a compound selected from the group consisting of:

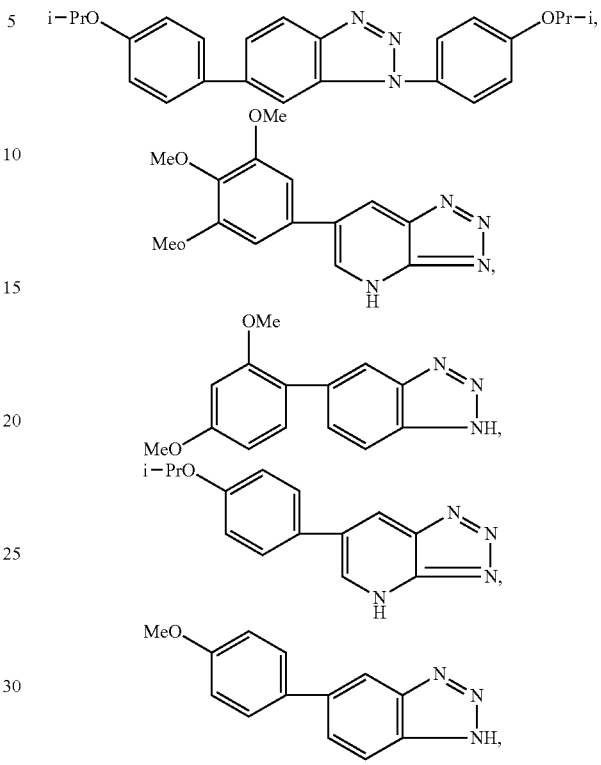

or a pharmaceutically acceptable salt thereof;
wherein the compound of Formula (III) is:

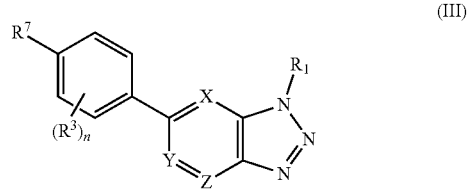

(III)

or a pharmaceutically acceptable salt thereof, wherein:
each of X, Y, and Z is independently N or $CR^2$;
$R^1$ is independently hydrogen, alkyl, alkenyl, alkynyl, carbocyclyl, heterocyclyl, aryl, or heteroaryl, wherein alkyl, alkenyl, alkynyl, carbocyclyl, heterocyclyl, aryl, and heteroaryl are optionally substituted with one or more $R^4$;
$R^2$ is hydrogen, alkyl or halogen;
$R^7$ is carbocyclyl optionally substituted with one or more $R^5$;
each $R^3$ is independently alkyl, halo, cyano, nitro, carbocyclyl, heterocyclyl, —$OR^c$, —$N(R^d)_2$, —$C(O)R^c$, —$C(O)OR^c$, or —$C(O)N(R^d)_2$, wherein alkyl, carbocyclyl, and heterocyclyl are optionally substituted with one or more $R^5$;
each $R^4$ and $R^5$ is independently alkyl, halo, cyano, nitro, 5 or 6-membered heteroaryl, or —$OR^c$, wherein the 5 or 6 membered heteroaryl is optionally substituted with alkyl;

each $R^c$ is independently hydrogen, alkyl, aryl, carbocyclyl, or heteroaryl, wherein alkyl, aryl, carbocyclyl, and heteroaryl is optionally substituted by one or more $R^6$;

each $R^d$ is independently hydrogen or alkyl;

each $R^6$ is independently alkyl, carbocyclyl, heterocyclyl, halo, cyano, nitro, or —OH, and n is 0, 1, 2, or 3; or wherein the compound of Formula (IV) is:

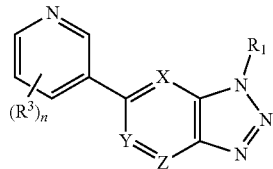
(IV)

or a pharmaceutically acceptable salt thereof, wherein:

each of X, Y, and Z is independently N or $CR^2$;

$R^1$ is independently hydrogen, alkyl, alkenyl, alkynyl, carbocyclyl, heterocyclyl, aryl, or heteroaryl, wherein alkyl, alkenyl, alkynyl, carbocyclyl, heterocyclyl, aryl, and heteroaryl are optionally substituted with one or more $R^4$;

$R^2$ is hydrogen, alkyl or halogen;

each $R^3$ is independently alkyl, halo, cyano, nitro, carbocyclyl, heterocyclyl, —$OR^c$, —$N(R^d)_2$, —$C(O)R^c$, —$C(O)OR^c$, or —$C(O)N(R^d)_2$, wherein alkyl, carbocyclyl, and heterocyclyl are optionally substituted with one or more $R^5$;

each $R^4$ and $R^5$ is independently alkyl, halo, cyano, nitro, 5 or 6-membered heteroaryl, or —$OR^c$, wherein the 5 or 6 membered heteroaryl is optionally substituted with alkyl;

each $R^c$ is independently hydrogen, alkyl, aryl, carbocyclyl, or heteroaryl, wherein alkyl, aryl, carbocyclyl, and heteroaryl is optionally substituted by one or more $R^6$;

each $R^d$ is independently hydrogen or alkyl;

each $R^6$ is independently alkyl, carbocyclyl, heterocyclyl, halo, cyano, nitro, or —OH, and n is 0, 1, 2, or 3;

wherein the compound is not a compound selected from the group consisting of:

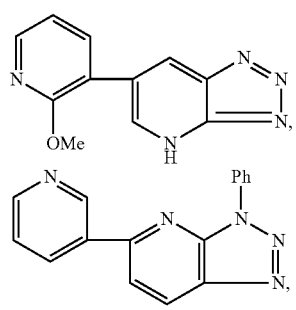

or a pharmaceutically acceptable salt thereof.

2. The compound of claim 1, wherein the compound of Formula (II) is a compound of Formula (II-a):

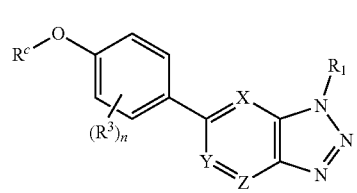
(II-a)

or a pharmaceutically acceptable salt thereof, wherein:

each of X, Y, and Z is independently N or $CR^2$;

$R^1$ is independently alkyl, alkenyl, alkynyl, carbocyclyl, heterocyclyl, or heteroaryl, wherein alkyl, alkenyl, alkynyl, carbocyclyl, heterocyclyl, and heteroaryl are optionally substituted with one or more $R^4$;

$R^2$ is hydrogen, alkyl or halogen;

each $R^3$ is independently alkyl, halo, cyano, nitro, carbocyclyl, heterocyclyl, —$OR^c$, —$N(R^d)_2$, —$C(O)R^c$, —$C(O)OR^c$, or —$C(O)N(R^d)_2$, wherein alkyl, carbocyclyl, and heterocyclyl are optionally substituted with one or more $R^5$;

each $R^4$ and $R^5$ is independently alkyl, halo, cyano, nitro, 5 or 6-membered heteroaryl, or —$OR^c$, wherein the 5 or 6 membered heteroaryl is optionally substituted with alkyl;

each $R^c$ is independently hydrogen, alkyl, aryl, carbocyclyl, or heteroaryl, wherein alkyl, aryl, carbocyclyl, and heteroaryl is optionally substituted by one or more $R^6$;

each $R^d$ is independently hydrogen or alkyl;

each $R^6$ is independently alkyl, carbocyclyl, heterocyclyl, halo, cyano, nitro, or —OH, and n is 0, 1, 2, or 3.

3. The compound of claim 1, wherein:

X is N, and Y and Z are $CR^2$; or

Y is N, and X and Z are $CR^2$; or

Z is N, and Y and X are $CR^2$; or

X and Z are N, and Y is $CR^2$; or

X and Y are N, and Z is $CR^2$; or

Z and Y are N, and X is $CR^2$.

4. The compound of claim 1, wherein $R^2$ is hydrogen.

5. The compound of claim 1, wherein $R^1$ is alkyl optionally substituted with 1, 2, or 3 of $R^4$.

6. The compound of claim 1, wherein:

$R^3$ is alkyl or —$OR^c$, wherein alkyl is optionally substituted with one or more $R^5$.

7. The compound of claim 1, wherein:

$R^4$ is halo or 5 or 6-membered heteroaryl, wherein the 5 or 6 membered heteroaryl is optionally substituted with alkyl; or $R^4$ is halo.

8. The compound of claim 1, wherein $R^5$ is cyano or —$OR^c$.

9. The compound of claim 1, wherein $R^c$ is alkyl or carbocyclyl, wherein the alkyl or carbocyclyl is optionally substituted with 1, 2, or 3 of $R^6$.

10. The compound of claim 1, wherein $R^6$ is halo.

11. The compound of claim 1, wherein n is 0 or 1.

12. The compound of claim 1, wherein the compound is selected from the group consisting of:

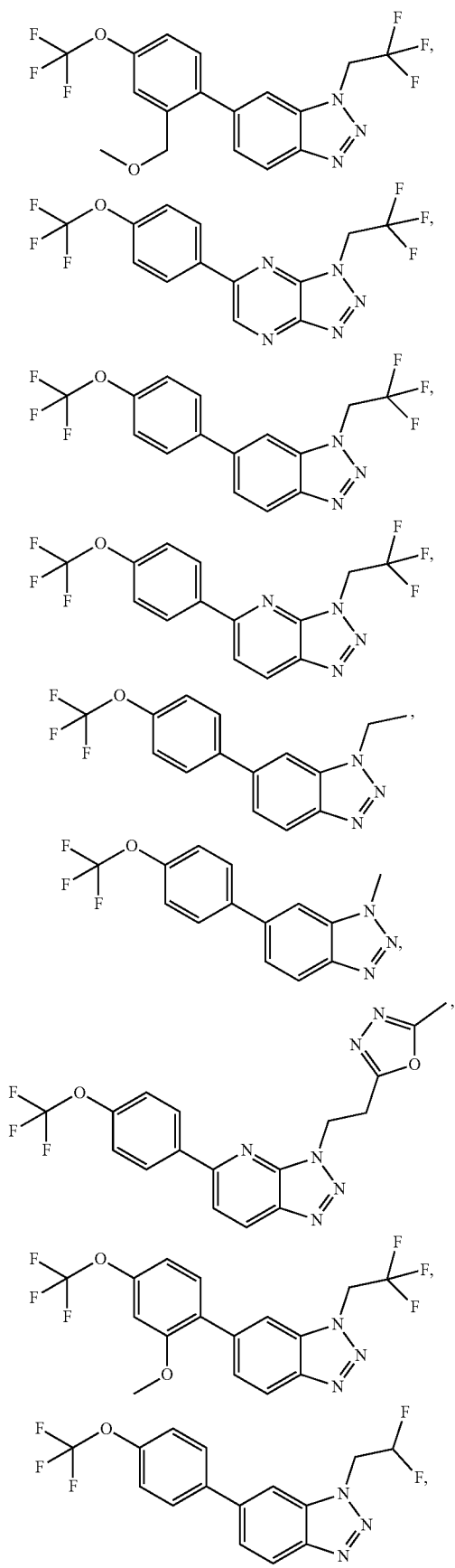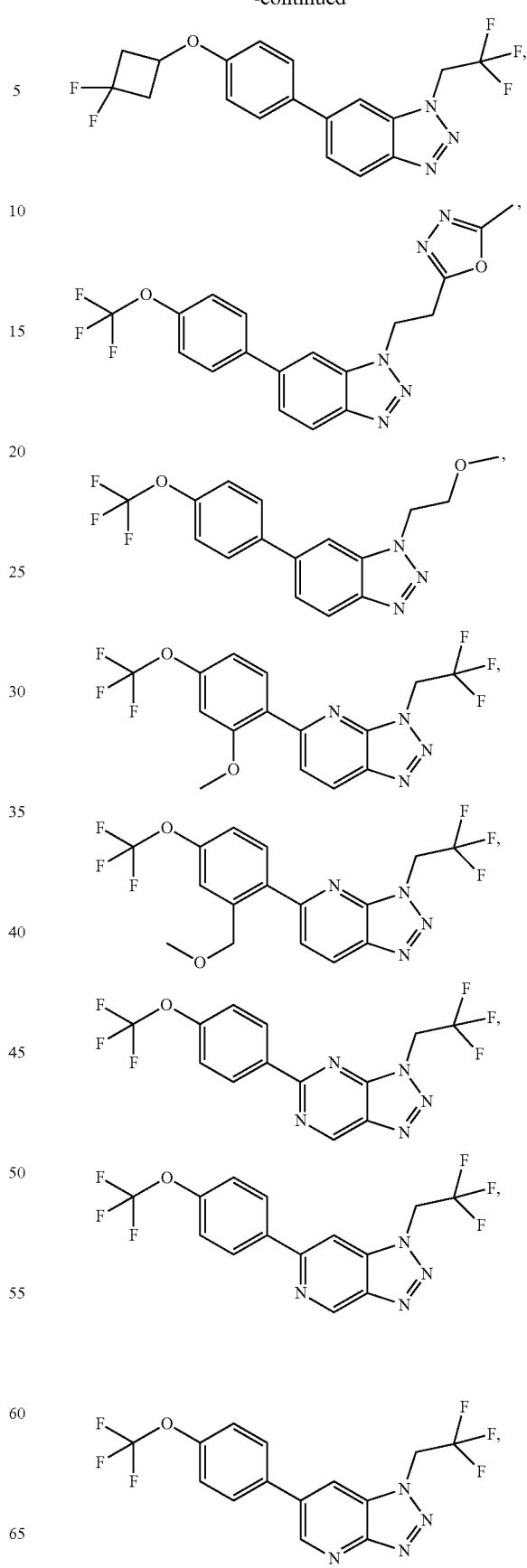

-continued or a pharmaceutically acceptable salt thereof.

13. The compound of claim 1, wherein the compound of Formula (IV) is a compound of Formula (IV-a):

(IV-a)

or a pharmaceutically acceptable salt thereof, wherein:
each of X, Y, and Z is independently N or CR²;
R¹ is independently alkyl, alkenyl, alkynyl, carbocyclyl, heterocyclyl, aryl, or heteroaryl, wherein alkyl, alkenyl, alkynyl, carbocyclyl, heterocyclyl, aryl, and heteroaryl are optionally substituted with one or more R⁴;
R² is hydrogen, alkyl or halogen;
R⁷ and each R³ are independently, for each occurrence, alkyl, halo, cyano, nitro, carbocyclyl, heterocyclyl, —OR$^c$, —N(R$^d$)₂, —C(O)R$^c$, —C(O)OR$^c$, or —C(O)N(R$^d$)₂, wherein alkyl, carbocyclyl, and heterocyclyl are optionally substituted with one or more R⁵;
each R⁴ and R⁵ is independently alkyl, halo, cyano, nitro, 5 or 6-membered heteroaryl, or —OR$^c$, wherein the 5 or 6 membered heteroaryl is optionally substituted with alkyl;
each R$^c$ is independently hydrogen, alkyl, aryl, carbocyclyl, or heteroaryl, wherein alkyl, aryl, carbocyclyl, and heteroaryl is optionally substituted by one or more R⁶;
each R$^d$ is independently hydrogen or alkyl;
each R⁶ is independently alkyl, carbocyclyl, heterocyclyl, halo, cyano, nitro, or —OH, and
m is 0, 1, or 2.

14. A pharmaceutical composition comprising a compound of claim 1, or pharmaceutically acceptable salt thereof, and a pharmaceutically acceptable carrier.

* * * * *